US009464035B2

(12) United States Patent
Marugan et al.

(10) Patent No.: US 9,464,035 B2
(45) Date of Patent: Oct. 11, 2016

(54) SALICYLIC ACID DERIVATIVES USEFUL AS GLUCOCEREBROSIDASE ACTIVATORS

(71) Applicants: The United States of America, as Represented by the Secretary, Department of Health and Human Services, Washington, DC (US); The University of Kansas, Lawrence, KS (US)

(72) Inventors: Juan Jose Marugan, Gaithersburg, MD (US); Wei Zheng, Potomac, MD (US); Samarjit Patnaik, Gaithersburg, MD (US); Noel Southall, Potomac, MD (US); Ellen Sidransky, Bethesda, MD (US); Ehud Goldin, Rockville, MD (US); Wendy Westbroek, Rockville, MD (US); Elma Aflaki, Rockville, MD (US); Steven Andrew Rogers, Lawrence, KS (US); Frank John Schoenen, Lawrence, KS (US)

(73) Assignees: THE UNITED STATES OF AMERICA, AS REPRESENTED BY THE SECRETARY, DEPARTMENT OF HEALTH AND HUMAN SERVICES, Washington, DC (US); THE UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 14/388,494

(22) PCT Filed: Mar. 15, 2013

(86) PCT No.: PCT/US2013/032253
§ 371 (c)(1),
(2) Date: Sep. 26, 2014

(87) PCT Pub. No.: WO2013/148333
PCT Pub. Date: Oct. 3, 2013

(65) Prior Publication Data
US 2015/0065469 A1    Mar. 5, 2015

Related U.S. Application Data

(60) Provisional application No. 61/616,758, filed on Mar. 28, 2012.

(51) Int. Cl.
*C07C 235/64* (2006.01)
*C07C 235/60* (2006.01)
*C07C 237/22* (2006.01)

(52) U.S. Cl.
CPC .......... *C07C 235/64* (2013.01); *C07C 235/60* (2013.01); *C07C 237/22* (2013.01); *C07B 2200/07* (2013.01)

(58) Field of Classification Search
None
See application file for complete search history.

(56) References Cited

U.S. PATENT DOCUMENTS

2007/0281975 A1    12/2007    Mugrage et al.

FOREIGN PATENT DOCUMENTS

| CA | 2504207 A1 | 5/2004 |
|---|---|---|
| EP | 0080355 A1 | 6/1983 |
| JP | 1991206449 A | 9/1991 |
| WO | 2005123738 A1 | 6/2005 |
| WO | 2007008541 A2 | 1/2007 |
| WO | 2007139856 A2 | 12/2007 |
| WO | 2007139860 A2 | 12/2007 |
| WO | 2008045664 A2 | 4/2008 |
| WO | 2008063671 A2 | 5/2008 |
| WO | 2011139636 A1 | 10/2011 |
| WO | 2013148333 A1 | 10/2013 |

OTHER PUBLICATIONS

CAS Registry No. 1012604-75-9, Apr. 2008.*
Ito N, Tamano S, Shirai T. A medium-term rat liver bioassay for rapid in vivo detection of carcinogenic potential of chemicals. Cancer Sci. Jan. 2003;94(1):3-8.*
Aguilar et al. "Molecular Basis for Beta-Glucosidase Inhibition by Ring-Modified Calystegine Analogues" Nov. 3, 2008; 9(16): 2612.
Chen et al., "Studies on Synthesis of Carboxylphenoxyacetic Acid Derivatives Using Liquid-Liquid Phase Transfer Catalysis", Gaodeng Xuexiao Huaxue Xuebao; Chemical Journal of Chinese Universities; Sep. 1, 1991; pp. 1195-1199.
Grabowski, "Phenotype, Diagnosis, and treatment of Gaucher's Diseases" The Lancet, 2008, 372, 1263.
International Preliminary Report on Patentability and Written Opinion for International Application No. PCT/US2013/032253; International Filing Date: Mar. 15, 2013; Date of Issuance: Oct. 1, 2014; 7 Pages.
International Search Report for International Patent Application No. PCT/US2013/032253, International Filing Date: Mar. 15, 2013; Date of Mailing: Jul. 12, 2013; 2 Pages.
Marugan et al., "Evaluation of Quinazoline Analogues as Glucocerebrosidase Inhibitors with Chaperone Activity" J. Med. Chem., 54 (4); (2011); pp. 1033-1058.

Marugan et al., "Non-Iminosugar Glucocerebrosidase Small Molecule Chaperones" Med. Chem. Commun.; 3; 56; (2012); pp. 56-60.
Motabar et al., "A High Throughput Glucocerebrosidase Assay Using the Natural Substrate Glucosylceramide" Anal. Bioanal. Chem. 402, (2012), pp. 731-739.
Schulze et al. "Principles of Lysosomal Membrane Degradition Cellular Topology and biochemistry of Lysosomal Lipid Degradation" Biochimica et Biophysica Acta; 1793 (2009) pp. 674-683.
Tropak et al. "Identification of Pharmacological Chaperones for Gaucher Disease and Characterization of their Effects on Beta-Glucocerebrosidase by Hydrogen/Deuterium Exchange Mass Spectrometry." Nov. 3, 2008; 9(16): pp. 2650-2661.
Attiyat et al.; "Synthesis and Potentiometric Study of Acyclic Monoxadiamides as Ionophores in Ion-Selective Electrodes"; Electroanalysis, 2(2); 1990; pp. 119-125.
Campbell et al.; "Gaucher disease and the synucleinopathies: refining the relationship"; Orphanet Journal of Rare Diseases, vol. 7, No. 12; 2012; pp. 1-7.
Curtius et al.; "Behavior of salicylacetic acid and phenylglycine-o-carboxylic acid in the azide rearrangement"; Journal fuer Praktische Chemie (Leipzig) (1930), 125; English abstract only, 1 page.
JP1991206449; Published Sep. 9, 1991; English Abstract Only; 1 page.
Zheng et al. "Three Classes of Glucocerebrosidase Inhibitors Identified by Quantitative High-Thorughput Screening are Chaperone Leads for Gaucher Disease" PNAS; vol. 104, No. 32 (Aug. 7, 2007), pp. 13192-13197.

\* cited by examiner

*Primary Examiner* — Theodore R West
(74) *Attorney, Agent, or Firm* — Cantor Colburn LLP

(57) ABSTRACT

Compounds of Formula (I) and the pharmaceutically acceptable salts thereof are disclosed. The variables. $R_1$-$R_{13}$, m, n, o, and p are disclosed herein. The compounds are useful for treating Gaucher disease and inhibiting the onset of Gaucher disease symptoms in a patient having a GBA gene mutation and for treating Parkinson's disease. Pharmaceutical compositions containing compounds of Formula (I) and methods of treatment comprising administering compounds of Formula (I) are also disclosed.

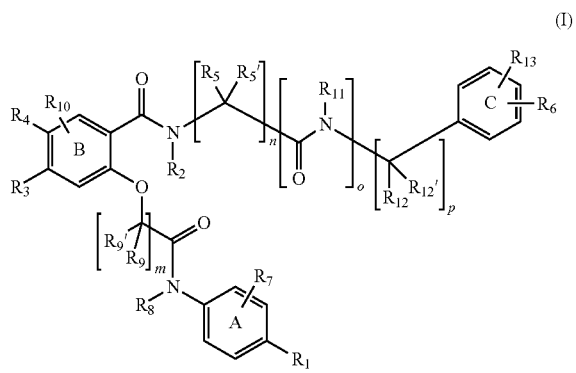

11 Claims, 1 Drawing Sheet

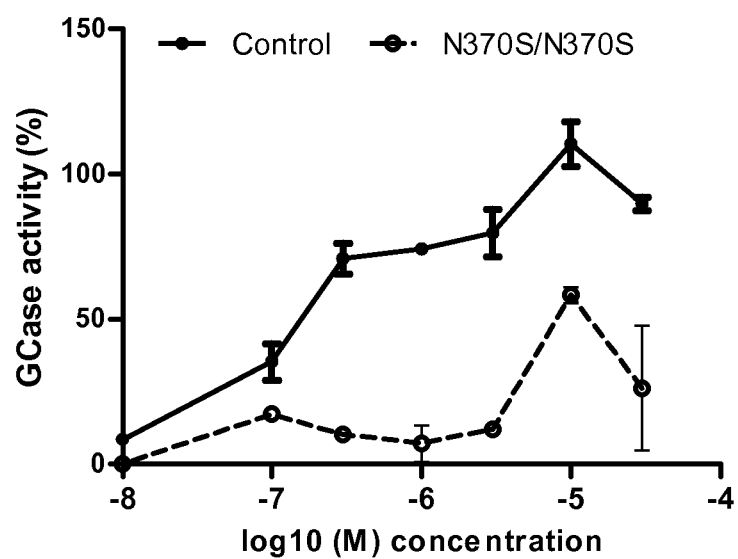

SALICYLIC ACID DERIVATIVES USEFUL AS GLUCOCEREBROSIDASE ACTIVATORS

CROSS-REFERENCE TO RELATED APPLICATIONS

This Application is a U.S. National Stage Application of PCT/US2013/032253 filed Mar. 15, 2013, which claims priority to U.S. Provisional Patent Application No. 61/616,758 filed Mar. 28, 2012, both of which are incorporated by reference in their entirety.

STATEMENT OF GOVERNMENT SUPPORT

This invention was made in part with government support from the National Institutes of Health. The government has certain rights in this invention.

BACKGROUND

Gaucher disease is a rare disease affecting 1 in 40,000 babies born with a particular high frequency in the Ashkenazi Jews of eastern European descent (about 1 in 800 live births). It is caused by inherited genetic mutations in the GBA (glucosidase, beta acid) gene, which result in reduced activity of glucocerebrosidease (GCase or acid beta-glucocerebrosidase), an enzyme present in cellular organelles called lysosomes, responsible for the breakdown of a fatty material called glucocerebroside (or glucosyl ceramide). The accumulation of this lipid inside cells causes them to swell abnormally creating problems throughout the body. The disease has been categorized into three types: Neuronopathic (types 2, 3) and non-neuronopathic (type 1) with mild to severe symptoms that can appear at anytime from infancy to adulthood. Clinical manifestations include enlarged spleen/liver, anemia, lack of platelets, neurodegeneration, and bone disease with varying severity depending on the type of disease and time of diagnosis. The reduction in GCase activity has been attributed to the lack of protein in the lysosome. After production in the endoplasmic reticulum (ER) proteins that do not fold properly are degraded in the ER and not transported to the lysosome where they can hydrolyze glucocerebroside.

Existing treatment options for Gaucher disease include enzyme replacement (CEREZYME) or substrate reduction therapy (ZAVESCA) which cost between $100,000 to >$200,000 per year. The development of the iminosugar isofagomine (PLICERA) as a molecular chaperone was halted after Phase 2 clinical trials showed an increase in the amount of GCase in white blood cells but a lack in the reduction of visceral symptoms. Thus there is an unmet need for the development of novel chaperone therapy for Gaucher disease. The present disclosure fulfills this need and provides additional advantages set forth in the following disclosure.

SUMMARY

Described herein are substituted salicylic acid derivatives and related compounds, their methods of manufacture, compositions containing the described compounds, and methods of use of the described compounds. Thus in a first aspect, a compound of Formula (I) and the pharmaceutically acceptable salts of a compound of Formula (I) is provided

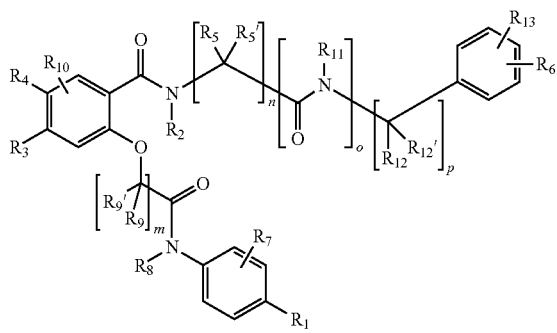

Formula (I)

The within Formula (I) the following conditions are met.

Any or all of the three phenyl rings may be replaced with another heterocycle, such as a 5- or 6-membered heteroaryl group containing 1, 2, or 3 heteroatoms selected from N, O, and S. In certain embodiments one or more of the phenyl groups is replaced by a pyridyl.

m is 1 or 2; n is 0, 1, or 2; o is 0 or 1; and p is 0, 1 or 2.

$R_1$ is a halogen, $C_1$-$C_2$alkyl, or $C_1$-$C_2$alkoxy.

$R_2$ is hydrogen or $C_1$-$C_4$alkyl.

$R_3$ and $R_4$ are independently selected from hydrogen, halogen, amino, cyano, —$CONH_2$, $C_1$-$C_6$alkyl, $C_1$-$C_6$alkoxy, $C_2$-$C_6$alkanoyl, $C_1$-$C_6$alkylester, (mono- and di-$C_1$-$C_4$alkylamino)$C_0$-$C_4$alkyl, ($C_3$-$C_7$cycloalkyl)$C_0$-$C_4$alkyl, phenyl, heterocycloalkyl, $C_1$-$C_2$haloalkyl, and $C_1$-$C_2$haloalkoxy.

$R_5$, $R_5'$, $R_9$, $R_9'$, and $R_{12}$, $R_{12}'$ are independently chosen at each occurrence from hydrogen, fluoro, phenyl, ($C_3$-$C_6$cycloalkyl)$C_0$-$C_2$alkyl, and $C_1$-$C_4$alkyl;

$R_6$ is one substituent selected from hydrogen, halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

$R_7$, $R_{10}$, and $R_{13}$ are each 0 or 1 or more substituents independently chosen from halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

$R_8$ and $R_{11}$ are independently chosen from hydrogen and $C_1$-$C_4$alkyl.

In another aspect a pharmaceutical composition comprising a compound of Formula (I), or salt thereof, together with a pharmaceutically acceptable carrier, is provided.

Also provided herein is a method of treating Gaucher disease in a patient or preventing or reducing the severity of the symptoms of Gaucher disease in a patient having a GBA gene mutation comprising providing an effective amount of a compound of Formula (I) or pharmaceutically acceptable salt thereof to the patient.

Yet another aspect provides a method of increasing the amount of beta glucocerebrosidase in the white blood cells of patient having a GBA gene mutation, comprising providing an effective amount of a compound of Formula (I) to the patient.

BRIEF DESCRIPTION OF THE DRAWINGS

FIG. 1. GCase Specific Activity in human macrophages with increasing concentration of NCGC607 (1 µM). FIG. 1 shows Control (wt) GCase specific activity (as measured by hydrolysis of Glc-4MU is inherently more than in a patient with the N370S/N370S genotype. With increasing Compound NCGC607 (of this disclosure) concentration GCase activity goes up. With patient macrophages at 100 nM (10-7M) NGCG607 the specific activity is more than wt (with no compound). In fact at 1 mM the specific activity is the lowest. This was the concentration chosen in the earlier experiments. At 10 mM specific activity is very high. At the highest concentration cytotoxicity is evident by the downward slope in both wt and mutant macrophages (this is also seen under microscope).

DETAILED DESCRIPTION

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include and $^{11}C$, $^{13}C$, and $^{14}C$.

Formula (I) includes all pharmaceutically acceptable salts of Formula (I) and all subformula of Formula (I) such as Formula II-V.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene groups replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group.

A dash ("-") that is not between two letters or symbols is used to indicate a point of attachment for a substituent.

"Alkyl" includes both branched and straight chain saturated aliphatic hydrocarbon groups, having the specified number of carbon atoms. The term $C_1$-$C_2$alkyl means an alkyl group having from 1 to about 2 carbon atoms, e.g., methyl and ethyl, respectively Likewise "alkenyl" is a branched or straight chain unsaturated hydrocarbon group having the specified number of carbon atoms and at least one carbon-carbon double bond and alkynyl is a branched or straight chain unsaturated hydrocarbon group having the specified number of carbon atoms and at least one carbon-carbon triple bond.

"Alkanoyl" is an alkyl group as defined above, attached through a keto (—(C=O)—) bridge Alkanoyl groups have the indicated number of carbon atoms, with the carbon of the keto group being included in the numbered carbon atoms. For example a $C_2$alkanoyl group is an acetyl group having the formula $CH_3$(C=O)—.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane "(Cycloalkyl)$C_0$-$C_n$alkyl" is a cycloalkyl group attached to the position it substitutes either by a single covalent bond ($C_0$) or by an alkylene linker having 1 to n carbon atoms.

"Halo" or "halogen" means fluoro, chloro, bromo, or iodo.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Mono- and/or di-alkylamino" means secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

"Pharmaceutical compositions" means compositions comprising at least one active agent, such as a compound or salt of Formula (I), and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any symptom of a beta-glucocerebrosidase mediated disorder, e.g., cause regression of the disorder, liver function, reduce anemia, increase platelet count, or decrease the rate of neurodegeneration or bone degeneration. In certain embodiments treatment of Gaucher disease may be commenced before the patient presents symptoms of the disease.

A "therapeutically effective amount" of a pharmaceutical composition means an amount effective, when administered to a patient, to provide a therapeutic benefit such as an amelioration of symptoms, e.g., an amount effective to decrease the symptoms of Gaucher disease.

A significant change is any detectable change that is statistically significant in a standard parametric test of statistical significance such as Student's T-test, where p<0.05.

Chemical Description

Compounds of Formula (I) may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

Small molecules which activate the GCase enzyme are disclosed herein. The data suggests these small molecules may be acting as chaperones which help the misfolded enzyme to fold properly and be trafficked from the endoplasmic reticulum to the lysosome. Most small molecule chaperones described in literature are inhibitors of GCase and thus can potentially inhibit enzyme activity in the lysosome. The present chemical series is advantageous as the compounds do not inhibit, but rather activate GCase. The chemical class of salicylic acid derivatives is also structurally distinct from iminosugars, often described as chaperones in literature, and holds promise towards selectivity against other glycosidases.

The disclosure also contains the following specific embodiments:

(1) A compound of pharmaceutically acceptable salt thereof, of Formula (I) as shown in the SUMMARY section in which the variables carry the following definitions:

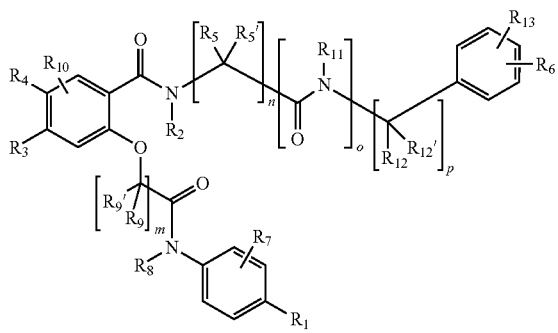

Formula (I)

m is 1 or 2; n is 0, 1, or 2; o is 0 or 1; and p is 0, 1 or 2.

$R_1$ is a halogen, $C_1$-$C_2$alkyl, or $C_1$-$C_2$alkoxy.

$R_2$ is hydrogen or $C_1$-$C_4$alkyl.

$R_3$ and $R_4$ are independently selected from hydrogen, halogen, amino, cyano, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

$R_5$, $R_5'$, $R_9$, $R_9'$, and $R_{12}$, $R_{12}'$ are independently chosen at each occurrence from hydrogen, fluoro, phenyl, ($C_3$-$C_6$cycloalkyl)$C_0$-$C_2$alkyl, and $C_1$-$C_4$alkyl.

$R_6$ is one substituent selected from hydrogen, halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

$R_7$, $R_{10}$, and $R_{13}$ are each 0 or 1 or more substituents independently chosen from halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

$R_8$ and $R_{11}$ are independently chosen from hydrogen and $C_1$-$C_4$alkyl.

With the proviso that when n, o, and p are all 0, $R_6$ is a non-hydrogen para substituent; or when $R_1$ is halogen, n and o are 0, p is 1, $R_{12}$ and $R_{12}'$ are both hydrogen, $R_7$ is not halogen, and the compound is not N-(4-chlorophenyl)-2-(2-(4-chlorophenylamino)-2-oxoethoxy)benzamide;

2-(2-(4-bromophenylamino)-2-oxoethoxy)-N-(4-fluorophenyl)benzamide;

2-(2-(4-bromophenylamino)-2-oxoethoxy)-N-p-tolylbenzamide;

2-(2-(4-bromophenyl)amino)-2-oxoethoxy)-N-(4-methoxyphenyl)benzamide;

2-[2-[(4-bromophenyl)amino]-2-oxoethoxy]-N-[4-(difluoromethoxy)phenyl]-benzamide;

2-[2-[(4-bromophenyl)amino]-2-oxoethoxy]-N-[4-(trifluoromethyl)phenyl]-benzamide;

2-[2-[(4-bromophenyl)amino]-2-oxoethoxy]-N-(3,4-dimethoxyphenyl)-benzamide;

N-benzyl-2-(2-(4-bromophenylamino)-2-oxoethoxy)benzamide;

2-[2-[(4-iodophenyl)amino]-2-oxoethoxy]-N-(phenylmethyl)-benzamide;

2-[2-[(4-chlorophenyl)amino]-2-oxoethoxy]-N-(phenylmethyl)-benzamide;

N-benzyl-2-(2-(4-fluorophenylamino)-2-oxoethoxy)benzamide; 2-[2-[(4-bromophenyl)amino]-2-oxoethoxy]-N-[(4-methoxyphenyl)methyl]-benzamide;

2-[2-[(4-chloro-2-methylphenyl)amino]-2-oxoethoxy]-N-(phenylmethyl)-benzamide; or 2-[2-[(4-bromo-2-methylphenyl)amino]-2-oxoethoxy]-N-(phenylmethyl)-benzamide.

The following embodiments are also included in the disclosure:

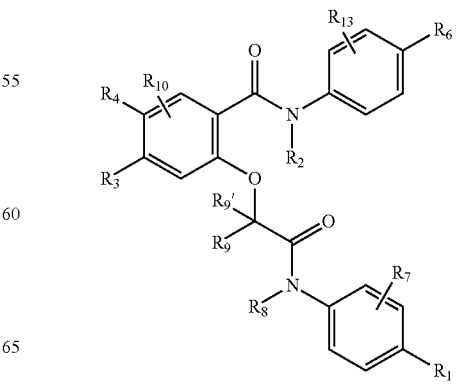

Formula (II)

-continued

Formula (III)

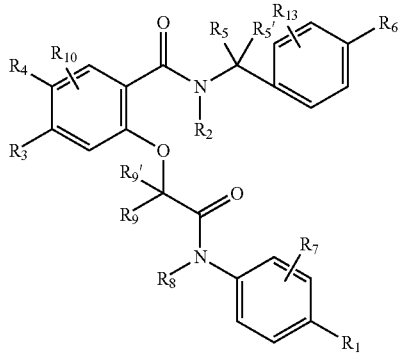

Formula (IV)

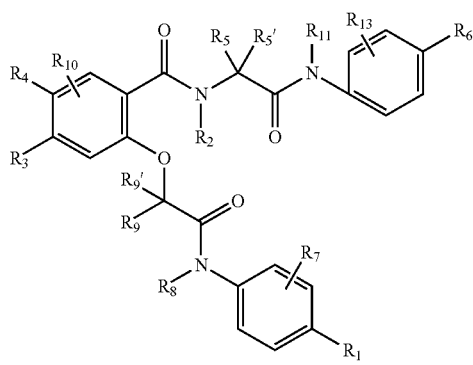

Formula (V)

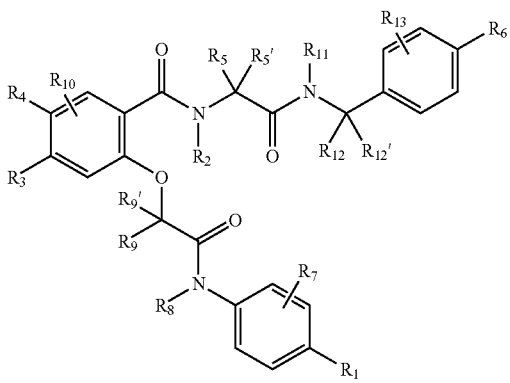

In each of Formula (I) to (V) the following conditions may apply.

(1) An embodiment in which m is 1;
$R_1$ is halogen;
$R_2$ is hydrogen or methyl;
$R_3$ and $R_4$ are independently hydrogen or methyl;
$R_6$ is halogen or trifluoromethyl;
$R_7$, $R_{10}$, and $R_{13}$ are each 0 substituents;
$R_8$ is hydrogen; and
$R_9$ and $R_9'$ are both hydrogen.

(2) An embodiment in which n, o, and p are all 0.

(3) An embodiment in which m is 1; n is 1;
$R_1$ is halogen;
$R_2$ is hydrogen or methyl;
$R_3$ and $R_4$ are independently hydrogen or methyl;
$R_5$ and $R_5'$ are independently hydrogen or methyl;
$R_6$ is hydrogen, halogen, $C_1$-$C_4$alkyl, $C_1$-$C_2$alkoxy, mono- or di-$C_1$-$C_2$alkylamino, or trifluoromethyl;
$R_7$, $R_{10}$, and $R_{13}$ are each 0 substitutents;
$R_8$ is hydrogen; and
$R_9$ and $R_9'$ are both hydrogen.

An embodiment in which p is 0.

An embodiment in which m is 1; n is 1; and o is 1;
$R_1$ is halogen;
$R_2$ is hydrogen;
$R_3$ and $R_4$ are independently hydrogen, halogen, or methyl;
$R_5$ and $R_5'$ are independently hydrogen or methyl;
$R_6$ is hydrogen, halogen, cyano, $C_1$-$C_6$alkyl, $C_1$-$C_2$alkoxy, mono- or di-$C_1$-$C_2$alkylamino, or trifluoromethyl;
$R_7$ is 0 or 1 halogen substituents;
$R_8$ is hydrogen;
$R_9$ is hydrogen or methyl;
$R_9'$ is hydrogen;
$R_{10}$ and $R_{13}$ are each 0 substituents; and
$R_{11}$ is hydrogen or methyl.

An embodiment in which p is 0;
$R_3$ and $R_4$ are both hydrogen;
$R_5$ is hydrogen or methyl;
$R_5'$ is hydrogen;
$R_6$ is hydrogen, halogen, cyano, $C_1$-$C_6$alkyl, $C_1$-$C_2$alkoxy, or mono- or di-$C_1$-$C_2$alkylamino;
$R_{10}$ and $R_{13}$ are each 0 substituents; and
$R_{11}$ is hydrogen.

An embodiment in which p is 0;
$R_3$ and $R_4$ are independently hydrogen or halogen;
$R_5$ is hydrogen or methyl;
$R_5'$ is hydrogen;
$R_6$ is hydrogen or halogen;
$R_7$, $R_{10}$, and $R_{13}$ are each 0 substituents; and
$R_{11}$ is methyl.

An embodiment in which $R_1$ is halogen or methyl;
$R_2$ is hydrogen;
$R_3$ and $R_4$ are independently hydrogen or methyl;
$R_5$ is hydrogen or methyl;
$R_5'$ is hydrogen;
$R_6$ is hydrogen, halogen, methyl, or methoxy;
$R_7$, $R_{10}$, and $R_{13}$ are each 0 substituents;
$R_8$ is hydrogen;
$R_9$ is hydrogen or methyl;
$R_9'$ is hydrogen;
$R_{11}$ is hydrogen or methyl; and
$R_{12}$ and $R_{12}'$ are both hydrogen.

An embodiment in which $R_1$ is halogen; and
$R_3$, $R_4$, $R_5$, $R_9$ and $R_{11}$ are all hydrogen.

An embodiment in which $R_1$ is halogen;
$R_3$ and $R_4$ are both hydrogen;
$R_5$ is hydrogen or methyl;
$R_6$ is hydrogen;
$R_9$ is hydrogen or methyl; and $R_{11}$ is methyl.

The disclosure also includes compounds and salts of Formula (II) in which:
$R_1$ is halogen;
$R_2$, $R_3$, $R_4$, $R_8$, and $R_9$ are each independently hydrogen or methyl;
$R_6$ is hydrogen, halogen, cyano, $C_1$-$C_6$alkyl, $C_1$-$C_2$alkoxy, or mono- or di-$C_1$-$C_2$alkylamino;
$R_7$ is 2,6-dimethyl;
$R_9'$ is hydrogen; and
$R_{10}$ and $R_{13}$ are 0 substituents.

The disclosure also includes compounds and salts of Formula (III) in which:
$R_1$ is halogen;
$R_2$, $R_3$, $R_4$, $R_5$, $R_8$, and $R_9$ are each independently hydrogen or methyl;

$R_5'$ and $R_9'$ are both hydrogen;

$R_6$ is hydrogen, halogen, cyano, $C_1$-$C_6$alkyl, $C_1$-$C_2$alkoxy, or mono- or di-$C_1$-$C_2$alkylamino;

$R_7$ is 2,6-dimethyl; and $R_{10}$ and $R_{13}$ are 0 substituents.

The disclosure further includes compounds and salts of Formula (IV) in which

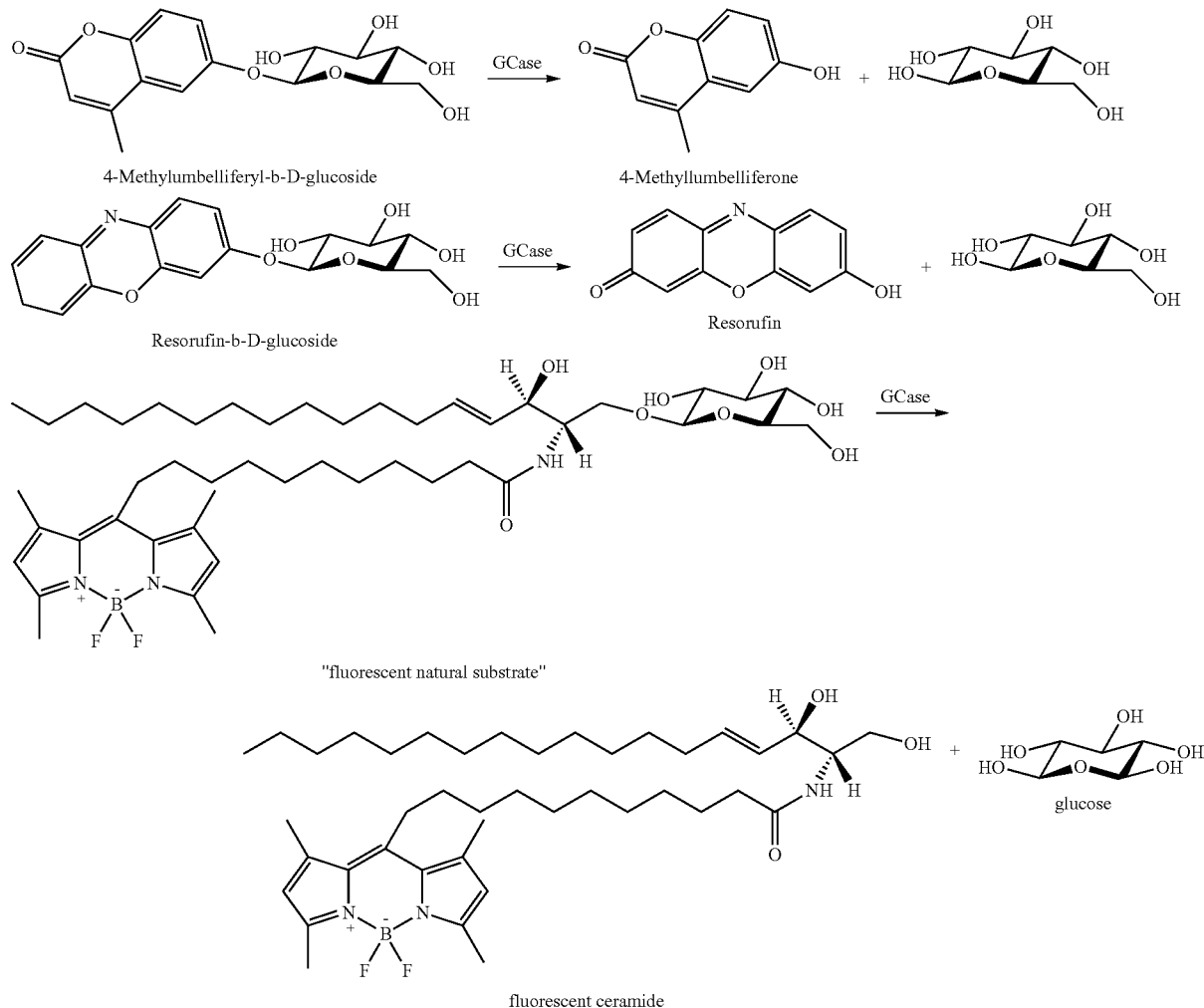

4-Methylumbelliferyl-b-D-glucoside

4-Methyllumbelliferone

Resorufin-b-D-glucoside

Resorufin

"fluorescent natural substrate"

fluorescent ceramide glucose $R_1$ is halogen;

$R_2$, $R_3$, $R_4$, $R_5$, $R_8$, $R_9$, and $R_{11}$ are each independently hydrogen or methyl;

$R_5'$ and $R_9'$ are both hydrogen;

$R_6$ is hydrogen, halogen, cyano, $C_1$-$C_6$alkyl, $C_1$-$C_2$alkoxy, or mono- or di-$C_1$-$C_2$alkylamino;

$R_7$ is 2,6-dimethyl; and $R_{10}$ and $R_{13}$ are 0 substituents.

The disclosure also includes compounds and salts of Formula (V) in which:

$R_2$, $R_3$, $R_4$, $R_5$, $R_8$, $R_9$, $R_{11}$ and $R_{12}$ are each independently hydrogen or methyl;

$R_5'$, $R_9'$, and $R_{12}'$ are all hydrogen;

$R_6$ is hydrogen, halogen, cyano, $C_1$-$C_6$alkyl, $C_1$-$C_2$alkoxy, or mono- or di-$C_1$-$C_2$alkylamino;

$R_7$ is 2,6-dimethyl; and $R_{10}$ and $R_{13}$ are 0 substituents.

Any combination of the above variable definitions that results in a stable compound of Formula (I) to (V) is included in the disclosure. Any of the compounds or generic formulae discussed in this application may be used in the methods of treatment discussed in this application.

Biological Description

Glucocerebrosidase (GCase) catalyzes the following reactions:

The primary screening assay and many of the secondary assays are based on a fluorescent read-out and are direct enzymatic assays that measure GCase specific activity. Three different substrates are used: 4-methylumbelliferyl-β-D-glucoside (Ex365/Em440), resorufin-β-D-glucoside (Ex573/Em590) and BODIPY tagged glucosylceramide (Ex505/Em540). Furthermore, four different sources of GCase are used for these assays; the N370S mutant (the most common mutation) and wildtype GCase, both from either tissue homogenate or purified recombinant enzyme. Table 1 shows a general protocol that was used for these assays, and the details have also previously been published in PubChem linked to the summary AID 2593.

There is some discrepancy in activity observed in assays that used the purified enzyme versus the spleen homogenate potentially due to the presence of additional activating factors in the tissue. For instance, GCase activity is modulated in cells through the binding of the allosteric activator Saposin C. In the GCase enzyme assay with purified enzyme, the addition of sodium taurocholate, a bile salt, is required to activate the enzyme. It can be speculated that the variation in inhibitory activity between isolated enzyme and tissue homogenate is due to the differences between the active GCase conformation induced by detergent and the one induced by Saposin C and/or other factors in cells. These conformational differences might also explain why a chemical series with the capacity to activate and not inhibit the enzyme has not been previously found via conventional purified-enzyme screening assays. It may be that a detergent like sodium taurocholate induces a conformation that activates enzyme turnover to a maximum, and thus, further activation by a small molecule simply cannot be observed. In contrast, tissue homogenate conditions do not require the use of additional activating components, because natural activators like Saposin C are already present in the homogenate; thus, these conditions might provide a more faithful representation of the actual cellular activity.

TABLE 1

General protocol for primary and secondary assays.

| Step | Parameter | Value | Description |
|---|---|---|---|
| 1 | Reagent | 2 μL | Enzyme |
| 2 | Compound | 23 nL | 0.5 nM to 58 μM final concentrations (in titration) |
| 3 | Reagent | 2 μL | Substrate |
| 4 | Time | 40 min | 37° C. incubation |
| 5 | Reagent | 2 μL | Stop solution (1M NaOH and 1M Glycine mixture, pH 10) |
| 6 | Detector | Luminescence/ fluorescence | ViewLux plate reader |

Treatment Methods

The compounds of Formula (I) or a salt thereof, as well as pharmaceutical compositions comprising the compounds, are useful for treating lysosomal storage diseases, including Gaucher disease. The compounds of Formula (I) or a salt thereof, as well as pharmaceutical compositions comprising the compounds, are also useful for preventing the occurrence of symptoms of a lysosomal storage disorder, such as Gaucher disease, in a patient having GBA gene mutation. The method of treating a lysosomal storage disease in a patient comprises providing to the patient an effective amount of a compound or salt of Formula (I): In an embodiment the patient is a mammal, specifically a primate, more specifically a human. An effective amount of a pharmaceutical composition may be an amount sufficient to inhibit the progression of a disease or disorder; or cause a regression of a disease or disorder.

An effective amount of a compound or pharmaceutical composition described herein will also provide a sufficient concentration of a compound or salt of Formula (I) compound when administered to a patient. A sufficient concentration is a concentration of the compound or salt of Formula (I) in the patient's body necessary to prevent or combat the disorder. Such an amount may be ascertained experimentally, for example by assaying blood concentration of the compound, or theoretically, by calculating bioavailability.

Treatment methods include testing a patient for a GBA gene mutation, determining that the patient carries at least one GBA gene mutation in each of their two copies of the GBA gene, and administering compound or salt of Formula (I) the patient. Treatment also includes testing a non-pediatric patient for a GBA gene mutation, determining that the patient carries at least one GBA gene mutation in at least one of their two copies of the GBA gene, determining the patient is at risk for developing Parkinson's disease, and administering an effective amount of a compound or salt of Formula (I) to the patient.

Treatment methods also include a method of treating Parkinson's disease in a patient comprising administering an effective amount of a compound or salt of Formula (I) to the patient. An "effective amount" of a compound of Formula (I) in the context of Parkinson's disease may be enough to lessen the severity of symptoms the patient is experiencing or prevent an increase in severity of symptoms in the patient. Treatment methods in the context of Parkinson's disease also include prophylactic treatment of a patient at risk for Parkinson's disease with a compound or slat of Formula (I).

Treatment methods also include a method of treating dementia with Lewy bodies comprising administering an effective amount of a compound of or salt of Formula (I) to a patient who displays symptoms of dementia with Lewy bodies or who is at risk for dementia with Lewy bodies due to being shown to have at least on copy of a mutated GBA gene.

Methods of treatment further include administering an amount of a compound or salt of Formula (I) to a patient sufficient to increase the amount of beta gluococerebrosidease in the white blood cells of the patient. Embodiments in which the patient has a GBA gene mutation are particularly included. GBA gene mutations include N370S, 84GG, V394L, and R496H, though more than 200 GBA mutations have been identified.

The disclosure also includes a method of enhancing the activity of a lysomal glucocerebrosidase enzyme, in vivo or in vitro, comprising contacting the enzyme, or a mammalian cell comprising the enzyme in vivo or in vitro with a sufficient amount of a compound or salt of Formula (I) to increase the activity of the glucocerebrosidase enzyme.

Methods of treatment include providing certain dosage amounts of a salicyclic acid derivative of Formula (I) or salt thereof to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula (I) are provided daily to a patient. Frequency of dosage may also vary. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

In an embodiment, the invention provides a method of treating a lysosomal storage disorder in a patient identified as in need of such treatment, the method comprising providing to the patient an effective amount of a compound of Formula (I). The compounds and salts of Formula (I)

provided herein may be administered alone, or in combination with one or more other active agent.

EXAMPLES

Abbreviations

DCM Dichloromethane
DMF Dimethylformamide
TEA Triethylacetate
THF Tetrahydrofuran General Methods The reagents and solvents used were commercial anhydrous grade. They were used without further purification. Column chromatography was carried out over silica gel (100-200 mesh). $^1$H- and $^{13}$C NMR spectra were recorded on a Bruker 400 MHz spectrometer from solutions in CDCl$_3$ and DMSO-d6. Automated preparative reverse-phase HPLC purification was performed using an Agilent 1200 Mass-Directed Fractionation system (prep pump G1361 with gradient extension, make-up pump G1311A, pH modification pump G1311A, HTS PAL autosampler, UV-DAD detection G1315D, Fraction Collector G1364B, and Agilent 6120 quadrapole spectrometer G6120A). The preparative chromatography conditions included a Waters X-Bridge C18 column (19×150 mm, 5um, w/19×10 mm guard column), elution with a water and CH$_3$CN gradient, which increases 20% in CH$_3$CN content over 4 minutes at a flow rate of 20 mL/min (modified to pH 9.8 through addition of NH$_4$OH by auxiliary pump), and sample dilution in DMSO. The preparative gradient, triggering thresholds, and UV wavelength were selected based on the analytical-scale HPLC analysis of each crude sample. The analytical method employed a Waters Acquity system with UV detection and mass detection (Waters LCT Premier). The analytical method conditions included a Waters Aquity BEH C18 column (2.1×50 mm, 1.7 um) and elution with a linear gradient of 5% CH$_3$CN in pH 9.8 buffered aqueous NH$_4$OH to 100% CH$_3$CN at 0.6 mL/min flow rate. The purity was determined using UV peak area at 214 nm.

Example 1

Synthesis of 2-(2-((4-bromophenyl)amino)-2-oxoethoxy)-N-(2-(methyl(phenyl)amino)-2-oxoethyl)benzamide (ML266)

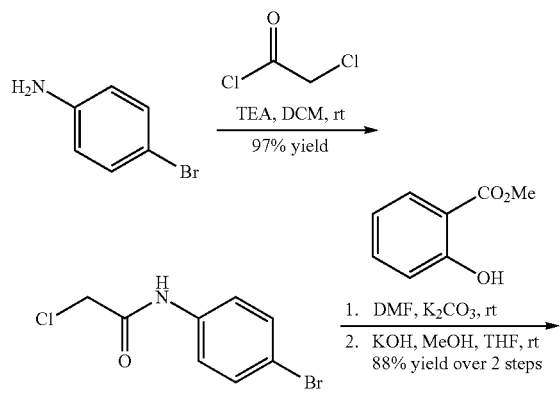

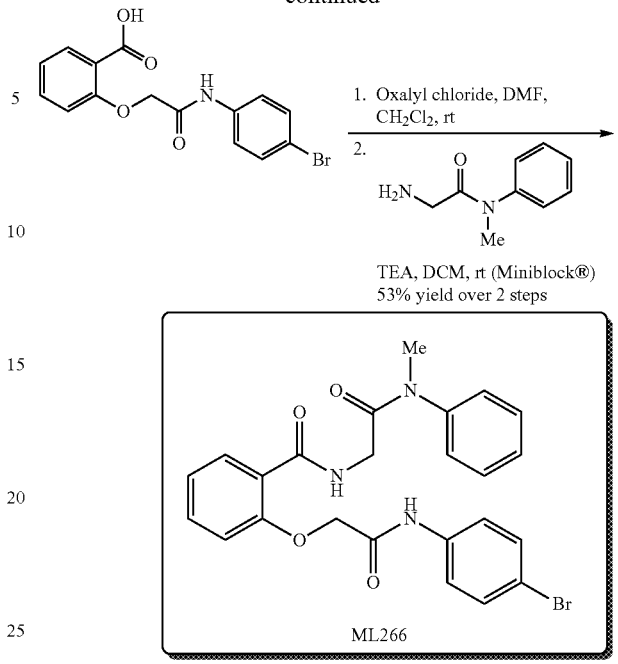

Step 1: Preparation of N-(4-bromophenyl)-2-chloroacetamide

4-Bromoaniline (4.12 g, 23.95 mmol) was dissolved in 50 mL of dichloromethane in a round bottomed flask containing a stir bar. While stirring, triethylamine (2.91 g, 28.74 mmol) was added to the reaction mixture and then cooled to 0° C. 2-Chloroacetyl chloride (2.71 g, 23.95 mmol) was added dropwise to the reaction mixture, which was then allowed to slowly warm to room temperature and stir for 16 hours. The reaction mixture was diluted with 100 mL of dichloromethane, washed twice with 1N HCl, run through a silica gel plug, and then concentrated in vacuo to give N-(4-bromophenyl)-2-chloroacetamide (5.74 g, 97% yield).

Step 2: Preparation of 2-(2-((4-bromophenyl)amino)-2-oxoethoxy)benzoate

Potassium carbonate (3.75 g, 27.1 mmol) was added to a mixture of N-(4-bromophenyl)-2-chloroacetamide (2.25 g, 9.05 mmol) and methyl 2-hydroxybenzoate (1.38 g, 9.05 mmol) in DMF (30 mL). The reaction mixture was stirred for 16 hours. 1 N HCl was added slowly to the reaction mixture. The combined solution was extracted three times with ethyl acetate. The resulting organic layer was washed twice with water, once with brine, run through a silica plug, and then concentrated in vacuo to give methyl 2-(2-((4-bromophenyl)amino)-2-oxoethoxy)benzoate (3.11 g, 94% yield).

Step 3: Preparation of 2-(2-((4-bromophenyl)amino)-2-oxoethoxy)benzoic acid

Methyl 2-(2-((4-bromophenyl)amino)-2-oxoethoxy)benzoate was dissolved in a mixture of tetrahydrofuran and methanol (2:1). Potassium hydroxide (0.82 g, 14.55 mmol) was dissolved in 5 mL of water and then added to the reaction mixture. This mixture was then allowed to stir for 16 hours. Water was added. The aqueous solution was then extracted with diethyl ether, and the organic phase was discarded. The aqueous phase was then placed in a round bottomed flask with a stir bar, cooled in an ice bath, and then the pH was adjusted to approximately 3. A precipitate resulted that was immediately filtered off and dried to give 2-(2-((4-bromophenyl)amino)-2-oxoethoxy)benzoic acid (0.96 g, 94% yield).

Step 4: Final Product 2-(2-((4-Bromophenyl)amino)-2-oxoethoxy)benzoic acid (0.19 g, 0.55 mmol) was dissolved in 10 mL of dichloromethane in a round bottomed flask containing a stir bar. N,N-dimethylformamide (0.04 g, 0.549 mmol) was added to this stirring mixture, and then the mixture was cooled to 0° C. A solution of oxalyl chloride (0.209 g, 1.65 mmol) in 3 mL of dichloromethane was added dropwise. The reaction was allowed to slowly warm to room temperature and then to further mix for one hour. The reaction was concentrated in vacuo to remove solvent and excess oxalyl chloride, while not heating over 30° C. This crude mixture was then redissolved in 2 mL of dichloromethane and added dropwise to a solution of 2-amino-N-methyl-N-phenylacetamide (0.12 g, 0.60 mmol), triethylamine (0.12 g, 1.21 mmol) in dichloromethane (2 mL) that had been previously placed in Metier-Toledo Bohdan Miniblock™ reaction tube (Metier-Toledo Autochem Reaction tubes 10.0 mi Part #1352118) (Note: 6×4 Miniblock™ setups were used to generate 24 different products per block in parallel). After the addition, the septum layer and cover plate were secured onto the Miniblock™ with spring clamps. The block was then secured onto a Bohdan Miniblock™ Compact Shaking and Washing Station, in which the shaker was set at 600 rpm for 16 hours. The Miniblock™ was then removed from the shaker, followed by a subsequent draining of the reaction mixture into a second Miniblock™ containing a Biotage ISOLUTE® SPE Accessories Phase Separator Tube (Part #120-1905-CG), containing a 1N HCl solution (3 mL) A cover plate was placed on the second Miniblock™ containing the reaction mixture, and then the Miniblock™ was placed on the shaker and was allowed to shake for five minutes at 600 rpm. After removal of the Miniblock™ from the shaker, the organic phase was allowed to drain into a sample collection tube. Sample was concentrated in vacuo in a GeneVac HT-4X centrifugal evaporator and then purified via automated preparative reverse-phase HPLC purification (Method listed below) to give 2-(2-(4-bromophenyl)amino)-2-oxoethoxy)-N-(2-(methyl(phenyl)amino)-2-oxoethyl) benzamide (0.15 g, 43% yield).

Example 2

Additional Compounds

The following compounds are made by the method set forth in Example 1. Those of skill in the art of organic synthesis will recognize routine changes in starting materials and reaction conditions necessary to produce the compounds shown in TABLE 2.

TABLE 2

| Cpd. No. | Structure | Name | Analytical Data |
| --- | --- | --- | --- |
| 1 | 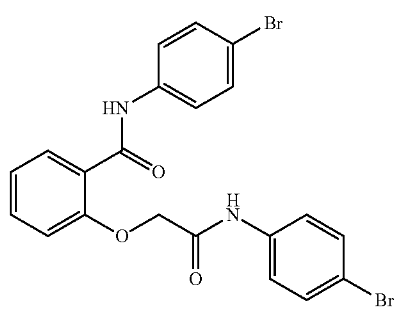 [SMILES: O=C(COc1ccccc1C(=O)Nc1ccc(Br)cc1)Nc1ccc(Br)cc1] | N-(4-bromophenyl)-2-(2-(4-bromophenyl amino)-2-oxoethoxy) benzamide (CID-46926406) | $^1$H NMR (400 MHz, DMSO) δ 10.63 (s, 1H), 10.47 (s, 1H), 7.81 (m, 3H), 7.60 (m, 2H), 7.56 (m, 5H), 7.21 (d, J = 8.0 Hz, 1H), 7.14 (td, J = 0.8, 7.6 Hz, 1H) ppm; $^{13}$C NMR (100 MHz, DMSO) δ 166.93, 164.3, 155.3, 138.3, 137.5, 132.8, 131.7, 131.6, 130.5, 124.0, 11.8, 121.3, 115.5, 115.4, 113.8, 103.7, 102,5. 67.8 ppm; HRMS calcd for $C_{21}H_{16}Br_2N_2O_3$ [M + H$^+$] 502.9600, found 502.9610 |
| 2 | 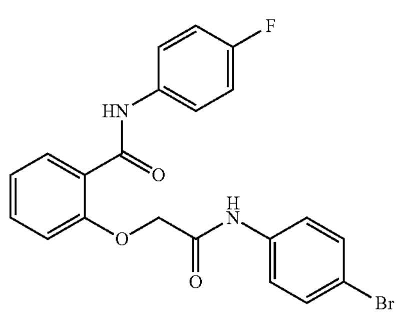 | 2-(2-(4-bromophenylamino)-2-oxoethoxy)-N-(4-fluorophenyl) benzamide (CID-36294275) | $^1$H NMR (400 MHz, DMSO) δ 10.72 (s, 1H), 10.51 (s, 1H), 7.83 (m, 3H), 7.62, (d, J = 5.2 Hz, 2H), 7.54 (m, 3H), 7.24-7.14 (m, 4H), 4.99 (s, 2H) ppm; $^{13}$C NMR (100 MHz, DMSO) δ 166.9, 164.1, 157.3, 155.3. 137.6, 135.3, 132.8, 131.7, 130.4, 124.1, 121.7, 121.6, 121.3, 115.4, 115.3, 113.8, 67.8, 30.7 ppm; HRMS calcd for $C_{21}H_{16}BrFN_2O_3$ [M + H$^+$] 443.0401, found 443.0401 |

TABLE 2-continued

| Cpd. No. | Structure | Name | Analytical Data |
|---|---|---|---|
| 3 | 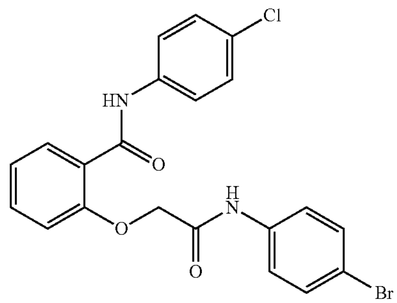 [SMILES: O=C(COc1ccccc1C(=O)Nc1ccc(Cl)cc1)Nc1ccc(Br)cc1] | 2-(2-(4-bromophenylamino)-2-oxoethoxy)-N-(4-chlorophenyl)benzamide (CID-46926395) | $^1$H NMR (400 MHz, DMSO) δ 10.79 (s, 1H), 10.49 (s, 1H), 7.87 (d, J = 4.8 Hz, 2H), 7.83 (dd, J = 6.0, 1.6 Hz, 1H), 7.61 (d, J = 4.8 Hz, 2H), 7.56 (m, 3H), 7.44 (d, (J = 4.8 Hz, 2H), 7.23 (d, J = 8 Hz, 1H), 7.15 (td, J = 0.8, 7.2 Hz, 1H), 4.99 (s, 2H) ppm; $^{13}$C NMR (100 MHz, DMSO) δ 166.9, 164.3, 155.3, 137.9, 137.5, 132.9, 131.7, 130.5, 128.7, 127.3, 124.0, 121.8, 121.4, 121.3, 115.5, 113.8, 67.8, 30.7 ppm; HRMS calcd for $C_{21}H_{16}BrClN_2O_3$ [M + H$^+$] 459.0106, found 459.0104 |
| 4 | 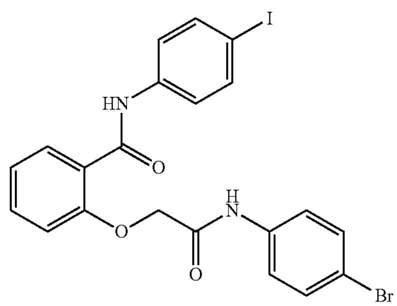 | 2-(2-(4-bromophenyl amino)-2-oxoethoxy)-N-(4-iodophenyl)benzamide (CID-46926377) | $^1$H NMR (400 MHz, DMSO) δ 10.75 (s, 1H), 10.48 (s, 1H), 7.82 (dd, J = 2.8, 5.6 Hz, 1H), 7.71 (m, 4H), 7.60 (m, 2H), 7.56 (m, 3H), 7.20 (d, J = 8 Hz, 1H), 7.14 (td, J = 0.8, 8.0 Hz, 1H), 4.99 (s, 2H) ppm; $^{13}$C NMR (100 MHz, DMSO) δ 166.9, 164.3, 155.3, 138.8, 137.5, 137.4, 132.9, 131.7, 130.5, 124.0, 122.0, 121.8, 121.3, 115.5, 113.8, 87.4, 67.8 ppm; HRMS calcd for $C_{21}H_{16}BrIN_2O_3$ [M + H$^+$] 550.9462, found 550.9462 |
| 5 | 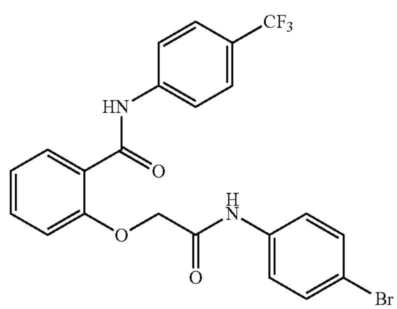 | 2-(2-(4-bromophenylamino)-2-oxoethoxy)-N-(4-trifluoromethyl)phenyl)benzamide (CID-2459634) | $^1$H NMR (400 MHz, DMSO) δ 10.98 (s, 1H), 10.47 (s, 1H), 8.06 (d, J = 8.4 Hz, 2H), 7.85 (dd, J = 2.0, 6.0 Hz, 1H), 7.75 (d, J = 8.4 Hz, 2H), 7.63-7.52 (m, 5H), 7.22 (d, J = 8.0 Hz, 1H), 7.18 (td, J = 0.8, 6.8 Hz, 1H), 5.01 (s, 2H) ppm; $^{13}$C NMR (100 MHz, DMSO) δ 166.9, 164.6, 155.3, 142.5, 137.5, 133.1, 131.7, 130.6, 126.1, 125.4, 123.8, 123.5, 123.3, 121.8, 121.3, 119.7, 115.5, 113.8, 67.8 ppm; HRMS calcd for $C_{22}H_{16}BrF_3N_2O_3$ [M + H$^+$] 493.0369, found 493.0373 |
| 6 | 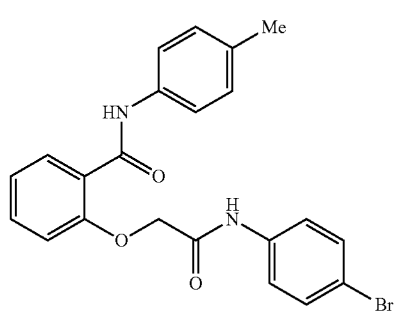 | 2-(2-(4-bromophenylamino)-2-oxoethoxy)-N-p-tolylbenzamide (CID-46926376) | $^1$H NMR (400 MHz, DMSO) δ 10.59 (s, 1H), 10.52 (s, 1H), 7.82 (dd, J = 1.6, 6.0 Hz, 1H), 7.72 (d, J = 8.8 Hz, 2H), 7.63 (d, J = 7.2 Hz, 2H), 7.56 (m, 3H), 7.23 (d, J = 8.0 Hz, 1H), 7.16 (d, J = 8.0 Hz, 3H), 4.99 (s, 2H), 2.25 (s, 3H) ppm; $^{13}$C NMR (100 MHz, DMSO) δ 166.9, 163.9, 155.2, 137.6, 136.4, 132.7, 132.6, 131.7, 130.4, 129.1, 124.4, 121.7, 121.3, 119.8, 115.5, 113.8, 67.8, 20.5 ppm; HRMS calcd for $C_{22}H_{19}BrN_2O_3$ [M + H$^+$] 439.0652, found 439.0655 |

TABLE 2-continued

| Cpd. No. | Structure | Name | Analytical Data |
|---|---|---|---|
| 7 | 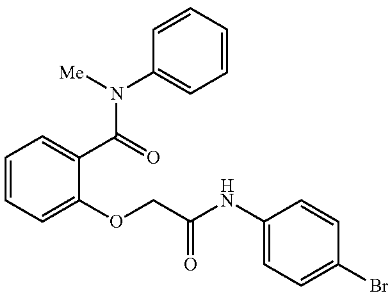 [SMILES: CN(C(=O)c1ccccc1OCC(=O)Nc1ccc(Br)cc1)c1ccccc1] | 2-(2-((4-bromophenyl)amino)-2-oxoethoxy)-N-methyl-N-phenylbenzamide (CID-31528970) | $^1$H NMR (400 MHz, DMSO) δ 10.32 (s, 1H), 7.69 (d, J = 7.6 Hz, 2H), 7.54 (d, J = 8.8 Hz, 2H), 7.20 (bs, 6H), 7.01 (bs, 2H), 6.77 (bs, 1H), 4.74 (s, 2H), 3.42 (s, 3H) ppm; ; $^{13}$C NMR (100 MHz, DMSO) δ 168.2, 166.9, 154.1, 137.7, 131.7, 130.4, 128.8, 128.4, 126.8, 126.6, 126.5, 121.2, 121.0, 115.4, 112.9, 67.5, 36.8 ppm; HRMS calcd for C$_{22}$H$_{19}$BrN$_2$O$_3$ [M + H$^+$] 439.0652, found 439.0656. |
| 8 | 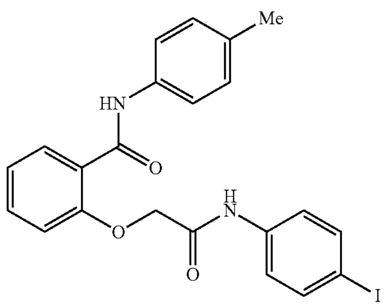 | 2-(2-((4-iodophneyl)amino)-2-oxoethoxy)-N-(p-tolyl)benzamide | |
| 9 | 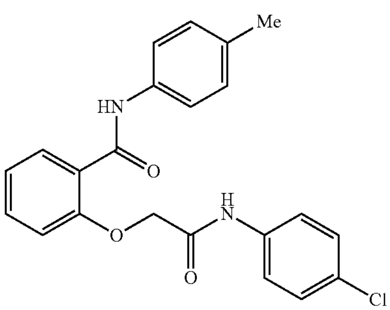 | 2-(2-(4-chlorophenylamino)-2-oxoethoxy)-N-p-tolylbenzamide (CID-46926407) | $^1$H NMR (400 MHz, DMSO) δ 10.59 (s, 1H), 10.53 (s, 1H), 7.83 (dd, J = 2.0, 5.6 Hz, 1H) 7.72 (d, J = 8.4 Hz, 2H), 7.69 (d, J = 8.4 Hz, 2H), 7.55 (td, J = 2.0, 6.4 Hz, 1H), 7.41 (d, J = 8.0 Hz, 2H), 7.23 (d, J = 8.0 Hz, 1H), 7.16 (d, J = 10.9 Hz, 2H), 4.98 (s, 2H), 2.28 (s, 3H) ppm; $^{13}$C NMR (100 MHz, DMSO) δ 166.9, 164.0, 155.2, 137.2, 136.4, 132.7, 132.6, 130.4, 129.1, 128.8, 124.4, 121.7, 120.9, 119.8, 113.8, 67.7, 20.46 ppm; HRMS calcd for C$_{22}$H$_{19}$ClN$_2$O$_3$ [M + H$^+$] 395.1157, found 395.1156 |
| 10 | 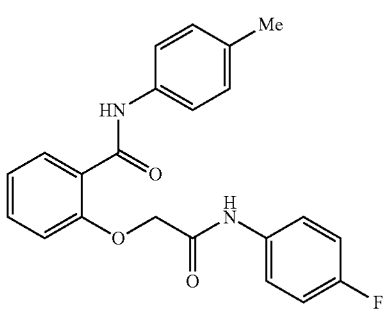 | 2-(2-(4-fluorophenylamino)-2-oxoethoxy)-N-p-tolylbenzamide (CID-46926400) | $^1$H NMR (400 MHz, DMSO) δ 10.44 (s, 1H), 10.22 (s, 1H), 7.83 (dd, J = 2.0, 6.0 Hz, 1H), 7.23 (d, J = 8.4 Hz, 2H), 7.66 (m, 2H), 7.56 (td, 1.6, 7.2 Hz, 1H), 7.17 (m, 6H), 4.98 (s, 2H), 2.28 (s, 3H) ppm; $^{13}$C NMR (100 MHz, DMSO) δ 166.7, 163.9, 155.2, 136.4, 134.6, 132.7, 132.6, 130.4, 129.1, 124.4, 121.7, 121.1, 119.8, 115.6, 113.8, 67.0, 20.5 ppm; HRMS calcd for C$_{22}$H$_{19}$FN$_2$O$_3$ [M + H$^+$] 379.1452, found 379.1452 |

TABLE 2-continued

| Cpd. No. | Structure | Name | Analytical Data |
|---|---|---|---|
| 11 | 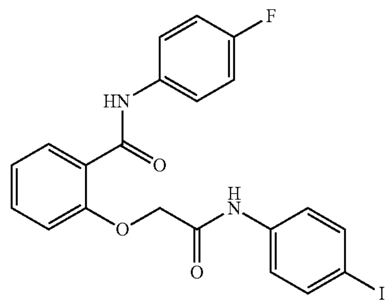 [SMILES: O=C(COc1ccccc1C(=O)Nc1ccc(F)cc1)Nc1ccc(I)cc1] | N-(4-fluorophenyl)-2-(2-(4-iodophenylamino)-2-oxoethoxy)benzamide (CID-46926373) | $^1$H NMR (400 MHz, DMSO) δ 10.71 (s, 1H), 10.46 (s, 1H), 7.85 (m, 3H), 7.69 (d, J = 4.8Hz, 2H), 7.57 (td, J = 1.6, 5.6 Hz, 1H), 7.50 (d, J = 4.8Hz, 2H), 7.24-7.14 (m, 4H), 4.98 (s, 2H) ppm; $^{13}$C NMR (100 MHz, DMSO) δ 166.9, 164.21, 159.2, 155.3, 138.0, 137.6, 135.3, 132.8, 130.4, 124.1, 121.7, 121.5, 121.4, 115.4, 115.3, 113.8, 87.5, 67.8 ppm; HRMS calcd for $C_{21}H_{16}FIN_2O_3$ [M + H$^+$] 491.0262, found 491.0257 |
| 12 | 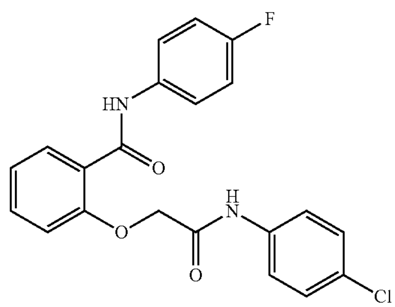 | 2-(2-(4-chlorophenylamino)-2-oxoethoxy)-N-(4-fluorophenyl)benzamide (CID-46943205) | $^1$H NMR (400 MHz, DMSO) δ 10.72 (s, 1H), 10.51 (s, 1H), 7.86 (m, 3H), 7.68 (d, J = 4.0 Hz, 2H), 7.60-7.46 (m, 3H), 7.41, (d, J = 4.0 Hz, 2H), 7.23 (d, J = 7.2 Hz, 2 H), 7.15 (m, 2H), 4.99 (s, 2H) ppm; $^{13}$C NMR (100 MHz, DMSO) δ 166.9, 164.9, 160.9, 159.7, 157.5, 155.3, 140.4, 139.7, 138.2, 135.5, 134.8, 134.2, 131.7, 130.4, 129.5, 128.9, 127.7, 124.2, 122.0, 121.5, 114.5, 67.7 ppm; HRMS calcd for $C_{21}H_{16}ClFN_2O_3$ [M + H$^+$] 399.0906, found 399.0898 |
| 13 | 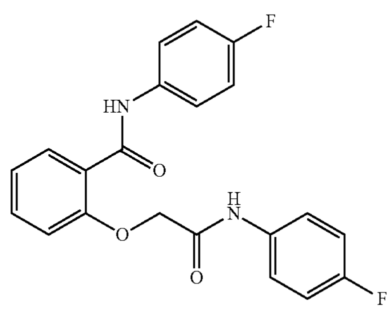 [SMILES: O=C(COc1ccccc1C(=O)Nc1ccc(F)cc1)Nc1ccc(F)cc1] | N-(4-fluorophenyl)-2-(2-(4-fluorophenyl amino)-2-oxoethoxy)benzamide (CID-46943209) | $^1$H NMR (400 MHz, DMSO) δ 10.74 (s, 1H), 10.44 (s, 1H), 7.86 (m, 2H), 7.83 (dd, J = 1.2, 4.8 Hz, 1H), 7.66 (m, 2H), 7.56 (dt, J = 1.2, 5.6 Hz, 1H), 7.21 (m, 6H), 4.99 (s, 2H) ppm; $^{13}$C NMR (100 MHz, DMSO) δ 166.7, 164.1, 159.2, 157.3, 157.2, 155.3, 135.4, 135.3, 134.6, 134.6, 132.7, 130.5, 124.2, 121.7, 121.6, 121.2, 121.1, 115.6, 115.4, 115.3, 113.8, 67.7 ppm; HRMS calcd for $C_{21}H_{16}F_2N_2O_3$ [M + H$^+$] 383.1197, found 383.1202 |
| 14 | 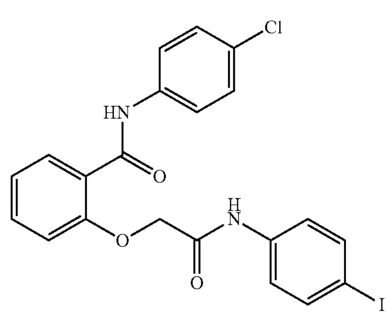 | N-(4-chlorophenyl)-2-(2-(4-iodophenylamino)-2-oxoethoxy)benzamide (CID-46926398) | $^1$H NMR (400 MHz, DMSO) δ 10.77 (s, 1H), 10.44 (s, 1H), 7.86 (d, J = 4.8 Hz, 2H), 7.83 (dd, J = 2.0, 6.0 Hz, 1H), 7.69 (d, J = 5.2 Hz, 2H), 7.58 (td, J = 1.6, 5.6 Hz, 1H), 7.49 (d, J = 4.8 Hz, 2H), 7.44 (d, J = 5.6 Hz, 2H), 7.22 (d, J = 8.0Hz, 2H), 7.14 (td, J = 0.8, 7.6 Hz, 1H), 4.98 (s, 2H) ppm; $^{13}$C NMR (100 MHz, DMSO) δ 166.9, 164.3, 155.3, 137.9, 137.8, 137.6, 132.9, 130.5, 128.7, 127.3, 124.0, 121.7, 121.5, 121.4, 113.8, 87.5, 67.8 ppm; HRMS calcd for $C_{21}H_{16}ClIN_2O_3$ [M + H$^+$] 506.9963, found 506.9963 |

TABLE 2-continued

| Cpd. No. | Structure | Name | Analytical Data |
|---|---|---|---|
| 15 | 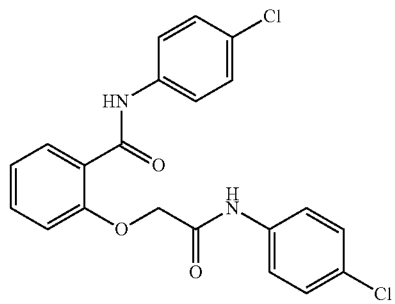 [SMILES: O=C(COc1ccccc1C(=O)Nc1ccc(Cl)cc1)Nc1ccc(Cl)cc1] | N-(4-chloro phenyl)-2-(2-(4-chlorophenylamino)-2-oxoethoxy)benzamide (CID-46943218) | $^1$H NMR (400 MHz, DMSO) δ 10.79 (s, 1H), 10.49 (s, 1H), 7.88 (d, J = 7.2 Hz, 2H), 7.83 (dd, J = 1.2, 4.8 Hz, 1H), 7.68 (d, J = 7.2 Hz, 2H), 7.58 (td, J = 1.2, 5.6 Hz, 1H), 7.42 (t, J = 5.6 Hz, 4H), 7.21 (d, J = 6.8 Hz, 1H), 7.17 (t, J = 5.6 Hz, 1H), 4.99 (s, 2H) ppm; $^{13}$C NMR (100 MHz, DMSO) δ 166.9, 164.3, 155.3, 137.9, 137.2, 132.9, 130.5, 128.8, 128.7, 127.4, 127.3, 124.0, 121.8, 121.4, 120.8, 113.8, 67.7 ppm; HRMS calcd for $C_{21}H_{16}Cl_2N_2O_3$ [M + H$^+$] 415.0611, found 415.0605 |
| 16 | 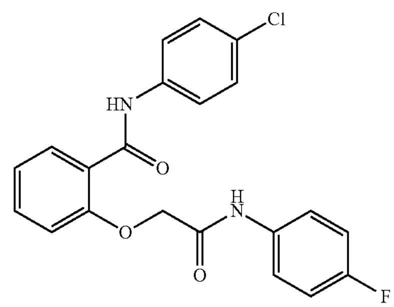 [SMILES: O=C(COc1ccccc1C(=O)Nc1ccc(Cl)cc1)Nc1ccc(F)cc1] | N-(4-chlorophenyl)-2-(2-(4-fluoropheny lamino)-2-oxoethoxy)benzamide (CID-46926391) | $^1$H NMR (400 MHz, DMSO) δ 10.78 (s, 1H), 10.41 (s, 1H), 7.88 (d, J = 6.8 Hz, 2H), 7.83 (dd, J = 1.6, 6.0 Hz, 1H), 7.65 (m, 2H), 7.58 (2.0, 5.6 Hz, 1H), 7.43 (d, J = 4.4 Hz, 2H), 7.18 (m, 4H), 4.98 (s, 2H) ppm; $^{13}$C NMR (100 MHz, DMSO) δ 166.7, 164.3, 159.2, 157.3, 155.3, 137.9, 134.6, 132.9, 130.5, 128.7, 127.3, 124.1, 121.8, 121.2, 115.6, 115.4, 113.8, 67.7 ppm; HRMS calcd for $C_{21}H_{16}ClN_2O_3$ [M + H$^+$] 399.0906, found 399.0906 |
| 16a | 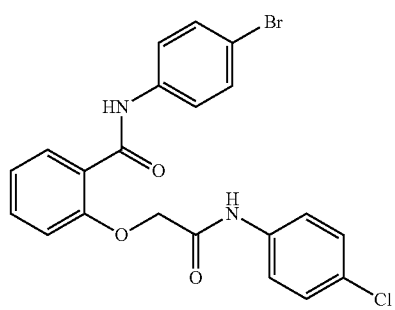 | N-(4-bromophenyl)-2-(2-(4-chlorophenylamino)-2-oxoethoxy)benzamide (CID-46926382) | $^1$H NMR (400 MHz, DMSO) δ 10.78 (s, 1H), 10.49 (s, 1H), 7.81 (d, J = 7.2 Hz, 3H), 7.66 (d, J = 8.8 Hz, 2H), 7.56 (d, J = 8.8 Hz, 3H), 7.42 (d, J = 8.8 Hz, 2H), 7.23 (d, J = 8.0 Hz, 1H), 7.15 (td (J = 0.8, 7.2 Hz, 1H), 4.99 (s, 2H) ppm; $^{13}$C NMR (100 MHz, DMSO) δ 166.9, 164.3, 155.3, 138.3, 137.1, 132.9, 131.6, 130.5, 128.8, 127.4, 124.0, 121.8, 120.9, 115.4, 113.8, 67.7 ppm; HRMS calcd for $C_{21}H_{16}BrClN_2O_3$ [M + H$^+$] 459.0106, found 459.0093 |
| 17 | 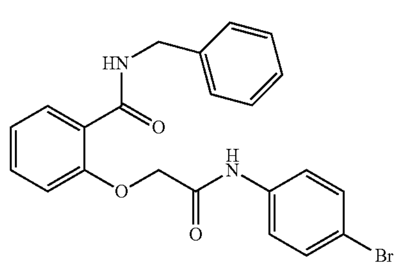 [SMILES: O=C(COc1ccccc1C(=O)NCc1ccccc1)Nc1ccc(Br)cc1] | N-benzyl-2-(2-(4-bromophenyl-amino)-2-oxoethoxy)benzamide (CID-24382054) | $^1$H NMR (400 MHz, DMSO) δ 10.66 (s, 1H), 9.30 (t, J = 6.0 Hz, 1H), 7.72 (dd, J = 2.0, 5.6 Hz, 1H), 7.62 (d, J = 4.8 Hz, 2H), 7.49 (d, J = 4.8 Hz, 3H), 7.37 (d, J = 6.8 Hz, 1H), 7.29 (t, J = 4.8 Hz, 2H), 7.23 (m, 2H), 7.11 (dd, J = 0.4, 6.8 Hz, 1H), 4.91 (s, 2H), 4.56 (d, J = 6 Hz, 2H) ppm; $^{13}$C NMR (100 MHz, DMSO) δ 166.9, 165.9, 155.6, 139.3, 137.7, 132.3, 131.6, 130.1, 128.3, 127.2, 126.7, 124.1, 121.6, 121.2, 115.3, 114.1, 68.0, 42.7 ppm; HRMS calcd for $C_{22}H_{19}BrN_2O_3$ [M + H$^+$] 439.0652, found 439.0656 |

TABLE 2-continued

| Cpd. No. | Structure | Name | Analytical Data |
|---|---|---|---|
| 18 | 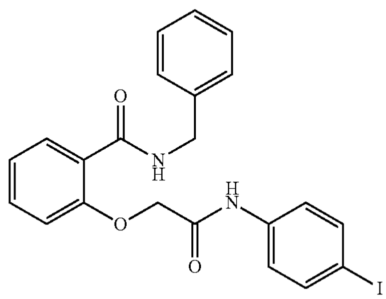 [SMILES: O=C(COc1ccccc1C(=O)NCc1ccccc1)Nc1ccc(I)cc1] | N-benzyl-2-(2-((4-iodophenyl)amino)-2-oxoethoxy)benzamide (CID-24382059) | $^1$H NMR (400 MHz, DMSO) δ 10.60 (s, 1H), 9.28 (t, J = 1.8 Hz, 1H), 7.75 (d, J = 1.6 Hz, 1H), 7.73 (d, J = 1.6 Hz, 2H), 7.50 (m, 3H), 7.391 (d, J = 1.6 Hz, 2H), 7.34 (t, J = 1.2 Hz, 2H), 7.21 (m, 2H), (t, J = .8 Hz, 1H), 4.91 (s, 2H), 4.56 (d, 6Hz, 2H) ppm; $^{13}$C NMR (100 MHz, DMSO) δ 166.9, 165.9, 155.6, 139.3, 138.2, 137.5, 132.3, 130.1, 128.3, 127.2, 126.7, 124.1, 121.6, 121.5, 114.1, 87.4, 68.0, 42.7 ppm; IR $v_{max}$ (cm $^{-1}$) 3263, 3064, 2920, 1688, 1630; HRMS calcd for $C_{22}H_{19}IN_2O_3$ [M + H$^+$] 487.0513, found 487.0513 |
| 19 | 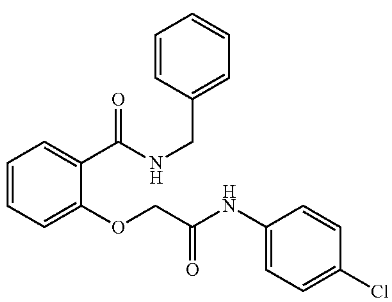 [SMILES: O=C(COc1ccccc1C(=O)NCc1ccccc1)Nc1ccc(Cl)cc1] | N-benzyl-2-(2-((4-chlorophenyl)amino)-2-oxoethoxy)benzamide | |
| 20 | 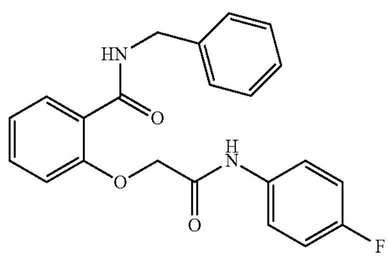 [SMILES: O=C(COc1ccccc1C(=O)NCc1ccccc1)Nc1ccc(F)cc1] | N-benzyl-2-(2-(4-fluorophenylamino)-2-oxoethoxy)benzamide (CID-7981666) | $^1$H NMR (400 MHz, DMSO) δ 10.57 (s, 1H), 9.25 (t, J = 6.0 Hz, 1H), 7.73 (dd, J = 2.0, 6.0 Hz, 1H), 7.65 (m, 2H), 7.49 (td, J = 1.2, 5.6 Hz, 1H), 7.38 (d, J = 6.8 Hz, 2H), 7.31 (t, J = 6.4 Hz, 2H), 7.24-7.09 (5H), 4.55 (s, 2H), 4.55 (d, J = 6.4 Hz, 2H) ppm; $^{13}$C NMR (100 MHz, DMSO) δ HRMS calcd for $C_{22}H_{19}FN_2O_3$ [M + H$^+$] 379.1452, found 379.1455 |
| 21 | 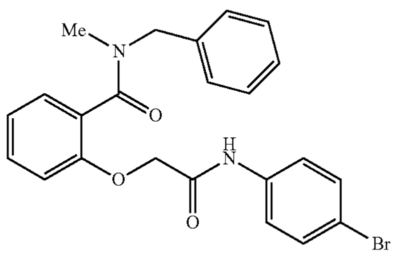 [SMILES: CN(Cc1ccccc1)C(=O)c1ccccc1OCC(=O)Nc1ccc(Br)cc1] | N-benzyl-2-(2-(4-bromophenyl amino)-2-oxoethoxy)-N-methyl benzamide (CID-34284515) | $^1$H NMR (400 MHz, DMSO) δ 10.31 (s, 1H), 7.63 (m, 2H), 7.49 (m, 1H), 7.37 (m, 4H), 7.25 (t, J = 12 Hz, 1H), 8.4 (d, J = 8.4 Hz, 2H), 7.07 (td, 0.4, 6.8 Hz, 1H) ppm; $^{13}$C NMR (100 MHz, DMSO) δ 168.8, 166.7, 153.8, 137.8, 137.0, 136.7, 131.7, 131.6, 130.6, 130.5, 128.6, 128.5, 127.7, 127.6, 127.4, 127.3, 127.0, 126.0, 125.8, 121.5, 113.1, 112.9, 67.4, 53.9, 49.5, 42.1, 36.0, 32.2 ppm; HRMS calcd for $C_{23}H_{21}BrN_2O_3$ [M + H$^+$] 453.0808, found 453.0810 |

TABLE 2-continued

| Cpd. No. | Structure | Name | Analytical Data |
|---|---|---|---|
| 22 | 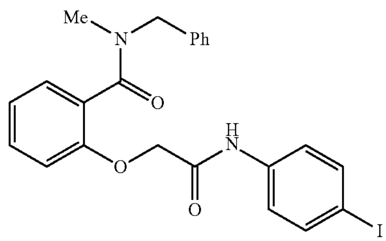 [SMILES: CN(Cc1ccccc1)C(=O)c1ccccc1OCC(=O)Nc1ccc(I)cc1] | N-benzyl-2-(2-(4-iodophenylamino)-2-oxoethoxy)-N-methylbenzamide (CID-46926402) | $^1$H NMR (400 MHz, DMSO) δ 10.27 (s, 1H), 7.66 (m, 2H), 7.49 (t, J = 6.8 Hz, 2H), 7.42-7.31 (m, 5H), 7.24 (t, J = 7.2 Hz, 1H), 7.15 (d, J = 8.4 Hz, 2H), 7.07 (td, J = 0.4, 6.8 Hz), 4.85 (s, 2H), 4.73 (2H), 4.73 (s, 3H) ppm; $^{13}$C NMR (100 MHz, DMSO) δ 168.7, 166.7, 153.8, 138.2, 137.5, 128.6, 128.5, 127.7, 127.6, 127.4, 127.3, 127.1, 126.0, 125.8, 121.5, 121.4, 113.1, 112.9, 87.3, 67.4, 53.8, 40.4, 36.0, 32.2 ppm; HRMS calcd for $C_{23}H_{21}IN_2O_3$ [M + H$^+$] 501.067, found 501.0669 |
| 23 | 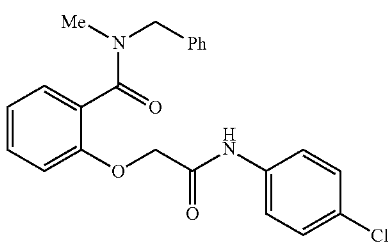 [SMILES: CN(Cc1ccccc1)C(=O)c1ccccc1OCC(=O)Nc1ccc(Cl)cc1] | N-benzyl-2-(2-(4-chlorophenyl amino)-2-oxoethoxy)-N-methyl benzamide (CID-46926404) | $^1$H NMR (400 MHz, DMSO) δ 7.68 (m, 2H), 7.42-7.31 (m, 7H), 7.26 (m, 1H), 7.17 (d, J = 8.4 Hz, 2H), 7.08 (td, J = 0.8, 6.8 Hz, 1H), 4.86 (s, 2H), 4.74 (s, 2H), 2.81 (s, 3H) ppm; $^{13}$C NMR (100 MHz, DMSO) δ 168.6, 166.7, 153.8, 137.3, 130.6, 130.5, 128.7, 128.6, 128.5, 127.6, 127.4, 127.1, 127.0, 121.5, 120.8, 113.1, 112.9, 67.4, 53.8. 32.2 ppm; HRMS calcd for $C_{23}H_{21}ClN_2O_3$ [M + H$^+$] 409.1313, found 409.1312 |
| 24 | 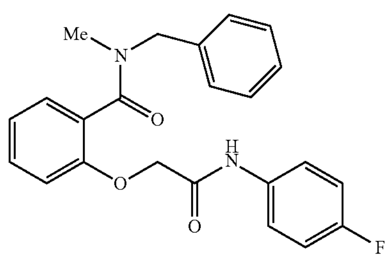 [SMILES: CN(Cc1ccccc1)C(=O)c1ccccc1OCC(=O)Nc1ccc(F)cc1] | N-benzyl-2-(2-(4-fluorophenyl amino)-2-oxoethoxy)-N-methyl benzamide (CID-46926393) | $^1$H NMR (400 MHz, DMSO) δ 10.24 (s, 1H), 7.69 (m, 2H), 7.43 (m, 1H), 7.38 *m, 4H), 7.33 (m, 1H), 7.16 (m, 4H), 7.09 (t, J = 0.8 Hz, 1H), 4.86 (s, 2H), 4.48 (s, 2H), 2.93 (s, 3H) ppm; $^{13}$C NMR (100 MHz, DMSO) δ ppm; HRMS calcd for $C_{23}H_{21}FN_2O_3$ [M + H$^+$] 393.1609, found 393.1607 |
| 25 | 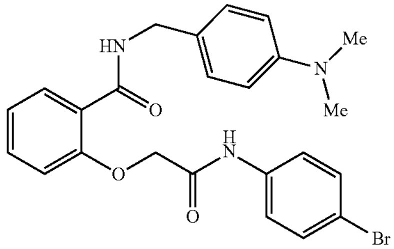 [SMILES: CN(C)c1ccc(CNC(=O)c2ccccc2OCC(=O)Nc2ccc(Br)cc2)cc1] | 2-(2-(4-bromophenyl amino)-2-oxoethoxy)-N-(4-dimethylamino benzyl) benzamide (CID-31786241) | $^1$H NMR (400 MHz, DMSO) δ 10.66 (s, 1H), 9.11 (t, J = 6.0 Hz, 1H), 7.70 (dd, J = 1.6, 6.0 Hz, 1H), 7.63, J = 6.8 Hz, 2H), 7.49 (m, 3H), 7.19 (m, 3H), 7.11 (td, J = 0.8, 6.8 Hz, 1H), 6.64 (d, J = 6.8 Hz, 2H), 4.89 (s, 2H), 4.43 (d, (J = 5.6 Hz, 2H), 2.82 (s, 6H) ppm; $^{13}$C NMR (100 MHz, DMSO) δ 166.9, 165.8, 155.5, 149.5, 137.7, 132.1, 131.6, 129.9, 128.2, 126.6, 124.4, 121.6, 121.2, 115.3, 114.1, 112.3, 68.1, 42.3 ppm; HRMS calcd for $C_{24}H_{24}BrN_3O_3$ [M + H$^+$] 482.1074, found 482.1066 |

TABLE 2-continued

| Cpd. No. | Name | Analytical Data |
|---|---|---|
| 26 | 2-(2-(4-bromophenyl amino)-2-oxoethoxy)-N-(4-methoxy benzyl)benzamide (CID-43001960) | $^1$H NMR (400 MHz, DMSO) δ 10.65 (s, 1H), 9.20 (t, J = 2.4 Hz, 1H), 7.72 (dd, J = 2.4, 5.6 Hz, 1H), 7.62 (d, J = 4.4 Hz, 1H), 7.53-7.47 (m, 3H), 7.28 (d, J = 4.8 Hz, 1H), 7.2 (d, J = 8.0 Hz, 1H), 7.08 (td, 0.8, 6.4 Hz, 1H), 6.87 (d, J = 4.4 Hz, 1H), 4.91 (s, 2H), 4.49 (d, J = 6.0 Hz, 2H), 4.48 (s, 3H) ppm; $^{13}$C NMR (100 MHz, DMSO) δ 166.9, 165.9, 158.2, 155.6, 137.7, 132.2, 131.6, 131.2, 130.0, 128.5, 124.2, 121.6, 121.2, 115.3, 114.1, 113.7, 68.0, 54.9, 42.2 ppm; HRMS calcd for C$_{23}$H$_{21}$BrN$_2$O$_4$ [M + H$^+$] 468.0685, found 468.0670 |
| 27 | 2-(2-(4-bromophenyl amino)-2-oxoethoxy)-N-(4-(trifluoromethyl)benzyl)benzamide (CID-46926394) | $^1$H NMR (400 MHz, DMSO) δ 10.55 (s, 1H), 9.36 (t, J = 6.0 Hz, 1H), 7.76 (dd, J = 1.6, 6.0 Hz, 1H), 7.65 (d, J = 8.4 Hz, 2H), 7.57 (m, 4H), 7.51 (m, 3H), 7.21 (d, J = 8.0 Hz, 1H), 7.12 (td, J = 0.8, 6.8 Hz, 1H), 7.09 (s, 2H), 4.91 (s, 2H), 4.62 (d, J = 6.0 Hz, 2H) ppm; $^{13}$C NMR (100 MHz, DMSO) δ 166.9, 166.1, 155.6, 144.2, 137.6, 132.4, 131.6, 130.1, 127.8, 127., 127.3, 125.7, 125.2, 125.1, 123.9, 122.9, 121.6, 121.2, 115.3, 114.0, 68.0, 42.4 ppm; HRMS calcd for C$_{23}$H$_{18}$BrF$_3$N$_2$O$_3$ [M + H$^+$] 507.0526, found 507.0529 |
| 28 | N-(4-bromobenzyl)-2-(2-(4-bromophenylamino)-2-oxoethoxy)benzamide (CID-46926386) | $^1$H NMR (400 MHz, DMSO) δ 10.57 (s, 1H), 9.28 (t, J = 2.4 Hz, 1H), 7.736 (dd, J = 2.0, 5.6 Hz, 1H), 7.58 (d, J = 4.8 Hz, 2H), 7.50 (m, 4H), 7.34 (d, J = 8.4 Hz, 2H), 7.19 (d, J = 8.0 Hz, 1H), 7.11 (td, J = 0.8, 6.8 Hz, 1H), 4.9 (s, 2H), 4.51 (d, J = 6.0 Hz, 2H) ppm; $^{13}$C NMR (100 MHz, DMSO) δ 166.9, 165.9, 155.6, 138.7, 137.7, 132.4, 131.6, 131.1, 130.1, 129.4, 123.9, 121.6, 121.2, 119.8, 115.4, 114.1, 68.0, 42.2 ppm; HRMS calcd for C$_{22}$H$_{18}$Br$_2$N$_2$O$_3$ [M + H$^+$] 516.9757, found 516.9757 |
| 29 | 2-(2-(4-bromophenyl amino)-2-oxoethoxy)-N-(4-tert-butyl phenyl)benzamide (CID-46926396) | $^1$H NMR (400 MHz, DMSO) δ 10.63 (s, 1H), 9.23 (t, J = 1.6 Hz, 1H), 7.72 (dd, J = 1.6, 6.0 Hz, 1H), 7.61 (d, J = 6.8 Hz, 2H), 7.49 (m, 3H) 7.29 (m, 4H), 7.21 (d, J = 8.0 Hz, 1H), 7.12 (td, J = 0.4, 7.6 Hz, 1H), 4.91 (s, 2H), 4.52 (d, J = 6 Hz, 2H), 1.26 (s, 9H) ppm; $^{13}$C NMR (100 MHz, DMSO) δ 166.9, 165.9, 155.5, 149.1, 137.7, 136.2, 132.2, 131.6, 129.9, 127.1, 126.9, 124.9, 124.3, 121.6, 121.2, 115.3, 114.1, 68.1, 34.1, 31.1, 30.7 ppm; HRMS calcd for C$_{25}$H$_{25}$BrN$_2$O$_3$ [M + H$^+$] 495.1278, found 495.1276 |

TABLE 2-continued

| Cpd. No. | Structure | Name | Analytical Data |
|---|---|---|---|
| 30 | 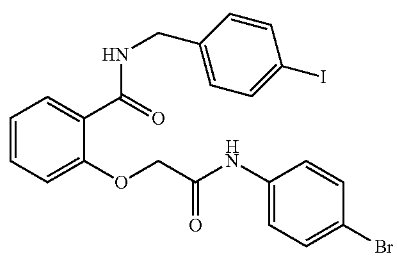 [SMILES: O=C(COc1ccccc1C(=O)NCc1ccc(I)cc1)Nc1ccc(Br)cc1] | 2-(2-(4-bromophenylamino)-2-oxoethoxy)-N-(4-iodobenzyl)benzamide CID-46926390) | $^1$H NMR (400 MHz, DMSO) δ 10.57 (s, 1H), 9.27 (t, J = 6.0 Hz, 1H), 7.74 (dd, J = 1.6, 6.0 Hz, 1H), 7.65 (d, J = 4.8 Hz, 2H), 7.58 (d, J = 6.8 Hz, 2H), 7.51 (m, 3H), 7.19 (dd, J = 2.4, 6.0 Hz, 3H), 7.11 (td, J = 0.8, 6.8 Hz, 1H), 4.89 (s, 2H), 4.49 (d, J = 6.0 Hz, 2H) ppm; $^{13}$C NMR (100 MHz, DMSO) δ 166.9, 165.9, 155.6, 139.1, 137.7, 136.9, 132.3, 131.6, 130.1, 129.6, 123.9, 121.6, 121.2, 115.4, 114.1, 92.5, 68.0, 42.3, 42.1 ppm; HRMS calcd for $C_{22}H_{18}BrIN_2O_3$ [M + H$^+$] |
| 31 | 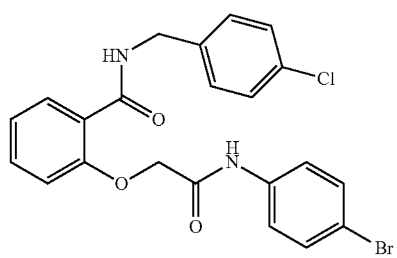 [SMILES: O=C(COc1ccccc1C(=O)NCc1ccc(Cl)cc1)Nc1ccc(Br)cc1] | 2-(2-(4-bromophenyl amino)-2-oxoethoxy)-N-(4-chloro benzyl)benzamide (CID-46926388) | $^1$H NMR (400 MHz, DMSO) δ 10.58 (s, 1H), 9.29 (t, J = 6.0 Hz, 1H), 7.75 (dd, J = 1.6, 6.0 Hz, 1H), 7.59 (d, J = 4.4 Hz, 2H), 7.50 (m, 3H), 7.38 (m, 4H), 7.18 (d, J = 7.6 Hz, 1H), 7.11 (td, 0.8, 6.8 Hz, 1H), 4.91 (s, 2H), 4.54 (d, J = 6.0 Hz, 2H) ppm; $^{13}$C NMR (100 MHz, DMSO) δ 166.9, 165.9, 155.6, 138.3, 137.7, 132.4, 131.6, 131.3, 130.1, 129.1, 128.2, 123.9, 121.6, 121.2, 115.4, 114.1, 68.0, 42.1 ppm; HRMS calcd for $C_{22}H_{18}BrClN_2O_3$ [M + H$^+$] 473.0262, found 473.0263 |
| 31a | 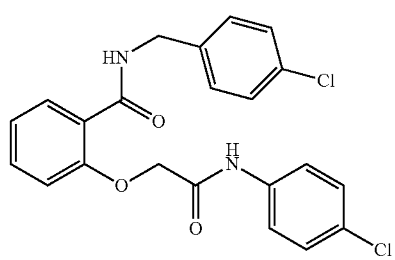 [SMILES: O=C(COc1ccccc1C(=O)NCc1ccc(Cl)cc1)Nc1ccc(Cl)cc1] | N-(4-chlorobenzyl)-2-(2-(4-chlorophenylamino)-2-oxoethoxy)benzamide (CID-46926397) | $^1$H NMR (400 MHz, DMSO) δ 10.58 (s, 1H), 9.28 (t, J = 6.0 Hz, 1H), 7.74 (dd, J = 1.6, 6.0 Hz, 1H), 7.65 (d, J = 6.8 Hz, 2H), 7.52 (td, 2.0, 5.6 Hz, 1H), 7.38 (m, 6H), 7.19 (d, J = 7.6 Hz, 1H), 7.13 (td, J = 0.8, 6.8 Hz, 1H), 4.90 (s, 2H), 4.53 (d, J = 6.0 Hz, 2H) ppm; $^{13}$C NMR (100 MHz, DMSO) δ 166.9, 165.9, 155.6, 138.3, 137.3, 132.4, 131.3, 130.1, 129.1, 128.7, 128.2, 127.3, 123.9, 121.6, 120.8, 114.1, 67.9, 42.1 ppm; HRMS calcd for $C_{22}H_{18}Cl_2N_2O_3$ [M + H$^+$] 429.0767, found 429.0763 |
| 32 | 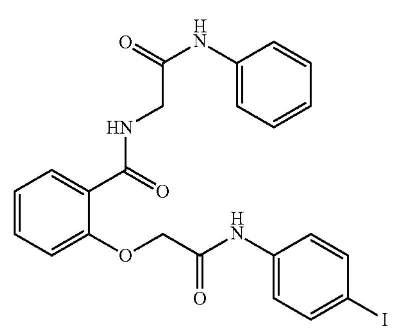 [SMILES: O=C(CNC(=O)c1ccccc1OCC(=O)Nc1ccc(I)cc1)Nc1ccccc1] | 2-(2-(4-iodophenyl amino)-2-oxoethoxy)-N-(2-oxo-2-(phenyl amino)ethyl)benzamide (CID-46937183) | $^1$H NMR (400 MHz, DMSO) δ 10.50 (s, 1H), 10.10 (s, 1H), 9.06 (t, J = 6.0 Hz, 1H), 7.79 (dd, J = 1.2, 4.8 Hz, 1H), 7.65 (d, J = 7.2 Hz), 7.59-7.47 (m, 5H), 7.41 (m, 1H), 7.28 (m, 2H), 7.18 (d, J = 6.4 Hz, 1H), 7.14-7.04 (m, 2H), 4.91 (s, 2H), 4.14 (s, 2H) ppm; $^{13}$C NMR (100 MHz, DMSO) δ 167.5, 166.7, 155.8, 138.9, 138.1, 137.5, 137.4, 130.5, 128.7, 123.3, 123.2, 121.7, 121.5, 121.4, 119.0, 114.0, 87.4, 67.9, 43.4 ppm; HRMS calcd for $C_{23}H_{20}IN_3O_4$ [M + H$^+$] 530.0571, found 530.0568 |

| Cpd. No. | Structure | Name | Analytical Data |
|---|---|---|---|
| 33 | 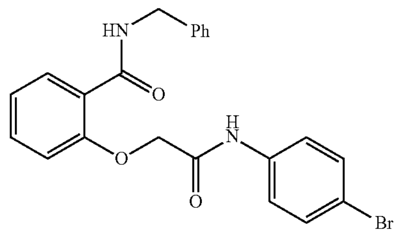 [SMILES: O=C(COc1ccccc1C(=O)NCc1ccccc1)Nc1ccc(Br)cc1] | N-benzyl-2-(2-(4-bromophenylamino)-2-oxoethoxy)benzamide (CID-46943206) | $^1$H NMR (400 MHz, DMSO) δ 10.53 (s, 1H), 10.11 (s, 1H), 9.04 (t, J = 1.2 Hz, 1H), 7.79 (dd, J = 1.2, 4.8 Hz, 1H), 7.64-7.58 (m, 3H), 7.53 (td, J = 1.2, 4.4 Hz, 1H), 7.42 (d, J = 6Hz, 2H), 7.30 (t, J = 4.4 Hz, 2H), 7.20 (d, J = 6.4 Hz, 1H), 7.13 (td, J = 0.8, 5.2 Hz, 1H), 7.07 (t, J = 6.0 Hz, 1H), 4.98 (s, 2H), 4.15 (s, 2H) ppm; $^{13}$C NMR (100 MHz, DMSO) δ 167.5, 166.8, 166.1, 155.8, 138.9, 137.6, 138.9, 137.6, 132.6, 131.6, 131.5, 130.5, 130.3, 128.7, 127.7, 123.3, 123.2, 121.5, 121.1, 119.0, 115.4, 114.0, 113.2, 67.9, 67.2 ppm; HRMS calcd for $C_{23}H_{20}BrN_3O_4$ [M + H$^+$] 482.0705, found 482.0710 |
| 34 | 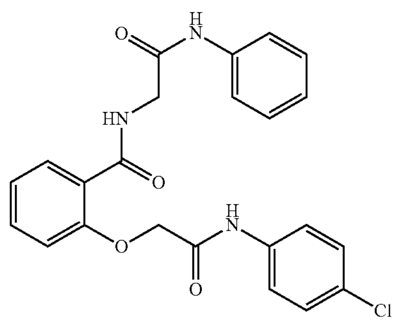 [SMILES: O=C(CNC(=O)c1ccccc1OCC(=O)Nc1ccc(Cl)cc1)Nc1ccccc1] | 2-(2-(4-chlorophenyl amino)-2-oxoethoxy)-N-(2-oxo-2-(phenyl amino)ethyl)benzamide (CID-46943223) | $^1$H NMR (400 MHz, DMSO) δ 10.54 (s, 1H), 10.10 (s, 1H), 9.13 (t, J = 6.0 Hz, 1H), 7.79 (dd, J = 1.2, 4.8 Hz, 1H), 7.71 (d, J = 7.2 Hz, 1H), 7.67 (d, J = 4.0 Hz, 2H), 7.59 (d, J = 6.0 Hz, 2H), 7.53 (m, 1H), 7.39 (d, J = 6.0 Hz, 1H), 7.29 (m, 3H), 7.19 (d, J = 6.4 Hz, 1H), 7.14 (t, J = 5.6 Hz, 1H), 7.05 (td, J = 0.8, 5.2 Hz, 1H), $^{13}$C NMR (100 MHz, DMSO) δ HRMS calcd for $C_{23}H_{20}ClN_3O_4$ [M + H$^+$] 438.1215, found 438.1210 |
| 35 | 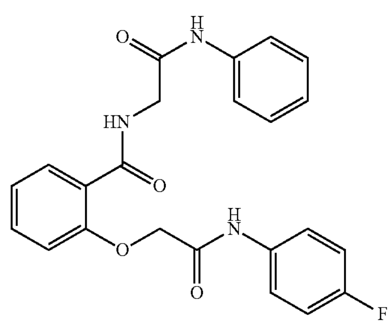 [SMILES: O=C(CNC(=O)c1ccccc1OCC(=O)Nc1ccc(F)cc1)Nc1ccccc1] | 2-(2-(4-fluoro phenylamino)-2-oxoethoxy)-N-(2-oxo-2-(phenyl amino)ethyl)benzamide (CID-46943229) | $^1$HNMR (400 MHz, DMSO) δ 10.46 (s, 1H), 10.09 (s, 1H), 9.04 (t, J = 6.0 Hz, 1H), 7.79 (dd, J = 1.2, 4.8 Hz, 1H), 7.65 (m, 2H), 7.59 (d, J = 6.0 Hz), 7.52 (td, J = 1.6, 4.4 Hz, 1H), 7.28 (t, J = 6.0 Hz, 2H), 7.13 (d, J = 6.4 Hz, 1H), 7.11 (0.4, 5.6 Hz, 1H), 7.06 (m, 3H), 4.91 (s, 2H), 4.13 (d, J = 4.4 Hz, 2H) ppm; $^{13}$C NMR (100 MHz, DMSO) δ 167.5, 166.5, 159.2, 157.3, 155.8, 138.9, 134.6, 132.5, 130.3, 128.7, 123.4, 121.5, 121.5, 121.4, 119.0, 115.4, 114.0, 67.9, 43.4 ppm; HRMS calcd for $C_{23}H_{20}FN_3O_4$ [M + H$^+$] 422.1511, found 422.1505 |
| 36 | 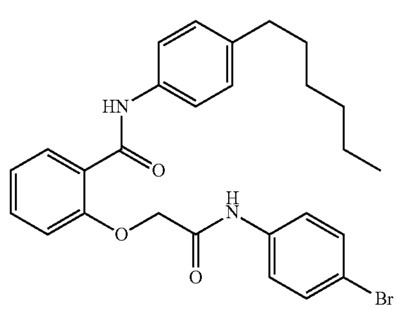 | 2-(2-(4-bromophenylamino)-2-oxoethoxy)-N-(4-hexyl phenyl)benzamide (CID-46943220) | $^1$H NMR (400 MHz, DMSO) δ 10.52 (s, 1H), 10.01 (s, 1H), 7.78 (dd, J = 1.6, 4.8 Hz, 1H), 7.61 (d, J = 4.0 Hz, 2H), 7.52 (td, J = 1.2, 4.8 Hz, 1H), 7.47 (d, J = 6.8 Hz, 2H), 7.39 (d, J = 4.0 Hz, 2H),7.21 (d, J = 6.4 Hz, 1H), 7.12 (td, J = 0.4, 5.6 Hz, 2H), 7.11 (d, J = 6.8 Hz, 2H), 4.90 (s, 2H), 4.12 (d, J = 4.4 Hz, 2H), 2.51 (m, 2H), 1.26 (m, 2H), 1.25 (m, 6H), 0.84 (t, J = 1.2 Hz, 3H) ppm; $^{13}$C NMR (100 MHz, DMSO) δ HRMS calcd for $C_{27}H_{29}BrN_2O_3$ [M + H$^+$] 566.1649, found 566.1644 |

TABLE 2-continued

| Cpd. No. | Structure | Name | Analytical Data |
|---|---|---|---|
| 37 | 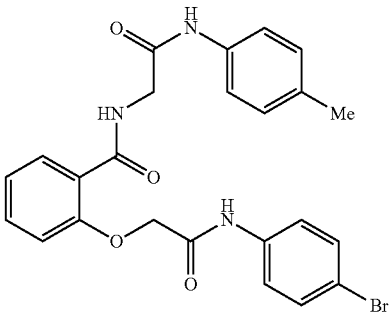 [SMILES: Cc1ccc(NC(=O)CNC(=O)c2ccccc2OCC(=O)Nc2ccc(Br)cc2)cc1] | 2-(2-(4-bromophenyl amino)-2-oxoethoxy)-N-(2-oxo-2-(p-tolylamino)ethyl)benzamide (CID-46937196) | $^1$H NMR (400 MHz, DMSO) δ 10.54 (s, 1H), 10.01 (s, 1H), 9.03 (t, J = 6.0 Hz, 1H), 7.79 (dd, J = 1.2, 4.8 Hz, 1H), 7.61 (d, J = 4.0 Hz, 2H), 7.52 (td, J = 1.6, 4.4 Hz, 1H), 7.47 (d, J = 6.8 Hz, 2H), 7.39 (d, J = 6.8 Hz, 2H), 7.21 (d, J = 6.4 Hz, 1H), 7.14 (dd, J = 0.4, 5.6 Hz, 1H), 7.11 (d, J = 6.8 Hz, 2H), 4.92 (s, 2H), 4.13 (d, J = 4.8 Hz, 2H), 2.26 (s, 3H) ppm; 167.2, 166.8, 166.1, 155.8, 137.6, 136.4, 132.5, 132.1, 131.5, 130.3, 129.1, 123.4, 121.5, 121.4, 119.1, 115.4, 114.1, 67.9, 43.4, 20.4 ppm; $^{13}$C NMR (100 MHz, DMSO) δ HRMS calcd for $C_{24}H_{22}BrN_3O_4$ [M + H$^+$] 496.0866, found 496.0882 |
| 38 | 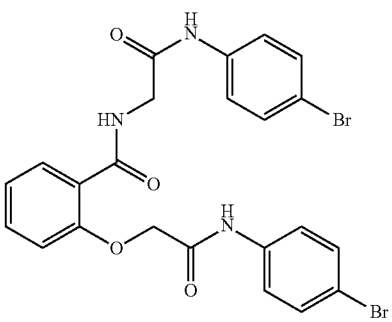 [SMILES: O=C(CNC(=O)c1ccccc1OCC(=O)Nc1ccc(Br)cc1)Nc1ccc(Br)cc1] | 2-(2-(4-bromophenyl amino)-2-oxoethoxy)-N-(2-(4-bromo phenylamino)-2-oxoethyl)benzamide (CID-46937197) | $^1$H NMR (400 MHz, DMSO) δ 10.51 (s, 1H), 10.25 (s, 1H), 9.05 (t, J = 0.8 Hz, 1H), 7.79 (dd, J = 1.6, 4.8 Hz, 1H), 7.61 (d, J = 3.6 Hz, 2H), 7.59 (d, J = 3.6 Hz, 2H), 7.52 (m, 1H), 7.49 (d, J = 3.6H, 2H), 7.41 (d, J = 4.0 Hz, 2H), 7.21 (d, J = 6.4 Hz, 1H), 7.12 (td, J = 0.4, 6.0 Hz, 1H), 4.91 (s, 2H), 4.12 (d, J = 0.8 Hz, 2H) ppm; $^{13}$C NMR (100 MHz, DMSO) δ HRMS calcd for $C_{23}H_{19}Br_2N_3O_4$ [M + H$^+$] 559.9815, found 559.9815 |
| 39 | 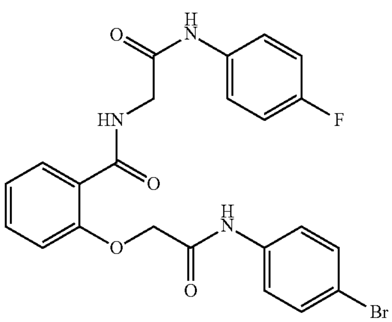 | 2-(2-((4-bromophenyl)amino)-2-oxoethoxy)-N-(2-((4-fluorophenyl)amino)-2-oxoethyl)benzamide | |
| 40 | 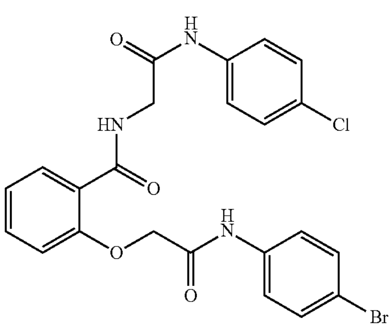 | 2-(2-((4-bromophenyl)amino)-2-oxoethoxy)-N-(2-((4-chlorophenyl)amino)-2-oxoethyl)benzamide | |

TABLE 2-continued

| Cpd. No. | Structure | Name | Analytical Data |
|---|---|---|---|
| 41 | 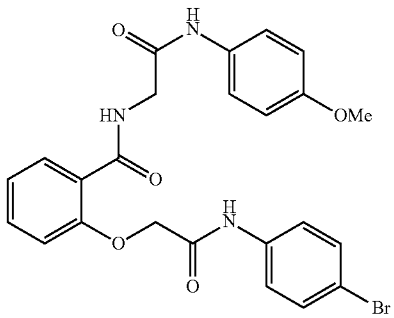 [SMILES: COc1ccc(NC(=O)CNC(=O)c2ccccc2OCC(=O)Nc2ccc(Br)cc2)cc1] | 2-(2-((4-bromophenyl)amino)-2-oxoethoxy)-N-(2-((4-methoxyphenyl)amino)-2-oxoethyl)benzamide | |
| 42 | 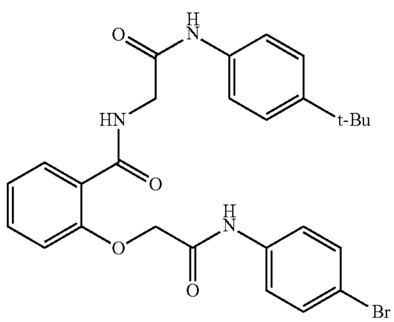 | 2-(2-(4-bromophenyl amino)-2-oxoethoxy)-N-(2-(4-tert-butyl phenylamino)-2-oxoethyl)benzamide | $^1$H NMR (400 MHz, DMSO) δ 10.52 (s, 1H), 10.03 (s, 1H), 9.02 (t, J = 4.8 Hz, 1H), 7.78 (dd, 1.2, 4.8 Hz, 1H), 7.61 (d, J = 7.2 Hz, 2H), 7.53 (td, J = 1.6, 4.4 Hz, 1H), 7.49 (d, J = 6.8 Hz, 2H), 7.39 (d, J = 6.8 Hz, 2H), 7.31 (d, J = 6.8 Hz, 2H), 7.22 (d, J = 6.4 Hz, 1H), 7.12 (td, J = 0.8, 5.6Hz, 1H), 4.91 (s, 2H), 4.13 (d, J = 4.8 Hz, 2H), 1.26 (s, 9H) ppm; $^{13}$C NMR (100 MHz, DMSO) δ 167.2, 166.7, 166.1, 155.7, 145.5, 137.6, 136.3, 132.5, 131.6, 130.3, 125.3, 123.4, 121.6, 118.8, 115.4, 114.1, 67.9, 43.4, 33.9, 31.2 ppm; HRMS calcd for $C_{27}H_{28}BrN_3O_4$ [M + H$^+$] 538.1336, found 538.1337 |
| 43 | 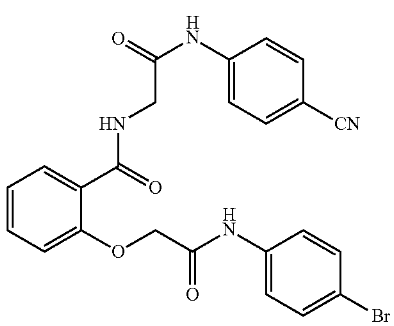 [SMILES: N#Cc1ccc(NC(=O)CNC(=O)c2ccccc2OCC(=O)Nc2ccc(Br)cc2)cc1] | 2-(2-((4-bromophenyl)amino)-2-oxoethoxy)-N-(2-(4-cyano phenylamino)-2-oxoethyl)benzamide (CID-46937202) | $^1$H NMR (400 MHz, DMSO) δ 10.58 (s, 1H), 10.51 (s, 1H), 9.09 (t, J = 4.8 Hz, 1H), 7.79 (dd, J = 1.6, 4.4 Hz, 1H), 7.76 (s, 4H), 7.60 (d, J = 4.0 Hz, 2H), 7.53 (td, J = 1.6, 4.4 Hz, 1H), 7.40 (d, J = 4.0 Hz, 2H), 7.20 (d, J = 6.4 Hz, 1H), 7.14 (td, J = 0.4, 5.6 Hz, 1H), 4.91 (s, 2H), 4.91 (d, J = 4.8 Hz, 2H) ppm; $^{13}$C NMR (100 MHz, DMSO) δ 168.4, 166.7, 166.2, 155.8, 143.1, 137.6, 133.3, 132.6, 131.5, 130.3, 123.2, 121.5, 121.5, 119.0, 115.3, 114.1, 104.9, 67.9, 43.6 ppm; HRMS calcd for $C_{27}H_{29}BrN_2O_3$ [M + H$^+$] 507.0662, found 507.0661 |

TABLE 2-continued

| Cpd. No. | Structure | Name | Analytical Data |
|---|---|---|---|
| 44 | 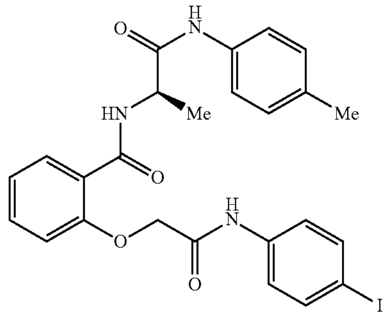 [SMILES: Cc1ccc(NC(=O)[C@@H](C)NC(=O)c2ccccc2OCC(=O)Nc2ccc(I)cc2)cc1] | (R)-2-(2-(4-iodophenyl amino)-2-oxoethoxy)-N-(1-oxo-1-(p-tolylamino)propan-2-yl)benzamide (CID-50985692) | $^1$H NMR (400 MHz, DMSO) δ 10.57 (s, 1H), 10.03 (s, 1H), 8.97 (d, J = 5.2 Hz, 1H), 7.80 (dd, J = 1.2, 4.8 Hz, 1H), 7.54-7.47 (m, 7H), 7.2 (d, J = 6.4 Hz, 1H), 7.14 (d, J = 0.4 Hz, 1H), 7.11 (d, J = 6.4 Hz, 2H), 4.89 (s, 2H), 4.60 (t, J = 5.2 Hz, 1H), 2.27 (s, 3H), 1.46 (d, J = 5.6 Hz, 3H) ppm; $^{13}$C NMR (100 MHz, DMSO) δ 170.9, 166.6, 165.4, 155.8, 138.1, 137.4, 137.1, 136.5, 132.5, 132.4, 132.3, 132.1, 130.5, 129.0, 123.1, 122.5, 121.5, 119.4, 119.1, 113.9, 88.7, 87.3, 67.9, 49.6, 20.5, 17.9 ppm; HRMS calcd for $C_{25}H_{24}IN_3O_4$ [M + H$^+$] 558.0835, found 558.0920 |
| 45 | 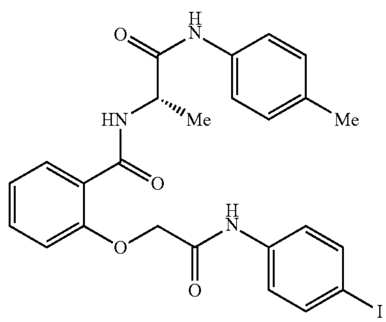 [SMILES: Cc1ccc(NC(=O)[C@H](C)NC(=O)c2ccccc2OCC(=O)Nc2ccc(I)cc2)cc1] | (S)-2-(2-(4-iodophenyl amino)-2-oxoethoxy)-N-(1-oxo-1-(p-tolylamino)propan-2-yl)benzamide (CID-50985684) | $^1$H NMR (400 MHz, DMSO) δ 10.56 (s, 1H), 10.03 (s, 1H), 8.97 (d, J = 5.2 Hz, 1H), 7.80 (dd, J = 1.6, 4.8 Hz, 1H), 7.51 (m, 7H), 7.20 (d, J = 6.8 Hz, 1H), 7.14 (d, J = 6.4 Hz, 1H), 7.11 (d, J = 6.4 Hz, 2H), 4.89 (s, 2H), 4.61 (q, J = 5.6 Hz, 1H), 2.27 (s, 3H), 1.46 (d, J = 5.6 Hz, 3H) ppm; $^{13}$C NMR (100 MHz, DMSO) δ 170.9, 166.6, 165.4, 155.8, 138.1, 137.4, 136.5, 132.6, 132.1, 130.5, 129.0, 123.1, 121.6, 121.5, 119.1, 113.9, 87.3, 67.9, 49.9, 20.5, 17.9 ppm; HRMS calcd for $C_{25}H_{24}IN_3O_4$ [M + H$^+$] 558.0884, found 558.0904 |
| 46 | 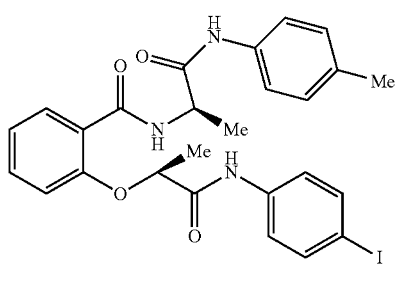 [SMILES: Cc1ccc(NC(=O)[C@@H](C)NC(=O)c2ccccc2O[C@@H](C)C(=O)Nc2ccc(I)cc2)cc1] | 2-((S)-1-(4-iodophenylamino)-1-oxopropan-2-yloxy)-N-((R)-1-oxo-1-(p-tolylamino)propan-2-yl)benzamide (CID-53230301) | $^1$H NMR (400 MHz, DMSO) δ 10.84 (s, 1H), 10.10 (s, 1H), 8.94 (d, J = 4.8 Hz, 1H), 7.79 (dd, J = 1.6, 4.8 Hz, 1H), 7.54 (d, J = 6.4 Hz, 2H), 7.52-7.44 (m, 5H), 7.19 (d, J = 6.8 Hz, 1H), 7.12 (d, J = 6.4 Hz, 2H), 7.09 (t, J = 6.0 Hz, 1H), 5.18 (q, J = 5.6Hz, 1H), 4.64 (q, J = 5.2 Hz, 1H), 2.28 (s, 3H), 1.64 (d, J = 5.2 Hz, 3H), 1.43 (d, J = 5.6 Hz, 3H) ppm; $^{13}$C NMR (100 MHz, DMSO) δ 170.8, 170.0, 165.6, 155.2, 138.2, 137.3, 136.5, 132.5, 132.2, 130.6, 129.1, 129.1, 123.5, 121.8, 121.6, 121.5, 119.2, 119.1, 114.2, 87.3, 74.8, 49.9, 20.5, 18.7, 18.1 ppm; HRMS calcd for $C_{27}H_{29}BrN_2O_3$ [M + H$^+$] 572.1041, found 572.1035 |

TABLE 2-continued

| Cpd. No. | Structure | Name | Analytical Data |
|---|---|---|---|
| 47 | 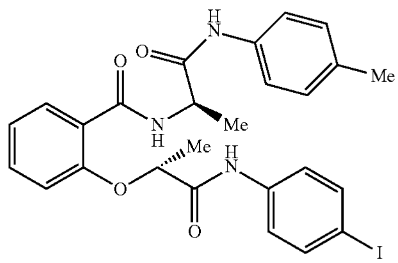 [SMILES: Cc1ccc(NC(=O)[C@@H](C)NC(=O)c2ccccc2O[C@H](C)C(=O)Nc2ccc(I)cc2)cc1] | 2-((R)-1-(4-iodophenylamino)-1-oxopropan-2-yloxy)-N-((R)-1-oxo-1-(p-tolylamino)propan-2-yl)benzamide (CID-53230303) | $^1$H NMR (400 MHz, DMSO) δ 7.77 (dd, J = 1.6, 4.8, 1H), 7.55 (d, J = 7.2 Hz, 2H), 7.49-7.44 (m, 5H), 7.18-7.09 (m, 4H), 5.17 (q, J = 5.2 Hz, 1H), 4.65 (q, 5.6 Hz, 1H), 2.45 (s, 3H), 1.64 (d, J = 5.2 Hz, 3H), 1.43 (d, J = 5.6 Hz, 3H) ppm; $^{13}$C NMR (100 MHz, DMSO) δ 170.8, 170.7, 165.5, 155.1, 138.2, 137.8, 136.5, 136.4, 132.5, 132.2, 130.6, 130., 129.1, 123.7, 123.5, 121.8, 121.5, 119.3, 119.1, 114.2, 113.9, 87.5, 74.8, 49.9, 42.1, 20.5, 18.5 ppm; HRMS calcd for $C_{26}H_{26}IN_3O_4$ [M + H$^+$] 572.1041, found 572.1039 |
| 47a | 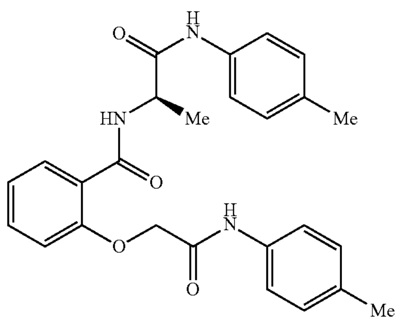 [SMILES: Cc1ccc(NC(=O)COc2ccccc2C(=O)N[C@H](C)C(=O)Nc2ccc(C)cc2)cc1] | (R)-N-(1-oxo-1-(p-tolylamino)propan-2-yl)-2-(2-oxo-2-(p-tolylamino)ethoxy)benzamide (CID-50985710) | $^1$H NMR (400 MHz, DMSO) δ 10.34 (s, 1H), 10.01 (s, 1H), 8.97 (d, J = 5.2 Hz, 1H), 7.80 (dd, J = 1.6,4.4 Hz, 1H), 7.54-7.49 (m, 5H), 7.19 (d, J = 6.4 Hz, 1H), 7.13-7.09 (m, 3H), 7.06 (d, J = 6.4 Hz, 2H), 4.89 (s, 2H), 4.61 (q, J = 5.6 Hz, 1H), 2.25 (s, 3H), 2.23 (s, 3H), 1.45 (d, J = 5.6 Hz, 3H) ppm; $^{13}$C NMR (100 MHz, DMSO) δ 170.9, 166.1, 165.2, 155.8, 135.4, 135.8, 132.6, 132.5, 132.1, 130.5, 129.1, 123.2, 121.4, 119.5, 119.1, 113.8, 67.8, 49.9, 20.4, 17.9 ppm; HRMS calcd for $C_{26}H_{27}N_3O_4$ [M + H$^+$] 445.20, found 445.20 |
| 47b | 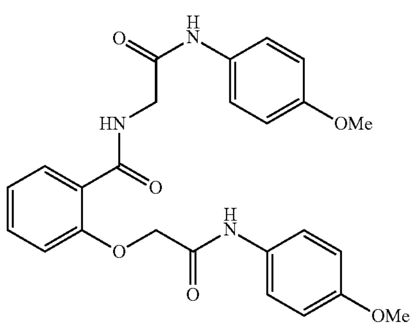 [SMILES: COc1ccc(NC(=O)CNC(=O)c2ccccc2OCC(=O)Nc2ccc(OC)cc2)cc1] | 2-(2-(4-methoxyphenyl amino)-2-oxoethoxy)-N-(2-(4-methoxyphenylamino)-2-oxoethyl)benzamide (CID-50985703) | $^1$H NMR (400 MHz, DMSO) δ 10.26 (s, 1H), 9.54 (s, 1H), 9.03 (t, J = 5.6 Hz, 1H), 7.78 (dd, J = 1.2,4.8 Hz, 1H), 7.54-7.49 (m, 5H), 7.21 (d, J = 6.4 Hz, 1H), 7.12 (t, J = 5.6 Hz, 1H), 6.88 (d, J = 4.0 Hz, 2H), 6.82 (d, J = 4.0 Hz, 2H), 4.88 (s, 2H), 4.12 (d, J = 4.4 Hz, 2H), 3.72 (s, 3H), 3.69, (s, 3H) ppm; $^{13}$C NMR (100 MHz, DMSO) δ 167.0, 166.0, 155.8, 155.1, 132.5, 132.0, 131.3, 130.3, 123.5, 121.4, 120.6, 113.9, 67.9, 55.1, 43.3 ppm; HRMS calcd for $C_{25}H_{25}N_3O_6$ [M + H$^+$] 464.1816, found 464.1834 |
| 47c | 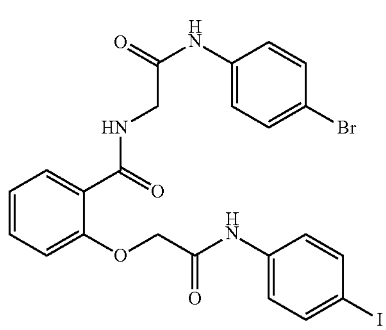 [SMILES: O=C(CNC(=O)c1ccccc1OCC(=O)Nc1ccc(I)cc1)Nc1ccc(Br)cc1] | N-(2-(4-bromophenyl amino)-2-oxoethyl)-2-(2-(4-iodophenyl amino)-2-oxoethoxy)benzamide (CID-46937199) | $^1$H NMR (400 MHz, DMSO) δ 10.48 (s, 1H), 10.25 (s, 1H), 9.05 (t, J = 4.4 Hz, 1H), 7.79 (d, J = 1.6 Hz, 1H), 7.79-7.46 (m, 8H), 7.21 (d, J = 6.4 Hz, 1H), 7.13 (t, J = 0.4 Hz, 1H), 4.90 (s, 2H), 4.14 (d, J = 4.4 Hz, 2H) ppm; $^{13}$C NMR (100 MHz, DMSO) δ 167.7, 166.7, 166.1, 155.8, 155.1, 138.2, 137.4, 132.6, 131.5, 130.3, 121.7, 121.5, 120.0, 114.1, 87.4, 67.9, 43.5, 30.7 ppm; HRMS calcd for $C_{23}H_{19}BrIN_3O_4$ [M + H$^+$] 607.9676, found 607.9677 |

TABLE 2-continued

| Cpd. No. | Structure | Name | Analytical Data |
|---|---|---|---|
| 48 | 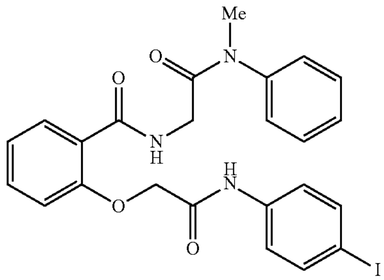 [SMILES: CN(C(=O)CNC(=O)c1ccccc1OCC(=O)Nc1ccc(I)cc1)c1ccccc1] | 2-(2-((4-iodophenyl)amino)-2-oxoethoxy)-N-(2-(methyl(phenyl)amino)-2-oxoethyl)benzamide (CID-46943210) | $^1$H NMR (400 MHz, DMSO) δ 10.84 (s, 1H), 8.84 (t, J = 5.2 Hz, 1H), 7.72 (d, J = 7.2 Hz, 1H), 7.68 (d, J = 8.4 Hz, 2H), 7.49 (d, J = 8.4 Hz, 4H), 7.45 (bs, 4H), 7.18 (d, J = 8 Hz, 1H), 7.09 (t, J = 7.6 Hz, 1H), 4.90 (s, 2H), 3.82 (s, 2H), 3.20 (s, 3H) ppm; ; $^{13}$C NMR (100 MHz, DMSO) 166.6, 165.4, 155.7, 138.1, 137.4, 132.5, 130.3, 123.2, 121.7, 121.5, 113.8, 87.4, 67.8, 41.9, 36.9 ppm; IR $v_{max}$ (cm$^{-1}$) 3307, 3099, 3054, 2919, 1694, 1629; HRMS calcd for C$_{24}$H$_{22}$IN$_3$O$_4$ [M + H$^+$] 495.0794, found 495.0795 |
| 49 | 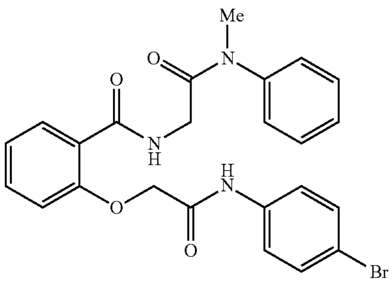 [SMILES: CN(C(=O)CNC(=O)c1ccccc1OCC(=O)Nc1ccc(Br)cc1)c1ccccc1] | 2-(2-((4-bromophenyl)amino)-2-oxoethoxy)-N-(2-(methyl(phenyl)amino)-2-oxoethyl)benzamide (ML266, CID-46943215) | LC-MS Retention Time: 3.295 min; $^1$H NMR (400 MHz, DMSO) δ 10.44 (s, 1H), 8.84 (t, J = 4 Hz, 1H), 7.73 (d, J = 5.6 Hz, 1H), 7.68 (d, J = 6.8 Hz, 2H), 7.50 (d, J = 5.6 Hz, 5H), 7.44 (bs, 3H), 7.17 (d, J = 6.8 Hz, 1H), 7.07 (t, J = 6.4 Hz, 1H), 4.89 (s, 2H), 3.19 (s, 3H) ppm; $^{13}$C NMR (100 MHz, DMSO) δ 167.7, 166.6, 165.5, 155.7, 137.7, 132.5, 131.6, 130.3, 129.8, 128.0, 127.3, 123.2, 121.5, 115.4, 113.8, 67.7, 41.8, 36.9 ppm; IR $v_{max}$ (cm$^{-1}$) 3273, 3061, 2924, 1637, 1594; HRMS calcd for C$_{24}$H$_{22}$BrN$_3$O$_4$ [M + H$^+$] 496.0866, found 496.0876 |
| 50 | 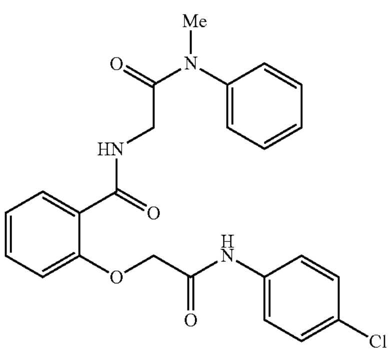 [SMILES: CN(C(=O)CNC(=O)c1ccccc1OCC(=O)Nc1ccc(Cl)cc1)c1ccccc1] | 2-(2-(4-chlorophenylamino)-2-oxoethoxy)-N-(2-(methyl(phenyl)amino)-2-oxoethyl)benzamide (CID-46943225) | $^1$H NMR (400 MHz, DMSO) δ 10.48 (s, 1H), 8.85 (s, 1H), 7.69 (d, J = 7.2 Hz, 2H), 7.43 (m, 10H), 7.16 (d, J = 6.8 Hz, 1H), 7.08 (t, J = 6.0 Hz, 1H), 4.89 (s, 2H), 3.82 (s, 2H), 3.43 (s, 3H) ppm; $^{13}$C NMR (100 MHz, DMSO) δ 167.7, 166.6, 166.2, 165.4, 162.8, 155.7, 139.7, 137.8, 137.3, 132.5, 131.1, 130.6, 130.3, 129.9, 129.5, 128.8, 128.1, 127.5, 127.3, 123.2, 121.5, 121.1, 113.8, 67.7, 36.9 ppm; HRMS calcd for C$_{24}$H$_{22}$ClN$_3$O$_4$ [M + H$^+$] 452.1372, found 452.1367 |
| 51 | 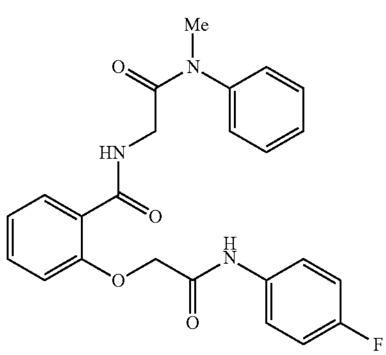 [SMILES: CN(C(=O)CNC(=O)c1ccccc1OCC(=O)Nc1ccc(F)cc1)c1ccccc1] | 2-(2-(4-fluorophenylamino)-2-oxoethoxy)-N-(2-(methyl(phenyl)amino)-2-oxoethyl)benzamide (CID-46937190) | $^1$H NMR (400 MHz, DMSO) δ 10.41 (s, 1H), 8.86 (t, J = 4.8 Hz, 1H), 7.73 (d, J = 7.2 Hz, 1H), 7.67 (m, 2H), 7.51-7.39 (m, 6H), 7.20 (t, J = 8.4 Hz, 4H), 7.08 (td, J = 0.8, 7.2 Hz, 1H), 4.89 (s, 2H), 3.83 (s, 2H), 3.20 (s, 3H) ppm; $^{13}$C NMR (100 MHz, DMSO) δ HRMS calcd for C$_{24}$H$_{22}$FN$_3$O$_4$ [M + H$^+$] 436.1667, found 436.1664 |

TABLE 2-continued

| Cpd. No. | Structure | Name | Analytical Data |
|---|---|---|---|
| 52 | 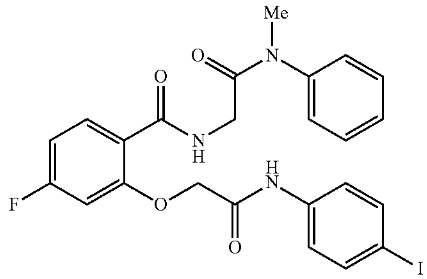 [SMILES: CN(C(=O)CNC(=O)c1ccc(F)cc1OCC(=O)Nc1ccc(I)cc1)c1ccccc1] | 4-fluoro-2-(2-(4-iodophenyl amino)-2-oxoethoxy)-N-(2-(methyl(phenyl)amino)-2-oxoethyl)benzamide (CID-53230304) | $^1$H NMR (400 MHz, DMSO) δ 10.413 (s, 1H), 8.77 (s, 1H), 7.81 (t, J = 6.0 Hz, 1H), 7.69 (d, J = 7.2 Hz, 2H), 7.49-7.36 (m, 9H), 7.14 (dd, J = 1.6, 7.2 Hz, 1H), 6.96 (td, J = 2.0, 4.8 Hz, 1H), 4.94 (s, 2H), 3.79 (s, 2H), 3.19 (s, 3H) ppm; $^{13}$C NMR (100 MHz, DMSO) δ 166.2, 164.4, 138.1, 137.4, 132.5, 129.8, 127.3, 121.7, 108.3, 102.1, 101.8, 87.5, 67.9, 42.1, 36.9 ppm; HRMS calcd for C$_{27}$H$_{29}$BrN$_2$O$_3$ [M + H$^+$] |
| 53 | 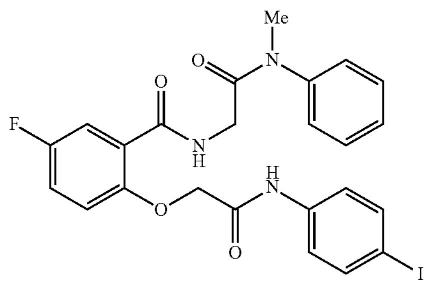 [SMILES: CN(C(=O)CNC(=O)c1cc(F)ccc1OCC(=O)Nc1ccc(I)cc1)c1ccccc1] | 5-fluoro-2-(2-(4-iodophenyl amino)-2-oxoethoxy)-N-(2-(methyl(phenyl)amino)-2-oxoethyl)benzamide (CID-53230298) | $^1$H NMR (400 MHz, DMSO) δ 10.39 (s, 1H), 8.94 (t, J = 4.0 Hz, 1H), 7.69 (d, J = 6.8 Hz, 2H), 7.49-7.34 (m, 9H), 6.55 (m, 1H), 4.89 (s, 2H), 3.81 (s, 2H), 3.19 (s, 3H) ppm; $^{13}$C NMR (100 MHz, DMSO) δ 166.4, 164.0, 157.3, 155.4, 152.1, 138.1, 137.4, 129.8, 128.1, 127.3, 124.4, 124.3, 121.7, 118.9, 118.8, 116.5, 116.3, 114.9, 115.9, 87.4, 68.3, 41.1, 36.9 ppm; HRMS calcd for C$_{24}$H$_{21}$FIN$_3$O$_4$ [M + H$^+$] 562.0634, found 562.0628 |
| 54 | 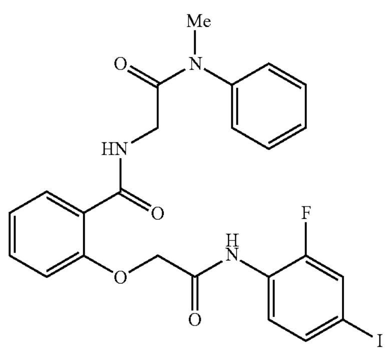 [SMILES: CN(C(=O)CNC(=O)c1ccccc1OCC(=O)Nc1ccc(I)cc1F)c1ccccc1] | 2-(2-((2-fluoro-4-iodophenyl)amino)-2-oxoethoxy)-N-(2-(methyl(phenyl)amino)-2-oxoethyl)benzamide (53230302) | |
| 55 | 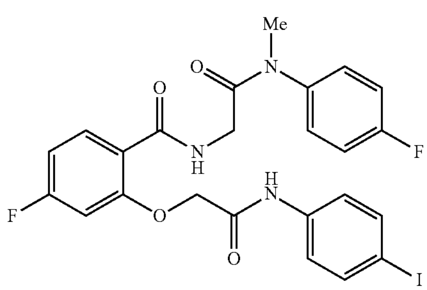 [SMILES: CN(C(=O)CNC(=O)c1ccc(F)cc1OCC(=O)Nc1ccc(I)cc1)c1ccc(F)cc1] | 4-fluoro-N-(2-((4-fluorophenyl)(methyl)amino)-2-oxoethyl)-2-(2-(4-iodophenylamino)-2-oxoethoxy)benzamide (CID-53230294) | $^1$H NMR (400 MHz, DMSO) δ 10.41 (s, 1H), 8.80 (s, 1H), 7.79 (t, J = 6.0 Hz, 1H), 7.68 (d, J = 6.8 Hz, 2H), 7.50-7.34 (m, 6H), 7.14 (dd, 2.0, 6.8 Hz, 1H), 6.96 (td, 1.6, 5.2 Hz, 1H), 4.97 (s, 2H), 6.55 (s, 2H), 3.16 (s, 3H) $^{13}$C NMR (100 MHz, DMSO) δ 166.1, 165.2, 164.4, 163.2, 157.4, 157.3, 138.1, 137.4, 132.5, 132.4, 129.7, 121.7, 119.5, 116.7, 116.5, 108.3, 102.0, 101.8, 87.5, 67.9, 42.1, 34.0 ppm; HRMS calcd for C$_{24}$H$_{20}$F$_2$IN$_3$O$_4$ [M + H$^+$] 580.0539, found 580.0537 |

TABLE 2-continued

| Cpd. No. | Structure | Name | Analytical Data |
|---|---|---|---|
| 56 | 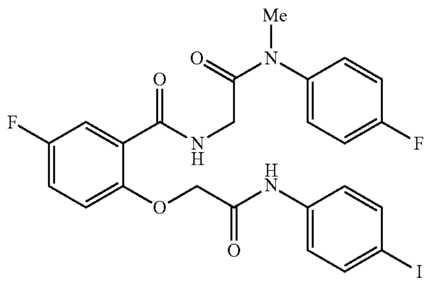 [SMILES: CN(C(=O)CNC(=O)c1cc(F)ccc1OCC(=O)Nc1ccc(I)cc1)c1ccc(F)cc1] | 5-fluoro-N-(2-((4-fluorophenyl)(methyl)amino)-2-oxoethyl)-2-(2-(4-iodophenylamino)-2-oxoethoxy)benzamide (CID-53230310) | $^1$H NMR (400 MHz, DMSO) δ 10.38 (s, 1H), 8.94 (s, 1H), 7.69 (d, J = 6.4 Hz, 2H), 7.48 (m, 5H), 7.2-7.19 (m, 4H), 4.91 (s, 2H), 3.81 (s, 2H), 3.15 (s, 3H) ppm; $^{13}$C NMR (100 MHz, DMSO) δ 167.6, 166.4, 164.0, 157.3, 155.4, 152.1, 138.8, 138.1, 137.4, 129.6, 124.3, 124.2, 121.7, 118.9, 118.8, 116.7, 116.3, 115.9, 115.8, 87.5, 68.3, 42.1, 37.1 ppm; HRMS calcd for $C_{24}H_{20}F_2IN_3O_4$ [M + H$^+$] 580.0539, found 580.0537 |
| 57 | 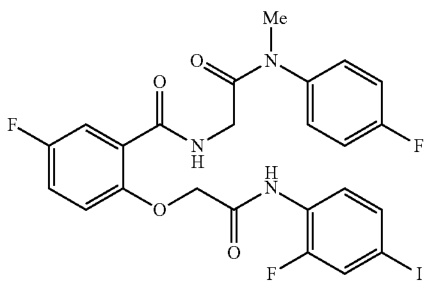 [SMILES: CN(C(=O)CNC(=O)c1cc(F)ccc1OCC(=O)Nc1ccc(I)cc1F)c1ccc(F)cc1] | 5-fluoro-2-(2-(2-fluoro-4-iodophenylamino)-2-oxoethoxy)-N-(2-((4-fluorophenyl)(methyl)amino)-2-oxoethyl)benzamide (CID-53230295) | ): $^1$H NMR (400 MHz, DMSO) δ 10.08 (s, 1H), 8.86 (s, 1H), 7.77-7.67 (m, 2H), 7.61-7.35 (m, 7H), 7.18 (m, 1H), 4.96 (s, 2H), 3.78 (s, 2H), 3.12 (s, 3H) ppm; $^{13}$C NMR (100 MHz, DMSO) δ 166.6, 163.6, 157.3, 155.4, 151.9, 133.5, 133.4, 133.3, 129.7, 127.3, 126.1, 124.7, 124.5, 124.3, 124.2, 118.9, 118.7, 116.7, 116.4, 115.6, 115.5, 68.0, 42.1, 36.9 ppm; HRMS calcd for $C_{27}H_{29}BrN_2O_3$ [M + H$^+$] 598.0445, found 598.0444 |
| 58 | 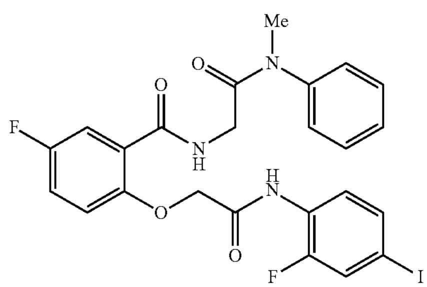 [SMILES: CN(C(=O)CNC(=O)c1cc(F)ccc1OCC(=O)Nc1ccc(I)cc1F)c1ccccc1] | 5-fluoro-2-(2-(2-fluoro-4-iodophenyl amino)-2-oxoethoxy)-N-(2-(methyl(phenyl)amino)-2-oxoethyl)benzamide (CID-53230314) | $^1$H NMR (400 MHz, DMSO) δ 10.08 (s, 1H), 8.86 (t, J = 4.0 Hz, 1H), 7.77-7.68 (m, 2H), 7.59-7.34 (m, 9H), 7.19 (q, 3.6 Hz, 1H), 4.96 (s, 2H), 3.79 (s, 2H), 3.43 (s, 3H), 3.01 (s, 1H) ppm; $^{13}$C NMR (100 MHz, DMSO) δ 167.6, 166.6, 163.6, 157.3, 155.4, 154., 152.6, 151.9, 133.5, 133.4, 129.9, 128.1, 127.3, 126.1, 125.4, 124.3, 124.2, 118.9, 118.7, 116.5, 115.4, 88.34, 68.0, 41.9, 36.9 ppm; HRMS calcd for $C_{24}H_{20}F_2IN_3O_4$ [M + H$^+$] 580.0539, found 580.0538 |
| 59 | 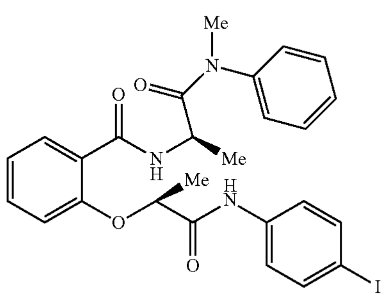 [SMILES: C[C@H](Oc1ccccc1C(=O)N[C@H](C)C(=O)N(C)c1ccccc1)C(=O)Nc1ccc(I)cc1] | 2(((S)-1-((4-iodophenyl)amino)-1-oxopropan-2-yl)oxy)-N-((R)-1-(methyl(phenyl)amino)-1-oxopropan-2-yl)benzamide (CID-53230311) | $^1$H NMR (400 MHz, DMSO) δ 10.64 (s, 1H), 8.87 (t, J = 5.2 Hz, 1H), 7.68 (d, J = 6.8 Hz, 3H), 7.51-7.42 (m, 8H), 7.14 (d, J = 6.4 Hz, 1H), 7.08 (t, J = 6.0 Hz, 1H), 5.17 (q, J = 5.2 Hz, 1H), 5.15 (q, J = 5.2 Hz, 1H), 1.66 (d, J = 5.6 Hz, 3H), 1.17 (d, J = 5.2 Hz, 3H) ppm; $^{13}$C NMR (100 MHz, DMSO) δ 171.7, 169.9, 164.9, 155.0, 142.9, 138.2, 137.4, 132.4, 130.5, 129.7, 127.9, 123.6, 121.8, 121.7, 121.4, 113.9, 87.5, 74.6, 45.8, 34.3, 18.6, 17.5 ppm; HRMS calcd for $C_{26}H_{26}IN_3O_4$ [M + H$^+$] 572.1041, found 572.1036 |

TABLE 2-continued

| Cpd. No. | Structure | Name | Analytical Data |
|---|---|---|---|
| 60 | 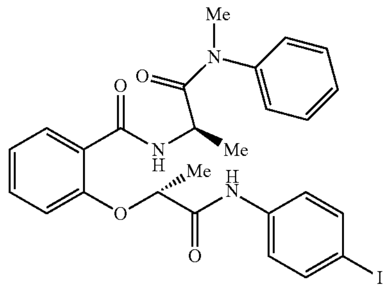 [SMILES: C[C@@H](NC(=O)c1ccccc1O[C@H](C)C(=O)Nc1ccc(I)cc1)C(=O)N(C)c1ccccc1] | 2-((R)-1-(4-iodophenyl amino)-1-oxopropan-2-yloxy)-N-((R)-1-oxo-1-(p-tolylamino)propan-2-yl)benzamide (CID-53230313) | $^1$H NMR (400 MHz, DMSO) δ 10.55 (s, 1H), 8.81 (s, 1H), 7.71 (m, 3H), 7.47 (m, 8H), 7.09 (m, 2H), 5.16 (q, J = 6.0 Hz, 1H), 4.54 (q, J = 5.2 Hz, 1H), 3.41 (s, 3H), 1.65 (d, J = 5.2 Hz, 3H), 1.17 (d, J = 5.2 Hz, 3H) ppm; $^{13}$C NMR (100 MHz, DMSO) δ 171.6, 169.8, 164.8, 154.9, 138.2, 138.1, 137.4, 130.7, 129.8, 127.5, 123.5, 121.8, 113.9, 87.5, 74.6, 45.8, 40.0, 37.3, 18.5 ppm; HRMS calcd for $C_{26}H_{26}IN_3O_4$ [M + H$^+$] 572.1041, found 572.1037 |
| 60a | 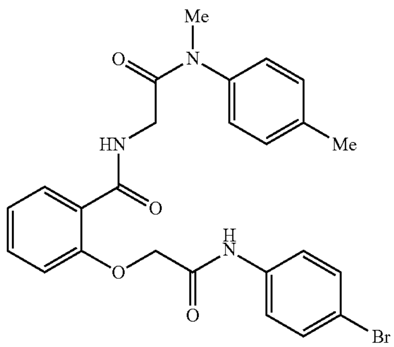 [SMILES: Cc1ccc(N(C)C(=O)CNC(=O)c2ccccc2OCC(=O)Nc2ccc(Br)cc2)cc1] | 2-(2-(4-bromophenylamino)-2-oxoethoxy)-N-(2-(methyl(p-tolyl)amino)-2-oxoethyl)benzamide (CID-46937196) | $^1$H NMR (400 MHz, DMSO) δ 10.53 (s, 1H), 10.01 (s, 1H), 9.03 (t, J = 4.4 Hz, 1H), 7.79 (dd, J = 1.2, 4.8 Hz, 1H), 7.61 (d, J = 7.2 Hz, 2H), 7.53 (td, J = 1.6, 4.4 Hz, 1H), 7.47 (d, J = 7.2 Hz, 2H), 7.39 (d, J = 7.2 Hz, 2H), 7.21 (d, J = 6.4 Hz, 1H), 7.14 (dd, J = 0.8, 5.6 Hz, 1H), 7.10 (d, J = 7.2 Hz, 2H), 4.91 (s, 2H), 4.13 (d, J = 4.4 Hz, 2H), 2.09 (s, 3H) ppm; $^{13}$C NMR (100 MHz, DMSO) δ 167.2, 166.8, 166.1, 155.8, 137.6, 132.5, 132.1, 131.5, 130.3, 129.1, 123.4, 121.5, 119.1, 114.3, 114.1, 67.9, 43.4, 20.4 ppm; HRMS calcd for $C_{27}H_{29}BrN_2O_3$ [M + H$^+$] 496.0866, found 496.0862 |
| 61 | 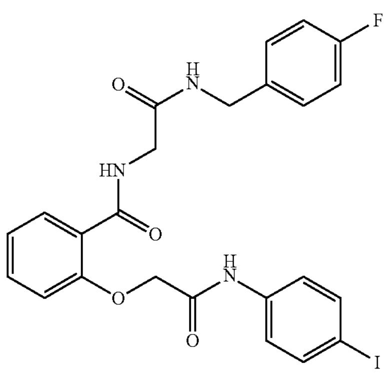 [SMILES: O=C(CNC(=O)c1ccccc1OCC(=O)Nc1ccc(I)cc1)NCc1ccc(F)cc1] | N-(2-(4-fluorobenzyl amino)-2-oxoethyl)-2-(2-(4-iodophenyl amino)-2-oxoethoxy)benzamide (CID-50985712) | $^1$H NMR (400 MHz, DMSO) δ 10.49 (s, 1H), 8.99 (t, J = 6.0 Hz, 1H), 8.47 (t, J = 6.0 Hz, 1H), 7.79 (dd, J = 1.6, 4.8, 1H), 7.63 (d, J = 5.6 Hz, 2H), 7.52-7.48 (m, 3H), 7.31-7.28 (m, 2H), 7.17 (d, J = 6.8 Hz, 1H), 7.13-7.07 (m, 3H), 4.89 (s, 2H), 4.29 (d, J = 4.8 Hz, 2H), 3.99 (d, J = 4.4 Hz, 2H) ppm; $^{13}$C NMR (100 MHz, DMSO) δ 168.8, 166.8, 165.9, 162.0, 160.1, 155.7, 138.1, 137.4, 135.5, 132.5, 130.3, 129.0, 123.5, 121.7, 114.9, 114.8, 113.9, 87.4, 67.8, 42.8, 41.3 ppm; HRMS calcd for $C_{24}H_{21}FIN_3O_4$ [M + H$^+$] 562.0579, found 562.0667 |
| 62 | 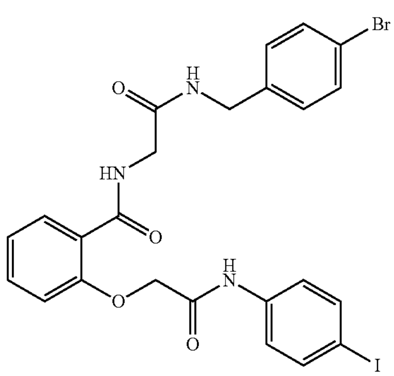 | N-(2-((4-bromobenzyl)amino)-2-oxoethyl)-2-(2-((4-iodophenyl)amino)-2-oxoethoxy)benzamide | |

TABLE 2-continued

| Cpd. No. | Structure | Name | Analytical Data |
|---|---|---|---|
| 63 | 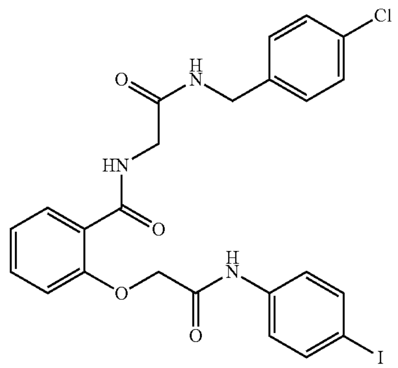 [SMILES: O=C(CNC(=O)c1ccccc1OCC(=O)Nc1ccc(I)cc1)NCc1ccc(Cl)cc1] | N-(2-(4-chlorobenzyl amino)-2-oxoethyl)-2-(2-(4-iodophenyl amino)-2-oxoethoxy)benzamide (CID-50985718) | $^1$H NMR (400 MHz, DMSO) δ 10.49 (s, 1H), 9.01 (t, J = 5.6 Hz, 1H), 8.51 (t, J = 5.6 Hz, 1H), 7.79 (dd, J = 1.2, 4.8 Hz, 1H), 7.64 (d, J = 4.0 Hz, 2H), 7.53-7.47 (m, 3H), 7.32-7.27 (m, 4H), 7.19 (d, J = 6.4 Hz, 1H), 7.13 (td, J = 0.4, 5.6 Hz, 1H), 4.89 (s, 2H), 4.30 (d, J = 4.8 Hz, 2H), 4.00 (d, J = 4.4 Hz, 2H) ppm; $^{13}$C NMR (100 MHz, DMSO) δ 168.9, 166.8, 165.9, 155.7, 138.4, 138.1, 137.4, 132.5, 131.2, 130.4, 128.9, 128.1, 123.5, 121.7, 113.9, 87.4, 67.8, 42.8, 41.4 ppm; HRMS calcd for $C_{24}H_{21}ClIN_3O_4$ [M + H$^+$] 578.0338, found 578.0364 |
| 64 | 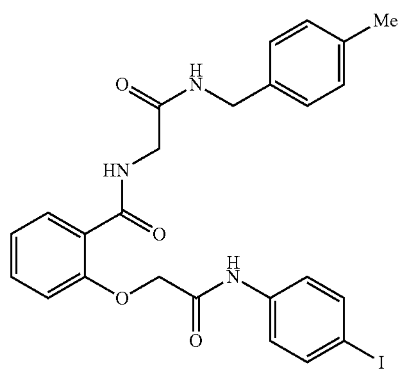 [SMILES: Cc1ccc(CNC(=O)CNC(=O)c2ccccc2OCC(=O)Nc2ccc(I)cc2)cc1] | 2-(2-(4-iodophenyl amino)-2-oxoethoxy)-N-(2-(4-methyl benzylamino)-2-oxoethyl) benzamide (CID-50985705) | $^1$H NMR (400 MHz, DMSO) δ 10.55 (s, 1H), 9.04 (t, J = 6.0 Hz, 1H), 8.46 (t, J = 6.0 Hz, 1H), 7.84 (dd, J = 1.2, 4.8 Hz, 1H), 7.68 (d, J = 7.2 Hz, 2H), 7.55 (m, 3H), 7.24 (d, J = 6.4 Hz, 1H), 7.29 (d, J = 6.4 Hz, 2H), 7.17 (dd, J = 0.8, 5.6 Hz, 1H), 7.13 (d, J = 6.0 Hz, 2H), 4.94 (s, 2H), 4.32 (d, J = 4.8 Hz, 2H), 4.05 (d, J = 4.8 Hz, 2H), 2.31 (s, 3H) ppm; $^{13}$C NMR (100 MHz, DMSO) δ 168.7, 166.8, 165.9, 155.7, 138.1, 137.4, 136.2, 135.7, 132.4, 130.3, 128.7, 127.0, 123.6, 121.7, 121.5, 113.9, 87.4, 67.9, 42.8, 41.8, 20.7 ppm; HRMS calcd for $C_{25}H_{24}IN_3O_4$ [M + H$^+$] 558.00, found 558.08 |
| 65 | 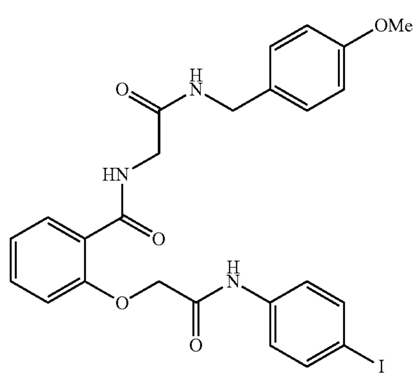 [SMILES: COc1ccc(CNC(=O)CNC(=O)c2ccccc2OCC(=O)Nc2ccc(I)cc2)cc1] | 2-(2-(4-iodopheny lamino)-2-oxoethoxy)-N-(2-(4-methoxy benzylamino)-2-oxoethyl)benzamide (CID-50985690) | $^1$H NMR (400 MHz, DMSO) δ 10.50 (s, 1H), 8.97 (t, J = 5.6 Hz, 1H), 8.38 (t, J = 5.6 Hz, 1H), 7.78 (dd, J = 1.2, 4.8 Hz, 1H), 7.64 (d, J = 4.0 Hz, 2H), 7.50 (d, J = 4.0 Hz, 3H), 7.19 (d, J = 5.2 Hz, 3H), 7.13 (d, J = 0.4, 5.2 Hz, 1H), 6.84 (d, J = 5.2 Hz, 2H), 4.88 (s, 2H), 4.24 (d, J = 4.8 Hz, 2H), 3.97 (d, J = 4.8 Hz, 2H), 3.71 (s, 3H) ppm; $^{13}$C NMR (100 MHz, DMSO) δ 168.6, 166.8, 165.9, 158.1, 155.7, 138.1, 137.4, 132.4, 131.2, 130.3, 128.5, 128.4, 123.6, 121.7, 121.5, 113.9, 113.6, 87.4, 67.8, 44.0, 42.8, 41.5 ppm; HRMS calcd for $C_{25}H_{24}IN_3O_5$ [M + H$^+$] 573.0833, found 574.0852 |

TABLE 2-continued

| Cpd. No. | Structure | Name | Analytical Data |
|---|---|---|---|
| 65a | 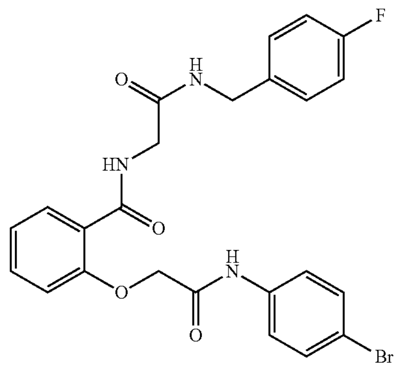 [SMILES: O=C(CNC(=O)c1ccccc1OCC(=O)Nc1ccc(Br)cc1)NCc1ccc(F)cc1] | 2-(2-(4-bromophenyl amino)-2-oxoethoxy)-N-(2-(4-fluorobenzyl amino)-2-oxoethyl)benzamide (CID-50985689) | $^1$H NMR (400 MHz, DMSO) δ 10.54 (s, 1H), 8.99 (t, J = 6.0 Hz, 1H), 8.48 (t, J = 6.0 Hz, 1H), 8.79 (dd, J = 1.2, 4.8 Hz, 1H), 7.62 (d, J = 3.6 Hz, 2H), 7.49 (m, 3H), 7.31 (m, 2H), 7.19 (d, J = 6.4 Hz, 1H), 7.09 (m, 3H), 4.90 (s, 2H), 4.32 (d, J = 4.8 Hz, 2H), 4.01 (d, J = 4.8 Hz, 2H) ppm; $^{13}$C NMR (100 MHz, DMSO) δ 168.8, 166.8, 165.9, 162.0, 155.7, 137.6, 135.5, 132.5, 131.6, 131.5, 130.4, 129.0, 128.9, 123.5, 121.5, 121.2, 115.4, 114.9, 113.9, 67.8, 42.8, 41.3 ppm; HRMS calcd for $C_{24}H_{21}BrFN_3O_4$ [M + H$^+$] 559.0, found 559.0 |
| 65b | 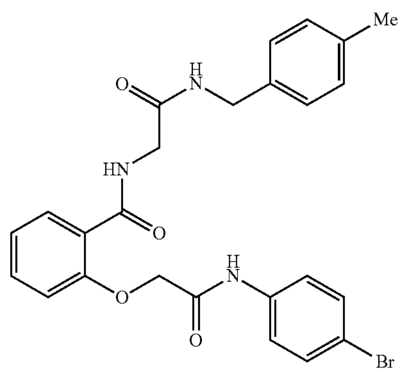 [SMILES: Cc1ccc(CNC(=O)CNC(=O)c2ccccc2OCC(=O)Nc2ccc(Br)cc2)cc1] | 2-(2-(4-bromophenyl amino)-2-oxoethoxy)-N-(2-(4-methyl benzylamino)-2-oxoethyl)benzamide (CID-50985707) | $^1$H NMR (400 MHz, DMSO) δ 10.53 (s, 1H), 8.98 (t, J = 4.8 Hz, 1H), 8.41 (t, J = 4.8 Hz, 1H), 7.87 (dd, J = 1.6, 4.8 Hz, 1H), 7.65 (d, J = 7.2 Hz, 2H), 7.52 (td, J = 1.6, 4.4 Hz, 1H), 7.48 (d, J = 7.2 Hz, 2H), 7.19 (d, J = 6.4 Hz, 1H), 7.13 (d, J = 6.4 Hz, 2H), 7.12 (td, J = 0.4, 6.0 Hz, 1H), 7.06 (d, J = 6.4 Hz, 2H), 4.89 (s, 2H), 4.27 (d, J = 4.8 Hz, 2H), 3.99 (d, J = 4.8 Hz, 2H), 2.26 (s, 3H) ppm; $^{13}$C NMR (100 MHz, DMSO) δ 168.7, 166.8, 165.9, 155.7, 137.6, 136.2, 135.7, 132.4, 131.66. 130.3, 128.7, 127.1, 123.6, 121.5, 115.4, 113.9, 67.8, 42.8, 41.8, 20.6 ppm; HRMS calcd for $C_{25}H_{24}BrN_3O_4$ [M + H$^+$] 510.1023, found 510.1039 |
| 66 | 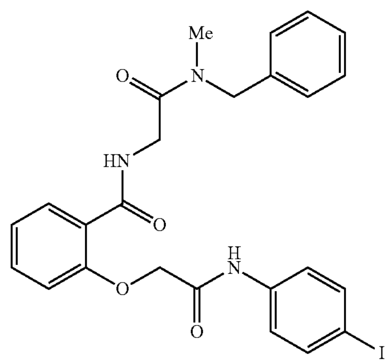 [SMILES: CN(Cc1ccccc1)C(=O)CNC(=O)c1ccccc1OCC(=O)Nc1ccc(I)cc1] | N-(2-(benzyl(methyl)amino)-2-oxoethyl)-2-(2-((4-iodophenyl)amino)-2-oxoethoxy)benzamide (CID-50985691) | $^1$H NMR (400 MHz, DMSO) δ 10.48 (s, 1H), 8.90 (t, J = 6.0 Hz, 1H), 7.81 (dd, J = 1.6, 4.4 Hz, 1H), 7.63 (m, 2H), 7.52-7.49 (m, 3H), 7.39 (t, J = 6.0 Hz, 1H), 7.33-7.13 (m, 5H), 7.12 (t, J = 5.6 Hz, 1H) ppm; $^{13}$C NMR (100 MHz, DMSO) δ 168.4, 168.3, 166.6, 165.7, 155.6, 138.1, 137.4, 137.4, 137.0, 132.4, 130.4, 130.3, 128.7, 127.4, 127.3, 127.0, 126.7, 123.5, 121.9, 113.9, 87.4, 67.8, 51.5, 41.3, 41.3, 33.8, 33.7 ppm; HRMS calcd for $C_{25}H_{24}IN_3O_4$ [M + H$^+$] 558.0811, 558.0919 |

TABLE 2-continued

| Cpd. No. | Structure | Name | Analytical Data |
|---|---|---|---|
| 67 | 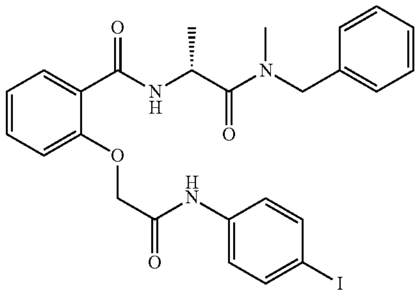 [SMILES: C[C@@H](NC(=O)c1ccccc1OCC(=O)Nc1ccc(I)cc1)C(=O)N(C)Cc1ccccc1] | (R)-N-(1-(benzyl(methyl)amino)-1-oxopropan-2-yl)-2-(2-((4-iodophenyl)amino)-2-oxoethoxy)benzamide (CID-50985713) | $^1$H NMR (400 MHz, DMSO) δ 10.56 (s, 1H), 8.98 (s, 1H), 7.74 (dd, J = 1.2, 4.8 Hz, 1H), 7.76 (d, J = 5.2 Hz, 2H), 7.62 (m, 3H), 7.34 (s, 1H), 7.304 (d, J = 5.2 Hz, 1H), 7.25 (m, 3H), 7.10 (m, 1H), 3.05 (s, 3H), 1.38 (d, J = 5.6 Hz, 3H) ppm; $^{13}$C NMR (100 MHz, DMSO) δ 172.3, 166.6, 165.1, 137.4, 137.2, 132.5, 130.4, 128.6, 128.4, 127.2, 121.7, 121.7, 113.8, 87.4, 67.9, 52.1, 50.3, 40.4, 34.5, 33.4, 17.7, 16.9 ppm; IR $v_{max}$ (cm$^{-1}$) 3264, 3058, 1702, 1678; HRMS calcd for C$_{26}$H$_{26}$IN$_3$O$_4$ [M + H$^+$] 572.1041, found 572.1041 |
| 68 | 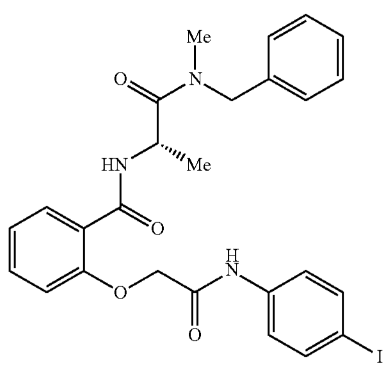 [SMILES: C[C@H](NC(=O)c1ccccc1OCC(=O)Nc1ccc(I)cc1)C(=O)N(C)Cc1ccccc1] | (S)-N-(1-(benzyl(methyl)amino)-1-oxopropan-2-yl)-2-(2-(4-iodophenyl amino)-2-oxoethoxy)benzamide (CID-50985694) | $^1$H NMR (400 MHz, DMSO) δ 10.56 (s, 1H), 8.97 (t, J = 6.0 Hz, 1H), 7.77 (dd, J = 1.2, 4.8 Hz, 1H), 7.63 (m, 2H), 7.52 (m, 2H), 7.34 (m, 3H), 7.34-7.28 (m, 3H), 7.22 (m, 3H), 7.11 (m, 1H), 4.99 (m, 1H), 4.88 (s, 2H), 4.54 (q, J = 6.0 Hz, 2H), 3.05 (s, 2H), 2.77 (s, 1H), 1.37 (d, J = 5.6 Hz, 3H) ppm; ($^{13}$C NMR (100 MHz, DMSO) δ 172.3, 172.1, 166.6, 165.1, 155.6, 138.2, 137.4, 132.5, 130.4, 128.6, 128.4, 127.3, 127.2, 123.3, 121.7, 121.4, 113.8, 113.7, 87.4, 67.0, 42.1, 40.3, 45.6, 34.5, 33.4, 17.7, 16.9 ppm; HRMS calcd for C$_{26}$H$_{26}$IN$_3$O$_4$ [M + H$^+$] |
| 69 | 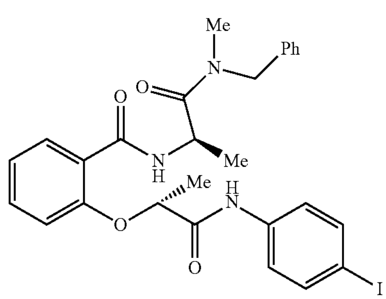 [SMILES: C[C@@H](NC(=O)c1ccccc1O[C@H](C)C(=O)Nc1ccc(I)cc1)C(=O)N(C)Cc1ccccc1] | N-((R)-1-(benzyl (methyl)amino)-1-oxopropan-2-yl)-2-(((R)-1-((4-iodophenyl)amino)-1-oxopropan-2-yl)oxy)benzamide (CID-53230312) | $^1$H NMR (400 MHz, DMSO) δ 10.64 (s, 1H), 9.01 (m, 1H), 7.74 (m, 1H), 7.63 (m, 2H), 7.51 (m, 3H), 7.32-7.25 (m, 5H), 7.15-7.08 (m, 2H), 5.19 (m, 1H), 5.04 (m, 1H), 4.79-4.47 (m, 2H), 3.06 (s, 2H), 1.62 (d, J = 2.8 Hz, 3H), 1.32 (d, J = 5.2 Hz, 3H) ppm; $^{13}$C NMR (100 MHz, DMSO) δ 172.1, 169.9, 165.1, 154.9, 137.4, 132.4, 130.5, 128.5, 127.3, 127.3, 121.4, 113.8, 87.5, 74.5, 52.1, 50.3, 45.6, 42.1, 34.6, 33.5, 18.5, 17.4 ppm; HRMS calcd for C$_{27}$H$_{28}$IN$_3$O$_4$ [M + H$^+$] 586.1197, found 586.1192 |

TABLE 2-continued

| Cpd. No. | Structure | Name | Analytical Data |
|---|---|---|---|
| 70 | 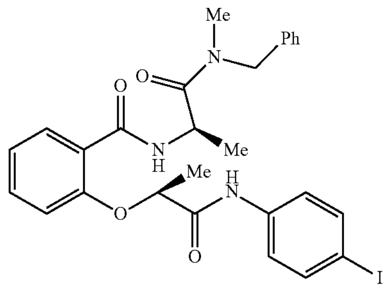 [SMILES: C[C@H](Oc1ccccc1C(=O)N[C@H](C)C(=O)N(C)Cc1ccccc1)C(=O)Nc1ccc(I)cc1] | N-((R)-1-(benzyl(methyl)amino)-1-oxopropan-2-yl)-2-((S)-1-(4-iodophenylamino)-1-oxopropan-2-yloxy)benzamide (CID-53230309) | $^1$H NMR (400 MHz, DMSO) δ 10.65 (s, 1H), 9.05 (m, 1H), 7.76 (dd, J = 1.2, 4.8 Hz, 1H), 7.59 (d, J = 6.0 Hz, 2H), 7.48 (m, 3H), 7.36-7.23 (m, 5H), 7.15 (d, J = 6.4 Hz, 1H), 7.09 (m, 1H), 5.17-5.02 (m, 2H), 4.82-4.50 (m, 2H), 3.00 (s, 2H), 1.64 (d, J = 5.6 Hz, 3H), 1.31 (d, J = 5.2 Hz, 3H) ppm; $^{13}$C NMR (100 MHz, DMSO) δ 172.1, 169.9, 165.1, 155.1, 155.0, 138.2, 138.2, 137.4, 137.3, 132.4, 130.5, 128.7, 128.5, 127.3, 127.2, 127.0, 126.8, 123.7, 121.7, 113.9, 87.4, 74.6, 42.1, 50.3, 45.5, 34.5, 33.5, 18.6, 18.1 ppm; HRMS calcd for $C_{27}H_{28}IN_3O_4$ [M + H$^+$] 586.1197, found 586.1193 |
| 71 | 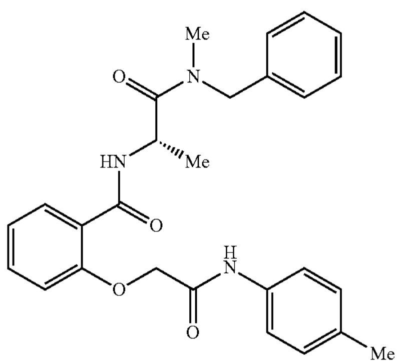 [SMILES: Cc1ccc(NC(=O)COc2ccccc2C(=O)N[C@@H](C)C(=O)N(C)Cc2ccccc2)cc1] | (S)-N-(1-(benzyl (methyl)amino)-1-oxopropan-2-yl)-2-(2-oxo-2-(p-tolylamino)ethoxy)benzamide (CID-50985688) | $^1$H NMR (400 MHz, DMSO) δ 10.34 (s, 1H), 8.99 (t, J = 5.6 Hz, 1H), 7.77 (dd, J = 1.6, 4.8 Hz, 1H), 7.57-7.49 (m, 3H), 7.34 (d, J = 3.6 Hz, 1H), 7.25-7.17 (m, 3H), 7.13 (m, 3H), 4.98 (m, 1H), 4.86 (s, 2H), 4.53 (s, 1H), 3.34 (s, 2H), 3.05 (s, 2H), 2.77 (s, 1H), 2.25 (s, 3H), 1.32 (m, 3H) ppm; 172.3, 166.1, 165.11, 155.7, 137.4, 137.2, 135.8, 132.6, 130.4, 129.1, 128.6, 127.3, 126.9, 123.3, 121.4, 119.5, 113.7, 67.8, 52.1, 50.3, 45.6, 20.4, 17.7, 16.9 ppm; $^{13}$C NMR (100 MHz, DMSO) δ HRMS calcd for $C_{27}H_{29}BrN_2O_3$ [M + H$^+$] 459.22, found 459. |
| 72 | 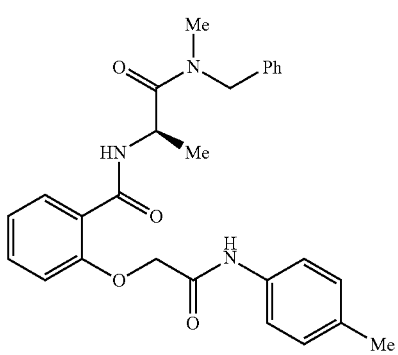 [SMILES: Cc1ccc(NC(=O)COc2ccccc2C(=O)N[C@H](C)C(=O)N(C)Cc2ccccc2)cc1] | (R)-N-(1-(benzyl(methyl)amino)-1-oxopropan-2-yl)-2-(2-oxo-2-(p-tolylamino)ethoxy)benzamide (CID-50985699) | $^1$H NMR (400 MHz, DMSO) δ 10.35 (s, 1H), 8.99 (t, J = 6.0 Hz, 1H), 7.77 (dd, J = 1.2, 4.8 Hz, 1H), 7.57-7.49 (m, 3H), 7.35 (d, J = 3.2 Hz, 1H), 7.31 (d, J = 5.2 Hz, 2H), 7.25-7.17 (m, 3H), 7.13-7.08 (m, 3H), 4.99 (m, 1H), 4.87 (s, 2H), 4.53 (s, 2H), 2.77 (s, 3H), 2.25 (s, 3H), 1.37 (d, J = 5.2 Hz, 3H) ppm; $^{13}$C NMR (100 MHz, DMSO) δ 172.3, 166.1, 165.1, 155.7, 137.4, 137.2, 135.8, 132.6, 130.4, 129.1, 128.6, 128.4, 127.2, 123.3, 121.4, 119.5, 113.7, 113.6, 67.8, 52.1, 50.3, 45.6, 34.5, 20.4, 17.7, 16.9 ppm; HRMS calcd for $C_{27}H_{29}N_3O_4$ [M + H$^+$] 460.22, found 460.22 |

TABLE 2-continued

| Cpd. No. | Structure | Name | Analytical Data |
|---|---|---|---|
| 73 | 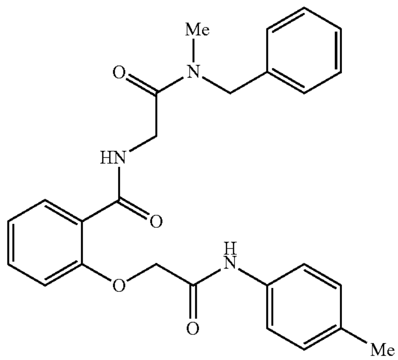 [SMILES: Cc1ccc(NC(=O)COc2ccccc2C(=O)NCC(=O)N(C)Cc2ccccc2)cc1] | N-(2-(benzyl(methyl)amino)-2-oxoethyl)-2-(2-oxo-2-(p-tolylamino)ethoxy)benzamide (CID-50985714) | $^1$H NMR (400 MHz, DMSO) δ 10.28 (s, 1H), 8.91 (t, J = 6.0 Hz, 1H), 7.81 (d, J = 1.2, 4.8 Hz, 1H), 7.54 (d, J = 6.8 Hz, 3H), 7.39 (t, J = 6.0 Hz, 1H), 7.33-7.08 (m, 7H), 4.89 (d, J = 6.8 Hz, 2H), 4.54 (s, 3H), 4.28 (d, J = 4.4 Hz, 2H), 2.99 (s, 3H), 2.45 (d, J = 5.2 Hz, 3H ppm; $^{13}$C NMR (100 MHz, DMSO) δ 168.4, 168.3, 166.2, 166.1, 165.6, 155.7, 137.4, 137.0, 135.7, 132.7, 130.4, 129.1, 128.7, 128.3, 127.4, 127.0, 126.6, 123.5, 123.5, 119.7, 113.8, 67.7, 51.5, 50.3, 41.3, 33.8, 20.5 ppm; HRMS calcd for $C_{26}H_{27}N_3O_4$ [M + H$^+$] 445.2, found 445.2 |
| 74 | 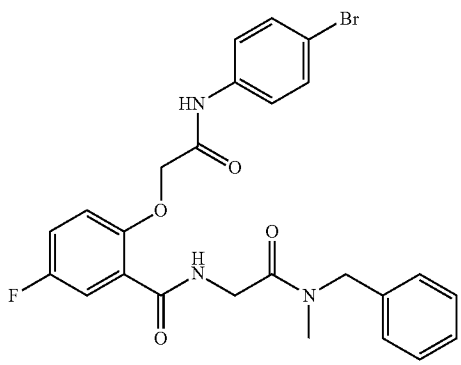 | 2-(2-((4-bromo-2,6-dimethylphenyl)amino)-2-oxoethoxy)-5-fluoro-N-(2-((4-fluorobenzyl)(methyl)amino)-2-oxoethyl)benzamide | calcd for $C_{27}H_{27}BrF_2N_3O_4$ [M + H$^+$] 574.1, found 574.1 |
| 75 | 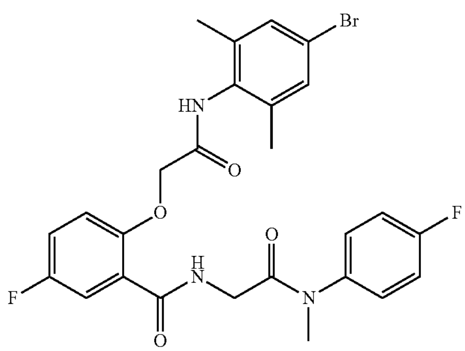 [SMILES: Cc1cc(Br)cc(C)c1NC(=O)COc1ccc(F)cc1C(=O)NCC(=O)N(C)c1ccc(F)cc1] | 2-(2-((4-bromo-2,6-dimethylphenyl)amino)-2-oxoethoxy)-5-fluoro-N-(2-((4-fluorophenyl)(methyl)amino)-2-oxoethyl)benzamide | calcd for $C_{26}H_{25}BrF_2N_3O_4$ [M + H$^+$] 560.1, found 560.1 |
| 76 | 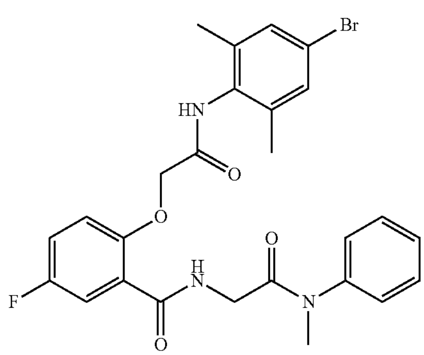 [SMILES: Cc1cc(Br)cc(C)c1NC(=O)COc1ccc(F)cc1C(=O)NCC(=O)N(C)c1ccccc1] | 2-(2-((4-bromo-2,6-dimethylphenyl)amino)-2-oxoethoxy)-5-fluoro-N-(2-(methyl(phenyl)amino)-2-oxoethyl)benzamide | calcd for $C_{26}H_{26}BrFN_3O_4$ [M + H$^+$] 541.1, found 542.1 |

TABLE 2-continued

| Cpd. No. | Structure | Name | Analytical Data |
|---|---|---|---|
| 77 | 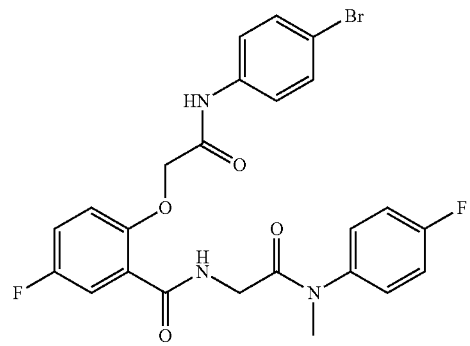 [SMILES: CN(C(=O)CNC(=O)c1cc(F)ccc1OCC(=O)Nc1ccc(Br)cc1)c1ccc(F)cc1] | 2-(2-((4-bromophenyl)amino)-2-oxoethoxy)-5-fluoro-N-(2-((4-fluorophenyl)(methyl)amino)-2-oxoethyl)benzamide | calcd for $C_{24}H_{21}BrFN_3O_4$ [M + H$^+$] 532.1, found 532.1 |
| 78 | 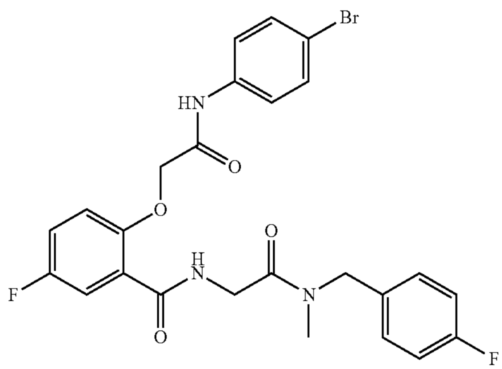 [SMILES: CN(Cc1ccc(F)cc1)C(=O)CNC(=O)c1cc(F)ccc1OCC(=O)Nc1ccc(Br)cc1] | 2-(2-((4-bromophenyl)amino)-2-oxoethoxy)-5-fluoro-N-(2-((4-fluorobenzyl)(methyl)amino)-2-oxoethyl)benzamide | calcd for $C_{25}H_{23}BrF_2N_3O_4$ [M + H$^+$] 546.1, found 546.1 |
| 79 | 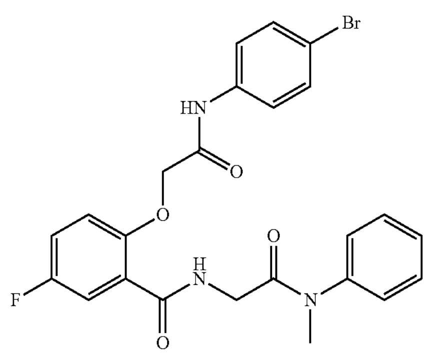 [SMILES: CN(C(=O)CNC(=O)c1cc(F)ccc1OCC(=O)Nc1ccc(Br)cc1)c1ccccc1] | 2-(2-((4-bromophenyl)amino)-2-oxoethoxy)-5-fluoro-N-(2-(methyl(phenyl)amino)-2-oxoethyl)benzamide | calcd for $C_{24}H_{22}BrFN_3O_4$ [M + H$^+$] 514.1, found 514.1 |
| 80 | 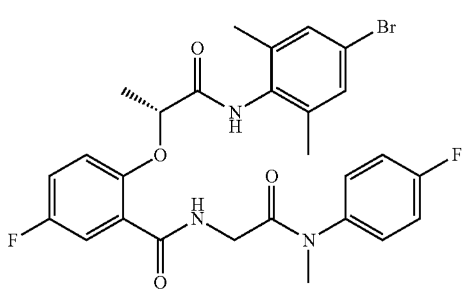 [SMILES: Cc1cc(Br)cc(C)c1NC(=O)[C@@H](C)Oc1ccc(F)cc1C(=O)NCC(=O)N(C)c1ccc(F)cc1] | (R)-2-((1-((4-bromo-2,6-dimethylphenyl)amino)-1-oxopropan-2-yl)oxy)-5-fluoro-N-(2-((4-fluorophenyl)(methyl)amino)-2-oxoethyl)benzamide | calcd for $C_{27}H_{27}BrF_2N_3O_4$ [M + H$^+$] 574.1, found 574.1 |

TABLE 2-continued

| Cpd. No. | Structure | Name | Analytical Data |
|---|---|---|---|
| 81 | 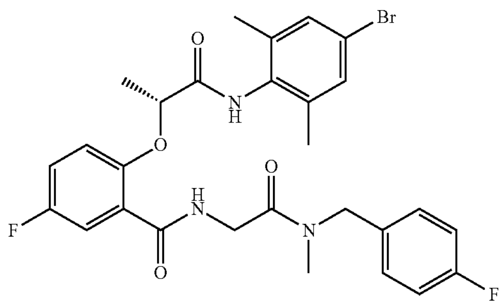 | (R)-2-((1-((4-bromo-2,6-dimethylphenyl)amino)-1-oxopropan-2-yl)oxy)-5-fluoro-N-(2-((4-fluorobenzyl)(methyl)amino)-2-oxoethyl)benzamide | calcd for $C_{28}H_{29}BrF_2N_3O_4$ [M + H$^+$] 588.1, found 588.1 |
| 82 | 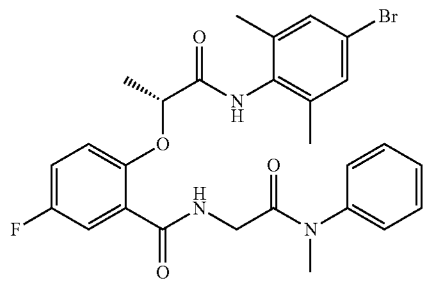 [SMILES: Cc1cc(Br)cc(C)c1NC(=O)[C@@H](C)Oc1ccc(F)cc1C(=O)NCC(=O)N(C)c1ccccc1] | (R)-2-((1-((4-bromo-2,6-dimethylphenyl)amino)-1-oxopropan-2-yl)oxy)-5-fluoro-N-(2-(methyl(phenyl)amino)-2-oxoethyl)benzamide | calcd for $C_{27}H_{28}BrFN_3O_4$ [M + H$^+$] 556.1, found 556.1 |
| 83 | 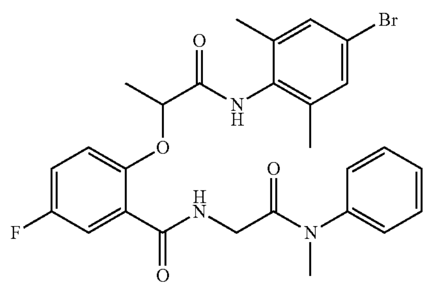 [SMILES: Cc1cc(Br)cc(C)c1NC(=O)C(C)Oc1ccc(F)cc1C(=O)NCC(=O)N(C)c1ccccc1] | 2-((1-((4-bromo-2,6-dimethylphenyl)amino)-1-oxopropan-2-yl)oxy)-5-fluoro-N-(2-(methyl(phenyl)amino)-2-oxoethyl)benzamide | calcd for $C_{27}H_{28}BrFN_3O_4$ [M + H$^+$] 555.1, found 555.1 |
| 84 | 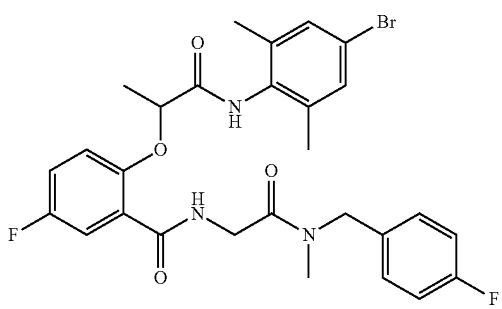 [SMILES: Cc1cc(Br)cc(C)c1NC(=O)C(C)Oc1ccc(F)cc1C(=O)NCC(=O)N(C)Cc1ccc(F)cc1] | 2-((1-((4-bromo-2,6-dimethylphenyl)amino)-1-oxopropan-2-yl)oxy)-5-fluoro-N-(2-((4-fluorobenzyl)(methyl)amino)-2-oxoethyl)benzamide | calcd for $C_{28}H_{29}BrF_2N_3O_4$ [M + H$^+$] 588.1, found 588.1 |
| 85 | 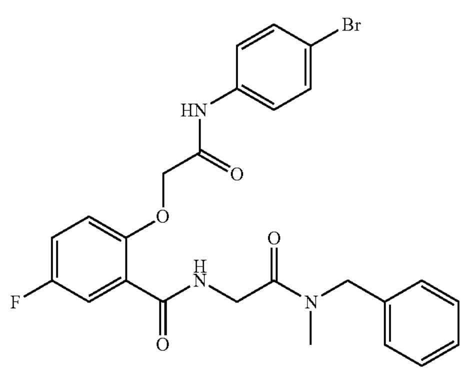 [SMILES: CN(Cc1ccccc1)C(=O)CNC(=O)c1cc(F)ccc1OCC(=O)Nc1ccc(Br)cc1] | N-(2-(benzyl(methyl)amino)-2-oxoethyl)-2-(2-((4-bromophenyl)amino)-2-oxoethoxy)-5-fluorobenzamide | calcd for $C_{25}H_{24}BrFN_3O_4$ [M + H$^+$] 528.1, found 528.1 |

Example 3

Biological Activity of Compound in GCase Activation of 4U-Beta-Glu Glycolysis Assay (Fluorescent Assay for GCase Specific Activity)

The following compounds were assayed as described above in the "Biological Description" section. Compound were assayed in titration from 90 nM to 57 μM final concentration in the screen. Compounds were screened using homogenate from the spleen of a Gaucher patient carrying the N370S mutation and the 4-methylumbelliferyl-β-D-glucopyranoside substrate. $AC_{50}$ values are average of N=2. * Indicates there was no upper asymptote for the dose response curve.

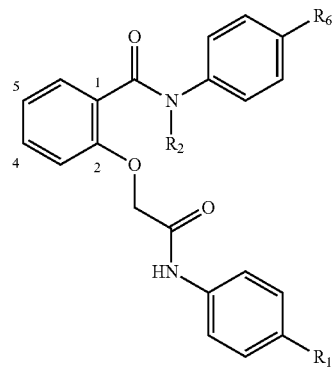

| Cpd No. | $R_1$ | $R_2$ | $R_6$ | CID | $AC_{50}$ (μM) | Efficacy % |
|---|---|---|---|---|---|---|
| 1 (53) | Br | H | Br | 46926406 | 21.1 | 84 |
| 2 (54) | Br | H | F | 36294275 | 2.65 | 51* |
| 3 (55) | Br | H | Cl | 46926395 | 33.4 | 97 |
| 4 (56) | Br | H | I | 46926377 | 21.1 | 75 |
| 5 (57) | Br | H | $CF_3$ | 2459634 | 42.0 | 87 |
| 6 (58) | Br | H | Me | 46926376 | 16.7 | 121 |
| 7 (59) | Br | Me | H | 31528970 | 4.20 | 52 |
| 8 (60) | I | H | Me | 46926387 | 10.1 | 77 |
| 9 (61) | Cl | H | Me | 46926407 | 10.1 | 102 |
| 10 (62) | F | H | Me | 46926400 | 16.7 | 102 |
| 11 (63) | I | H | F | 46926373 | 12.7 | 73 |
| 12 (64) | Cl | H | F | 46943205 | 10.6 | 45 |
| 13 (65) | F | H | F | 46943209 | 16.0 | 85 |
| 14 (66) | I | H | Cl | 46926398 | 20.1 | 79 |
| 15 (67) | Cl | H | Cl | 46943218 | 20.1 | 74 |
| 16 (68) | F | H | Cl | 46926391 | 16.7 | 58 |
| 16a | Cl | H | Br | 46926382 | 15.95 | 66 |

| Cpd No. | $R_1$ | $R_2$ | $R_6$ | CID | $AC_{50}$ (μM) | Efficacy % |
|---|---|---|---|---|---|---|
| 17 (69) | Br | H | H | 24382054 | 2.65 | 67 |
| 18 (70) | I | H | H | 24382059 | 2.11 | 54 |
| 19 (71) | Cl | H | H | 7981680 | 13.3 | 87 |
| 20 (72) | F | H | H | 7981666 | 2.65 | 56 |
| 21 (73) | Br | Me | H | 34284515 | 1.33 | 47 |
| 22 (74) | I | Me | H | 46926402 | 0.84 | 38 |
| 23 (75) | Cl | Me | H | 46926404 | 1.06 | 51 |
| 24 (76) | F | Me | H | 46926393 | 3.34 | 55 |
| 25 (77) | Br | H | $NMe_2$ | 31786241 | 6.66 | 79 |
| 26 (78) | Br | H | OMe | 43001960 | 3.34 | 43 |
| 27 (79) | Br | H | $CF_3$ | 46926394 | 5.29 | 54 |
| 28 (80) | Br | H | Br | 46926386 | 8.39 | 52 |
| 29 (81) | Br | H | t-Bu | 46926396 | 10.1 | 37 |
| 30 (82) | Br | H | I | 46926390 | 21.1 | 45 |
| 31 (83) | Br | H | Cl | 46926388 | 4.20 | 32 |
| 31a | Cl | H | Cl | 46926397 | 5.39 | 52 |

| Cpd No. | $R_1$ | $R_9$ | $R_5$ | $R_6$ | CID | $AC_{50}$ (μM) | Efficacy % |
|---|---|---|---|---|---|---|---|
| 32 (84) | p-I | H | H | H | 46937183 | 5.04 | 82 |
| 33 (85) | p-Br | H | H | H | 46943206 | 3.33 | 53 |
| 34 (86) | p-Cl | H | H | H | 46943223 | 6.66 | 62 |
| 35 (87) | p-F | H | H | H | 46943229 | 6.66 | 42 |
| 36 (88) | p-Br | H | H | p-n-Hex | 46943220 | >10 | ND |
| 37 (89) | p-Br | H | H | p-Me | 46937196 | 0.87 | 40 |
| 38 (90) | p-Br | H | H | p-Br | 46937197 | 1.10 | 31 |
| 39 (91) | p-Br | H | H | p-F | 50985698 | 0.84 | 38 |
| 40 (92) | p-Br | H | H | p-Cl | 46937188 | 1.19 | 33 |
| 41 (93) | p-Br | H | H | p-OMe | 46937201 | 2.15 | 40 |
| 42 (94) | p-Br | H | H | p-t-Bu | 46937194 | 1.27 | 36 |
| 43 (95) | p-Br | H | H | p-CN | 46937202 | 1.67 | 38 |
| 44 (96) | p-I | H | (S)-Me | p-Me | 50985692 | 4.20 | 48 |
| 45 (97) | p-I | H | (R)-Me | p-Me | 50985684 | 3.34 | 73 |
| 46 (98) | p-I | (S)-Me | (R)-Me | p-Me | 53230301 | 16.7 | 28 |
| 47 (99) | p-I | (R)-Me | (R)-Me | p-Me | 53230303 | 1.03 | 25 |
| 47a | p-Me | H | (R)-Me | p-Me | 50985710 | 5.29 | 82 |
| 47b | p-OMe | H | H | p-OMe | 50985703 | 6.66 | 28 |

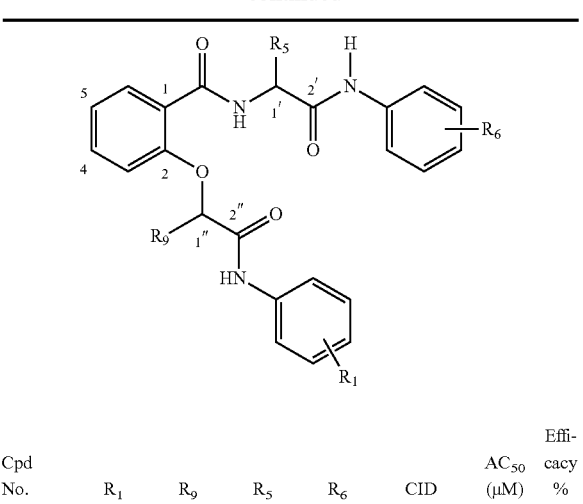

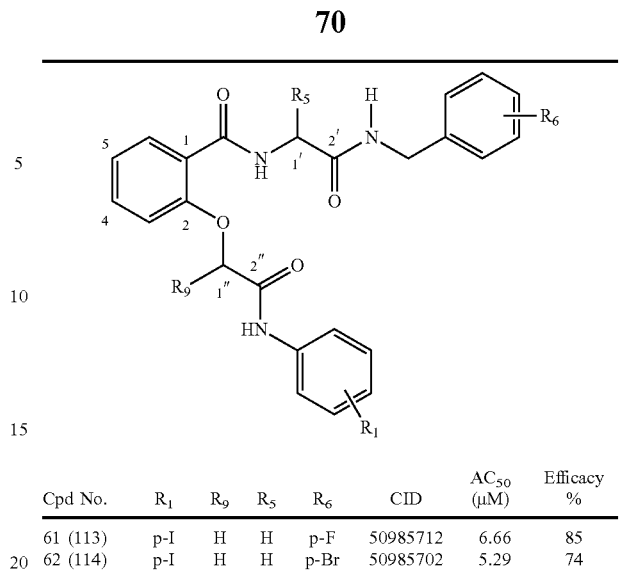

| Cpd No. | R₁ | R₉ | R₅ | R₆ | CID | AC₅₀ (μM) | Efficacy % |
|---|---|---|---|---|---|---|---|
| 47c | p-I | H | H | p-Br | 46937199 | 1.27 | 26 |
| 47d | p-Me | H | (S)-Me | p-Me | | 4.20 | 78 |
| 47e | p-Me | H | Phenyl | p-Me | | 1.67 | 30 |

| Cpd No. | R₁ | R₉ | R₅ | R₆ | CID | AC₅₀ (μM) | Efficacy % |
|---|---|---|---|---|---|---|---|
| 61 (113) | p-I | H | H | p-F | 50985712 | 6.66 | 85 |
| 62 (114) | p-I | H | H | p-Br | 50985702 | 5.29 | 74 |
| 63 (115) | p-I | H | H | p-Cl | 50985718 | 5.29 | 79 |
| 64 (116) | p-I | H | H | p-Me | 50985705 | 2.65 | 40 |
| 65 (117) | p-I | H | H | p-OMe | 50985690 | 4.20 | 47 |
| 65a | p-Br | H | H | p-F | 50985689 | 6.66 | 77 |
| 65b | p-Br | H | H | p-Me | 50985707 | 10.56 | 54 |

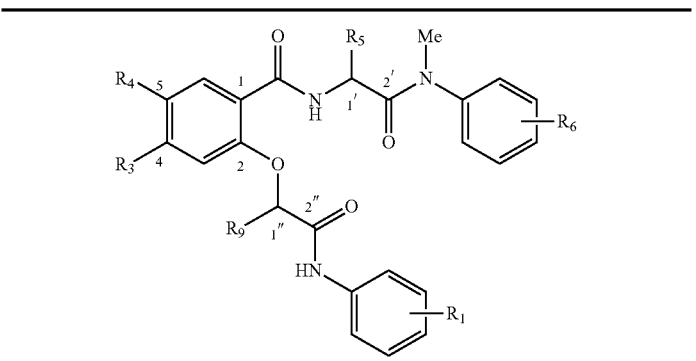

| Cpd No. | R₁ | R₉ | R₃ | R₄ | R₅ | R₆ | CID | AC₅₀ (μM) | Efficacy % |
|---|---|---|---|---|---|---|---|---|---|
| 48 (100) | p-I | H | H | H | H | H | 46943210 | 1.33 | 64 |
| 49 (101) (ML266) | p-Br | H | H | H | H | H | 46943215 | 2.65 | 77 |
| 50 (102) | p-Cl | H | H | H | H | H | 46943225 | 1.67 | 51 |
| 51 (103) | p-F | H | H | H | H | H | 46937190 | 10.1 | 83 |
| 52 (104) | p-I | H | F | H | H | H | 53230304 | 5.29 | 64 |
| 53 (105) | p-I | H | H | F | H | H | 53230298 | 2.66 | 53 |
| 54 (106) | p-I, o-F | H | H | H | H | H | 53230302 | 13.3 | 52 |
| 55 (107) | p-I | H | H | H | H | p-F | 53230294 | 4.20 | 61 |
| 56 (108) | p-I | H | H | F | H | p-F | 53230310 | 1.67 | 40 |
| 57 (109) | p-I, o-F | H | H | F | H | p-F | 53230295 | 10.3 | 38 |
| 58 (110) | p-I, o-F | H | H | F | H | H | 53230314 | 8.19 | 47 |
| 59 (111) | p-I | (R)-Me | H | H | (R)-Me | H | 53230311 | 2.11 | 37 |
| 60 (112) | p-I | (S)-Me | H | H | (R)-Me | H | 53230313 | 21.1 | 30 |
| 60a | p-Br | H | H | H | H | p-Me | 46937196 | | |

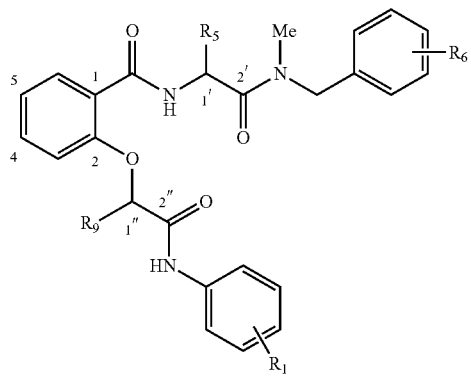

| Cpd No. | $R_1$ | $R_9$ | $R_5$ | $R_6$ | CID | $AC_{50}$ (μM) | Efficacy % |
|---|---|---|---|---|---|---|---|
| 66 (118) | p-I | H | H | H | 50985691 | 2.11 | 78 |
| 67 (119) | p-I | H | (R)-Me | H | 50985713 | 2.65 | 55 |
| 68 (120) | p-I | H | (S)-Me | H | 50985694 | 3.34 | 66 |
| 69 (121) | p-I | (R)-Me | (R)-Me | H | 53230312 | 1.67 | 75 |
| 70 (122) | p-I | (S)-Me | (R)-Me | H | 53230309 | 16.7 | 40 |
| 71 (123) | p-Me | H | (S)-Me | H | 50985688 | 5.17 | 67 |
| 72 (124) | p-Me | H | (R)-Me | H | 50985699 | 4.61 | 108 |
| 73 (125) | p-Me | H | H | H | 50985714 | 5.29 | 82 |

Example 4

Anti-Target Assays Against Alpha-Glucosidase and Alpha-Galactosidase

To characterize compound selectivity, selected hits from the primary screen are screened against purified alpha-glucosidase and alpha-galactosidase, related sugar hydrolases. Alpha-glucosidase is responsible for hydrolysis of terminal, non-reducing 1,4-linked alpha-D-glucose residues with release of alpha-D-glucose, and alpha-galactosidase is a homodimeric glycoprotein that hydrolyzes the terminal alpha-galactosyl moieties from glycolipids and glycoproteins. This is a fluorogenic enzyme assay with 4-methylumbelliferyl-alpha-D-pyranoside and 4-methylumbelliferyl-alpha-D-galactopyranoside as the substrates, respectively. Upon the hydrolysis of this fluorogenic substrate, the resulting product, 1,4-methyllumbelliferone, is be excited at 365 nm and emits at 440 nm. This excitation is be detected by a standard fluorescence plate reader. Data are normalized to the controls for basal activity (without enzyme) and 100% activity (with enzyme). The $AC_{50}$ values are determined from concentration-response data modeled with the standard Hill equation. Assay buffer: 50 mM citric acid (titrated with potassium phosphate to pH 5.0), 0.005% Tween-20, pH 5.0. pH 5.0 is an optimal condition for this enzyme assay. The general protocol for this experiment is given in Table 1 in the "Biological Description" section. Additional details have been previously published in PubChem.

Example 5

Chaperone Translocation Experiments in Human Fibroblasts

This assay quantitates translocated glucocerebrosidase protein in patient-derived fibroblasts following extended compound incubation. The fibroblasts tested in this experiment are homozygous either for N370S glucocerebrosidase or wildtype GCase. Primary dermal fibroblasts derived from skin biopsies from two previously described N370S/N370S Gaucher patients and a control were seeded in Lab-Tek 4 chamber slides (Fisher Scientific, Pittsburgh, Pa.). After compound treatment, fibroblasts were fixed in 3% paraformaldehyde. The cells were permeabilized with 0.1% Triton-X for 10 min. and blocked in PBS containing 0.1% saponin, 100 μM glycine, 0.1% BSA and 2% donkey serum. This was followed by an incubation with mouse monoclonal anti-LAMP1 or LAMP-2 (1:100, Developmental Studies Hybridoma bank, University of Iowa, Iowa City, Iowa) and the rabbit polyclonal anti-GCase R386 antibody (1:500); the cells were washed and incubated with secondary donkey anti-mouse or anti-rabbit antibodies conjugated to ALEXA-488 or ALEXA-555, respectively (Invitrogen, Carlsbad, Calif.), washed again, and mounted in VectaShield with DAPI (Vector Laboratories, Burlingame, Calif.) Table 3.

Cells were imaged with a Zeiss 510 META confocal laser-scanning microscope (Carl Zeiss, Microimaging Inc., Germany) using an Argon (458, 477, 488, 514 nm) 30 mW laser, a HeNe (543 nm) 1 mW laser, and a laser diode (405 nm). Low and high magnification images were acquired using a Plan-Apochromat 20×/0.75 objective and a Plan-Apochromat 100×/1.4 oil DIC objective, respectively. Images were taken with the same laser settings and all the images shown are collapsed z-stacks.

| Step | Parameter | Value | Description |
|---|---|---|---|
| 1 | Reagent | 3000 cells/well | Fibroblasts in DMEM (10% FBS) into 96-well plate |
| 2 | Incubate | 1 day | 37° C. at 5% $CO_2$ |
| 3 | Wash | 1x | Replace medium with OptiMem (2% FBS) with appropriate compound concentrations |
| 4 | Incubate | 2 days | 37° C. at 5% $CO_2$ |
| 5 | Wash | 1x | Replace medium with OptiMem (2% FBS) with appropriate compound concentrations |
| 6 | Incubate | 3 days | 37° C. at 5% $CO_2$ |
| 7 | Wash | 1x | PBS |
| 8 | Reagent | | 3% Paraformaldehyde |
| 9 | Incubate | 15 min | Room temperature |
| 10 | Reagent | 1x | PBS |
| 11 | Wash | 1x | Block Solution (5% goat serum, 0.1% saposon, and 15 mg/mL glycine in PBS |
| 12 | Incubate | 40 min | Room temperature |
| 13 | Wash | 1x | r386 antibody solution |
| 14 | Incubate | Overnight | 4° C. |
| 15 | Wash | 3x | Block solution (5% goat serum and 0.1% saposin) and wait 10 min between washes |

-continued

| Step | Parameter | Value | Description |
|------|-----------|-------|-------------|
| 16 | Reagent | | Secondary antibody (1:100 dilution of Cy-3 for GC, 1:100 dilution of FITC for LAMP2m 1:5000 dilution of Hoechst in 5% goat serum |
| 17 | Incubate | 1 hour | Room temperature |
| 18 | Wash | 3x | PBS wash with 5 minute intervals |
| 19 | Read | | Fluorescence microscope |

Example 6

LC-MS Hydrolysis Experiment

This assay assures that any compound autofluorescence does not interfere with activity in the fluorescence-based primary and secondary assays. A liquid chromatography assay is linked to a mass spectrometer to assess the ability of glucocerebrosidase from spleen homogenate to cleave either 4-methylumbelliferyl-beta-D-glucopyranoside substrate or a labeled version of the natural substrate, glucosylceramide. Both substrates have a pro-fluorescent tag, which allows the product fraction to be easily identified with liquid chromatography; however, identification of the reaction product is done using the mass spectrometer. This tissue homogenate assay most closely reflects physiological conditions in the body.

Chromatography was performed using an Agilent HPLC. The Agilent 1200 LC was equipped with a quaternary pump, a G1315 diode array detector, and a G1321 Fluorescent Detector. A 4.6×250 mm Agilent Eclipse Plus C18 (5 micron) at ambient temperature was used at a flow rate of 1.8 mL/Min with a gradient of 85/15 (methanol/0.1% formic acid in water) to 100 methanol over 10 minutes. The BODIPY tagged natural substrate was monitored using fluorescence detection with an excitation wavelength of 505 nanometers and emission wavelength at 540 nanometers.

Example 7

Measurement of GCase Activity in Controls and Patients with Type 1 Gaucher Disease Peripheral blood mononuclear cells from controls and patients with type 1 GD were isolated using Ficoll gradients, and monocytes purified using magnetic CD16 microbeads (StemCell Technology). Macrophages were differentiated from purified monocytes using 10 ng/ml of macrophage colony stimulating factor M-CSF (R&D Systems) in RPMI 1640 medium, supplemented with 10% fetal calf serum (FCS) (Invitrogen). On days 3 and 6, media was refreshed. These hMacs (human macrophages) were cultured in black 96-well plates and treated with compound at the appropriate concentration for 6 days. Following this they were treated with 100 μl of an assay buffer which consists of 200 mM sodium acetate (pH4), 5 mM 4MU-βGlu (substrate that gets cleaved with enzyme) and protease inhibitor cocktail (Sigma) for 1 hr at 37° C. The reaction was halted using a stop solution (1 M NaOH and 1 M Glycine) and fluorescence was measured. The fluorescence is a measurement of the specific activity.

What is claimed is:
1. A compound o pharmaceutically acceptable salt thereof, of Formula (I):

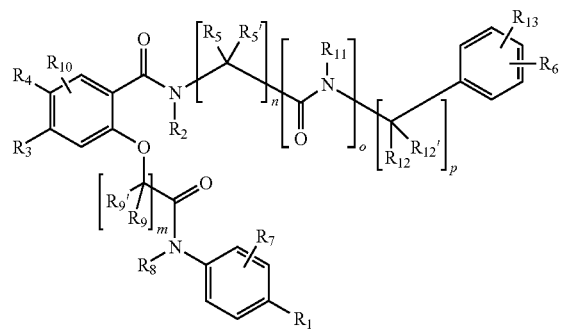

wherein:
m is 1, n is 1, o is 1, and p is 0;
$R_1$ is a halogen, $C_1$-$C_2$alkyl, or $C_1$-$C_2$alkoxy;
$R_2$ is hydrogen or $C_1$-$C_4$alkyl;
$R_3$ and $R_4$ are independently selected from hydrogen, halogen, amino, cyano, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy;
$R_5$, $R_5'$, $R_9$, $R_9'$, and $R_{12}$, $R_{12}'$ are independently chosen at each occurrence from hydrogen, fluoro, phenyl, ($C_3$-$C_6$cycloalkyl)$C_0$-$C_2$alkyl, and $C_1$-$C_4$alkyl;
$R_6$ is one substituent selected from hydrogen, halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy;
$R_7$, $R_{10}$, and $R_{13}$ are each 0 or 1 or more substituents independently chosen from halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy; and
$R_8$ and $R_{11}$ are independently chosen from hydrogen and $C_1$-$C_4$alkyl.
2. A compound or salt of claim 1 of the formula:

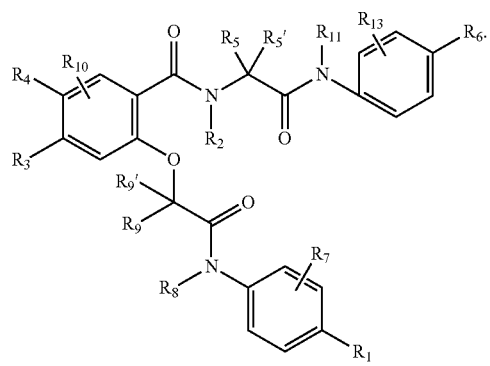

3. A compound or salt of claim 1 wherein
$R_1$ is halogen;
$R_2$ is hydrogen or methyl;
$R_3$ and $R_4$ are independently hydrogen or methyl;
$R_6$ is halogen or trifluoromethyl;
$R_7$, $R_{10}$, and $R_{13}$ are each 0 substituents;
$R_8$ is hydrogen; and
$R_9$ and $R_9'$ are both hydrogen.

4. A compound or salt of claim 1, wherein
$R_1$ is halogen;
$R_2$ is hydrogen or methyl;
$R_3$ and $R_4$ are independently hydrogen or methyl;
$R_5$ and $R_5'$ are independently hydrogen or methyl;
$R_6$ is hydrogen, halogen, $C_1$-$C_4$alkyl, $C_1$-$C_2$alkoxy, mono- or di-$C_1$-$C_2$alkylamino, or trifluoromethyl;
$R_7$, $R_{10}$, and $R_{13}$ are each 0 substitutents;
$R_8$ is hydrogen; and
$R_9$ and $R_9'$ are both hydrogen.

5. A compound or salt of claim 1, wherein:
$R_1$ is halogen;
$R_2$ is hydrogen;
$R_3$ and $R_4$ are independently hydrogen, halogen, or methyl;
$R_5$ and $R_5'$ are independently hydrogen or methyl;
$R_6$ is hydrogen, halogen, cyano, $C_1$-$C_6$alkyl, $C_1$-$C_2$alkoxy, mono- or di-$C_1$-$C_2$alkylamino, or trifluoromethyl;
$R_7$ is 0 or 1 halogen substituents;
$R_8$ is hydrogen;
$R_9$ is hydrogen or methyl;
$R_9'$ is hydrogen;
$R_{10}$ and $R_{13}$ are each 0 substituents; and
$R_{11}$ is hydrogen or methyl.

6. A compound or salt of claim 5, wherein
$R_3$ and $R_4$ are both hydrogen;
$R_5$ is hydrogen or methyl;
$R_5'$ is hydrogen;
$R_6$ is hydrogen, halogen, cyano, $C_1$-$C_6$alkyl, $C_1$-$C_2$alkoxy, or mono- or di-$C_1$-$C_2$alkylamino;
$R_{10}$ and $R_{13}$ are each 0 substituents; and
$R_{11}$ is hydrogen.

7. A compound or salt of claim 5, wherein
$R_3$ and $R_4$ are independently hydrogen or halogen;
$R_5$ is hydrogen or methyl;
$R_5'$ is hydrogen;
$R_6$ is hydrogen or halogen;
$R_7$, $R_{10}$, and $R_{13}$ are each 0 substituents; and
$R_{11}$ is methyl.

8. A compound or salt of claim 2, wherein
$R_1$ is halogen;
$R_2$, $R_3$, $R_4$, $R_5$, $R_8$, $R_9$, and $R_{11}$ are each independently hydrogen or methyl;
$R_5'$ and $R_9'$ are both hydrogen;
$R_6$ is hydrogen, halogen, cyano, $C_1$-$C_6$alkyl, $C_1$-$C_2$alkoxy, or mono- or di-$C_1$-$C_2$alkylamino;
$R_7$ is 2,6-dimethyl; and
$R_{10}$ and $R_{13}$ are 0 substituents.

9. A compound or salt thereof of claim 1, wherein the compound is:
2-(2-(4-iodophenyl amino)-2-oxoethoxy)-N-(2-oxo-2-(phenyl amino)ethyl)benzamide;
2-(2-(4-chlorophenyl amino)-2-oxoethoxy)-N-(2-oxo-2-(phenyl amino)ethyl)benzamide;
2-(2-(4-fluoro-phenylamino)-2-oxoethoxy)-N-(2-oxo-2-(phenyl amino)ethyl)benzamide;
2-(2-(4-bromophenylamino)-2-oxoethoxy)-N-(4-hexyl phenyl)benzamide;
2-(2-(4-bromophenyl amino)-2-oxoethoxy)-N-(2-oxo-2-(p-tolylamino)ethyl)benzamide;
2-(2-(4-bromophenyl amino)-2-oxoethoxy)-N-(2-(4-bromo phenylamino)-2-oxoethyl)benzamide;
2-(2-((4-bromophenyl)amino)-2-oxoethoxy)-N-(2-((4-fluorophenyl)amino)-2-oxoethyl)benzamide;
2-(2-((4-bromophenyl)amino)-2-oxoethoxy)-N-(2-((4-chlorophenyl)amino)-2-oxoethyl)benzamide;
2-(2-((4-bromophenyl)amino)-2-oxoethoxy)-N-(2-((4-methoxyphenyl)amino)-2-oxoethyl)benzamide;
2-(2-(4-bromophenyl amino)-2-oxoethoxy)-N-(2-(4-tert-butyl phenylamino)-2-oxoethyl)benzamide;
2-(2-(4-bromophenyl amino)-2-oxoethoxy)-N-(2-(4-cyano phenylamino)-2-oxoethyl)benzamide;
(R)-2-(2-(4-iodophenyl amino)-2-oxoethoxy)-N-(1-oxo-1-(p-tolylamino)propan-2-yl)benzamide;
(S)-2-(2-(4-iodophenyl amino)-2-oxoethoxy)-N-(1-oxo-1-(p-tolylamino)propan-2-yl)benzamide;
2-((S)-1-(4-iodophenylamino)-1-oxopropan-2-yloxy)-N-((R)-1-oxo-1-(p-tolylamino)propan-2-yl)benzamide;
2-((R)-1-(4-iodophenylamino)-1-oxopropan-2-yloxy)-N-((R)-1-oxo-1-(p-tolylamino)propan-2-yl)benzamide;
(R)-N-(1-oxo-1-(p-tolylamino) propan-2-yl)-2-(2-oxo-2-(p-tolylamino)ethoxy)benzamide;
2-(2-(4-methoxyphenyl amino)-2-oxoethoxy)-N-(2-(4-methoxyphenylamino)-2-oxoethyl)benzamide;
N-(2-(4-bromophenyl amino)-2-oxoethyl)-2-(2-(4-iodophenyl amino)-2-oxoethoxy)benzamide;
2-(2-((4-iodophenyl)amino)-2-oxoethoxy)-N-(2-(methyl(phenyl)amino)-2-oxoethyl)benzamide;
2-(2-((4-bromophenyl)amino)-2-oxoethoxy)-N-(2-(methyl(phenyl)amino)-2-oxoethyl)benzamide;
2-(2-(4-chlorophenylamino)-2-oxoethoxy)-N-(2-(methyl(phenyl)amino)-2-oxoethyl)benzamide;
2-(2-(4-fluorophenylamino)-2-oxoethoxy)-N-(2-(methyl(phenyl)amino)-2-oxoethyl)benzamide;
4-fluoro-2-(2-(4-iodophenyl amino)-2-oxoethoxy)-N-(2-(methyl(phenyl)amino)-2-oxoethyl)benzamide;
5-fluoro-2-(2-(4-iodophenyl amino)-2-oxoethoxy)-N-(2-(methyl(phenyl)amino)-2-oxoethyl)benzamide;
2-(2-((2-fluoro-4-iodophenyl)amino)-2-oxoethoxy)-N-(2-(methyl(phenyl)amino)-2-oxoethyl)benzamide;
4-fluoro-N-(2-((4-fluorophenyl)(methyl)amino)-2-oxoethyl)-2-(2-(4-iodophenylamino)-2-oxoethoxy)benzamide;
5-fluoro-N-(2-((4-fluorophenyl)(methyl)amino)-2-oxoethyl)-2-(2-(4-iodophenylamino)-2-oxoethoxy)benzamide;
5-fluoro-2-(2-(2-fluoro-4-iodophenylamino)-2-oxoethoxy)-N-(2-((4-fluorophenyl)(methyl)amino)-2-oxoethyl)benzamide;
5-fluoro-2-(2-(2-fluoro-4-iodophenyl amino)-2-oxoethoxy)-N-(2-(methyl(phenyl)amino)-2-oxoethyl)benzamide;

2(((S)-1-((4-iodophenyl)amino)-1-oxopropan-2-yl)oxy)-N-((R)-1-(methyl(phenyl)amino)-1-oxopropan-2-yl) benzamide;

2-((R)-1-(4-iodophenyl amino)-1-oxopropan-2-yloxy)-N-((R)-1-oxo-1-(p-tolylamino)propan-2-yl)benzamide;

2-(2-(4-bromophenylamino)-2-oxoethoxy)-N-(2-(methyl(p-tolyl)amino)-2-oxoethyl)benzamide;

2-(2-((4-bromo-2,6-dimethylphenyl)amino)-2-oxoethoxy)-5-fluoro-N-(2-((4-fluorophenyl)(methyl)amino)-2-oxoethyl)benzamide;

2-(2-((4-bromo-2,6-dimethylphenyl)amino)-2-oxoethoxy)-5-fluoro-N-(2-(methyl(phenyl)amino)-2-oxoethyl)benzamide;

2-(2-((4-bromophenyl)amino)-2-oxoethoxy)-5-fluoro-N-(2-((4-fluorophenyl)(methyl)amino)-2-oxoethyl)benzamide;

2-(2-((4-bromophenyl)amino)-2-oxoethoxy)-5-fluoro-N-(2-(methyl(phenyl)amino)-2-oxoethyl)benzamide;

(R)-2-((1-((4-bromo-2,6-dimethylphenyl)amino)-1-oxopropan-2-yl)oxy)-5-fluoro-N-(2-((4-fluorophenyl)(methyl)amino)-2-oxoethyl)benzamide;

(R)-2-((1-((4-bromo-2,6-dimethylphenyl)amino)-1-oxopropan-2-yl)oxy)-5-fluoro-N-(2-(methyl(phenyl)amino)-2-oxoethyl)benzamide;

2-((1-((4-bromo-2,6-dimethylphenyl)amino)-1-oxopropan-2-yl)oxy)-5-fluoro-N-(2-(methyl(phenyl)amino)-2-oxoethyl)benzamide;

N-(2-(benzyl(methyl)amino)-2-oxoethyl)-2-(2-((4-bromophenyl)amino)-2-oxoethoxy)-5-fluorobenzamide.

10. A pharmaceutical composition comprising a compound of claim 1 together with a pharmaceutically acceptable carrier.

11. A method of treating a lysosomal storage disorder in a patient or preventing the symptoms of the lysosomal storage disorder in the patient having a GBA gene mutation comprising providing an effective amount of a compound of Formula (I) or pharmaceutically acceptable salt thereof to the patient, wherein Formula (I) is:

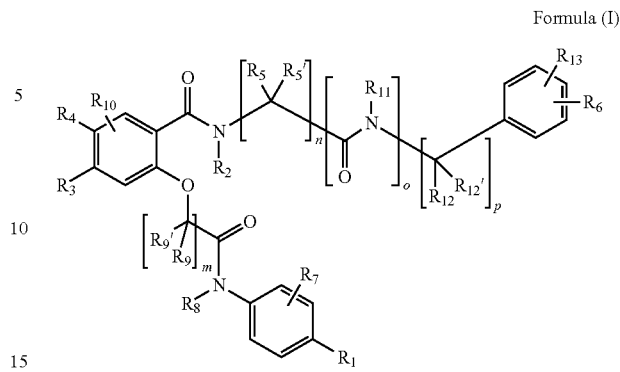

Formula (I)

Wherein
m is 1; n is 1; o is 1; and p is 0;
$R_1$ is a halogen, $C_1$-$C_2$alkyl, or $C_1$-$C_2$alkoxy;
$R_2$ is hydrogen or $C_1$-$C_4$alkyl;
$R_3$ and $R_4$ are independently selected from hydrogen, halogen, amino, cyano, $C_1$-$C_4$alkyl, $C_1$-$C_4$alkoxy, mono- and di-$C_1$-$C_4$alkylamino), $C_1$-$C_2$haloalkyl, and $C_1$-$C_2$haloalkoxy;
$R_5$, $R_5'$, $R_9$, $R_9'$, and $R_{12}$, $R_{12}'$ are independently chosen at each occurrence from hydrogen, fluoro, phenyl, $(C_3$-$C_6$cycloalkyl)$C_0$-$C_2$alkyl, and $C_1$-$C_4$alkyl;
$R_6$ is one substituent selected from hydrogen, halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy;
$R_7$, $R_{10}$, and $R_{13}$ are each 0 or 1 or more substituents independently chosen from halogen, hydroxyl, amino, cyano, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy; and
$R_8$ and $R_{11}$ are independently chosen from hydrogen and $C_1$-$C_4$alkyl.

* * * * *

UNITED STATES PATENT AND TRADEMARK OFFICE
CERTIFICATE OF CORRECTION

PATENT NO. : 9,464,035 B2  
APPLICATION NO. : 14/388494  
DATED : October 11, 2016  
INVENTOR(S) : Juan Jose Marugan et al.

Page 1 of 1

It is certified that error appears in the above-identified patent and that said Letters Patent is hereby corrected as shown below:

In the Specification

Column 1, Line 16 should be corrected to read:
"This invention was made with government support under HG005031 awarded by the National Institutes of Health. The government has certain rights in the invention."

Signed and Sealed this
Sixteenth Day of April, 2019

Andrei Iancu
*Director of the United States Patent and Trademark Office*